(12) United States Patent
Guzman et al.

(10) Patent No.: US 9,937,493 B1
(45) Date of Patent: Apr. 10, 2018

(54) PIPETTING DEVICE, PIPETTE TIP COUPLER, AND PIPETTE TIP: DEVICES AND METHODS

(71) Applicant: Hamilton Company, Reno, NV (US)

(72) Inventors: Jose Eduardo Guzman, Sparks, NV (US); Thomas Barresi, Reno, NV (US); Dana A. Belton, Sparks, NV (US)

(73) Assignee: Hamilton Company, Reno, NV (US)

( * ) Notice: Subject to any disclaimer, the term of this patent is extended or adjusted under 35 U.S.C. 154(b) by 0 days.

(21) Appl. No.: 15/838,811

(22) Filed: Dec. 12, 2017

Related U.S. Application Data

(63) Continuation of application No. 15/474,678, filed on Mar. 30, 2017.

(60) Provisional application No. 62/350,302, filed on Jun. 15, 2016, provisional application No. 62/350,291, filed on Jun. 15, 2016.

(51) Int. Cl.
*B01L 3/00* (2006.01)
*B01L 3/02* (2006.01)

(52) U.S. Cl.
CPC .......... *B01L 3/0279* (2013.01); *B01L 2200/04* (2013.01); *B01L 2200/0689* (2013.01); *B01L 2300/0832* (2013.01); *B01L 2300/123* (2013.01)

(58) Field of Classification Search
CPC combination set(s) only.
See application file for complete search history.

(56) References Cited

U.S. PATENT DOCUMENTS

| | | | |
|---|---|---|---|
| 3,732,734 A * | 5/1973 | Avakian | B01L 3/0275 141/311 R |
| 4,023,716 A | 5/1977 | Shapiro | |
| 4,187,724 A | 2/1980 | Citrin | |
| 4,268,481 A * | 5/1981 | Suovaniemi | B01L 3/0234 222/391 |
| 4,830,832 A | 5/1989 | Arpagaus | |
| 4,863,695 A | 9/1989 | Fullemann | |
| 4,967,604 A | 11/1990 | Arpagaus | |

(Continued)

FOREIGN PATENT DOCUMENTS

| | | |
|---|---|---|
| DE | 102015213005 | 12/2017 |
| EP | 2311566 | 4/2011 |

(Continued)

*Primary Examiner* — Brian R Gordon
(74) *Attorney, Agent, or Firm* — Weintraub Tobin

(57) ABSTRACT

Pipette tip coupler and a disposable pipette tip for a pipette device comprises a stepped coupler shoulder complementary to an axially stepped pipette tip shoulder; a first elastomeric element carried by the coupler at a location superior to the coupler shoulder; and a second elastomeric element carried by the coupler at a location inferior to the coupler shoulder wherein the first elastomeric element has a compressed radially expanded state that provides a sealing abutment with a first working surface formed in the interior surface of the pipette tip while compressing the second elastomeric element into sealing abutment with a second working surface formed in the interior surface of the pipette tip and while abutting the proximally facing axial stop surface of the pipette tip with the distally facing axial stop surface of the pipette coupler to define an axial coupling position of the pipette tip on the pipette device.

30 Claims, 61 Drawing Sheets

(56) References Cited

U.S. PATENT DOCUMENTS

| | | | |
|---|---|---|---|
| 5,200,151 A | 4/1993 | Long | |
| 5,232,669 A * | 8/1993 | Pardinas | B01L 3/0275 206/562 |
| 5,620,660 A | 4/1997 | Belgardt | |
| 5,948,359 A * | 9/1999 | Kalra | G01N 1/312 422/510 |
| 6,168,761 B1 | 1/2001 | Kelly | |
| 6,171,553 B1 | 1/2001 | Petrek | |
| 6,248,295 B1 | 6/2001 | Petrek | |
| 6,399,024 B1 | 6/2002 | Bevirt | |
| 6,495,106 B1 | 12/2002 | Kalra | |
| 6,568,288 B2 | 5/2003 | Rainin | |
| 6,737,023 B1 | 5/2004 | Kelly | |
| 6,745,636 B2 | 6/2004 | Rainin | |
| 6,780,381 B2 | 8/2004 | Yiu | |
| 6,955,077 B2 | 10/2005 | Blaszcak | |
| 6,967,004 B2 | 11/2005 | Rainin | |
| 6,973,845 B2 | 12/2005 | Bell | |
| 7,033,543 B1 | 4/2006 | Panzer | |
| 7,047,828 B2 | 5/2006 | Blaszcak | |
| 7,320,259 B2 | 1/2008 | Jessop | |
| 7,344,680 B2 | 3/2008 | Mahler | |
| 7,641,859 B2 | 1/2010 | Cote | |
| 7,662,343 B2 | 2/2010 | Mathus | |
| 7,662,344 B2 | 2/2010 | Mathus | |
| 7,690,293 B2 | 4/2010 | Bensley | |
| 8,163,256 B2 | 4/2012 | Cote | |
| 8,202,495 B1 * | 6/2012 | Smith | B01L 3/0275 422/500 |
| 8,277,757 B2 | 10/2012 | Kelly | |
| 8,337,782 B2 | 12/2012 | Bensley | |
| 8,398,934 B2 | 3/2013 | Bensley | |
| 8,501,118 B2 | 8/2013 | Mathus | |
| 8,512,650 B2 | 8/2013 | Jungheim | |
| 8,524,170 B2 | 9/2013 | Petrek | |
| 8,557,197 B2 | 10/2013 | Leckebusch | |
| 8,703,071 B2 | 4/2014 | Cerra | |
| 8,877,513 B2 | 11/2014 | Mathus | |
| 9,079,178 B2 | 7/2015 | Sheldon | |
| 9,333,500 B2 | 5/2016 | Mathus | |
| 9,346,045 B2 | 5/2016 | Blumentritt | |
| 9,415,388 B2 | 8/2016 | Panzer | |
| 9,566,580 B2 * | 2/2017 | Jaaskelainen | B01L 3/0217 |
| 9,664,702 B2 * | 5/2017 | Holmes | G01N 35/0092 |
| 2003/0177849 A1 * | 9/2003 | Matsuda | B01L 3/0279 73/864.14 |
| 2005/0175511 A1 | 8/2005 | Cote | |
| 2005/0184516 A1 | 8/2005 | Seguin | |
| 2005/0204832 A1 | 9/2005 | Jessop | |
| 2005/0255005 A1 | 11/2005 | Motadel | |
| 2006/0233669 A1 | 10/2006 | Panzer | |
| 2008/0078258 A1 | 4/2008 | Price | |
| 2009/0280033 A1 * | 11/2009 | Cote | B01L 3/0279 422/400 |
| 2010/0196210 A1 * | 8/2010 | Jungheim | B01L 3/0275 422/526 |
| 2011/0076205 A1 | 3/2011 | Kelly | |
| 2013/0136672 A1 | 5/2013 | Blumentritt | |
| 2013/0216705 A1 | 8/2013 | Sprung | |
| 2014/0056781 A1 | 2/2014 | Jaaskelainen | |
| 2014/0219887 A1 * | 8/2014 | Sheldon | B01L 3/0279 422/509 |
| 2015/0037227 A1 * | 2/2015 | Ding | B01L 3/0293 422/509 |
| 2015/0086447 A1 | 3/2015 | Mathus | |
| 2015/0239129 A1 | 8/2015 | Buchloh | |
| 2015/0276107 A1 | 10/2015 | Stadler | |
| 2016/0051979 A1 | 2/2016 | Herbst | |
| 2017/0197209 A1 * | 7/2017 | Motadel | B01L 3/0279 |

FOREIGN PATENT DOCUMENTS

| | | |
|---|---|---|
| JP | 3748231 | 2/2006 |
| KR | 20120008943 | 12/2012 |

* cited by examiner

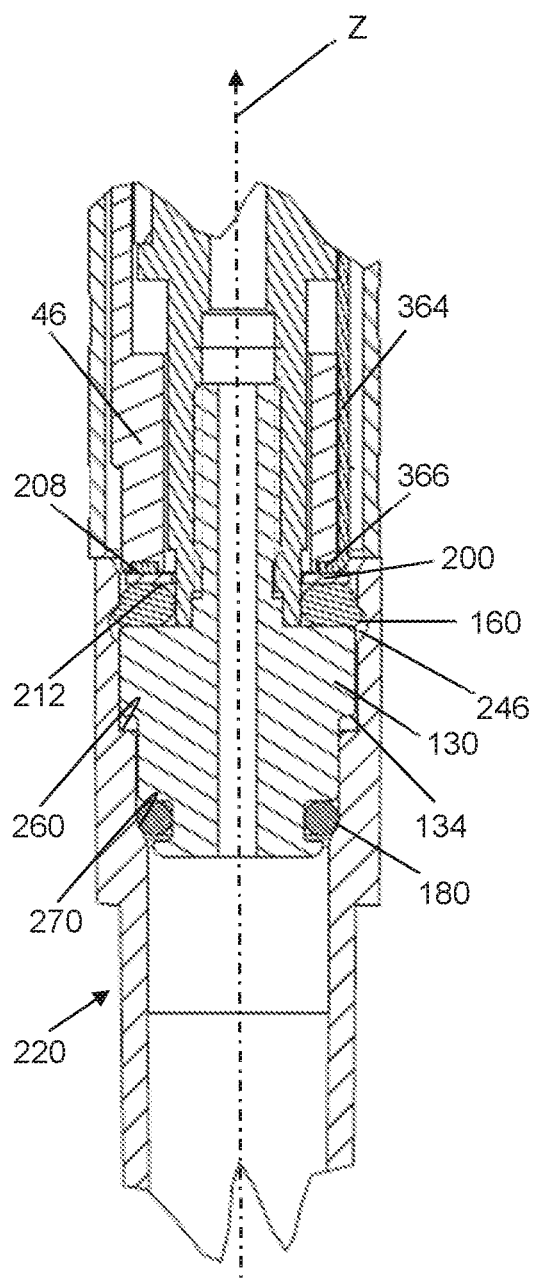
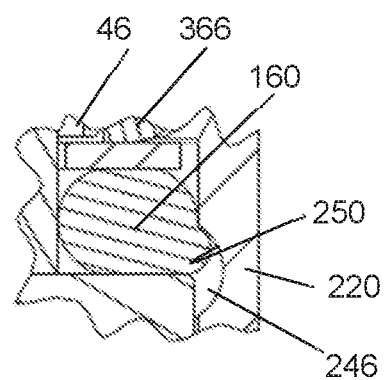
FIG. 21
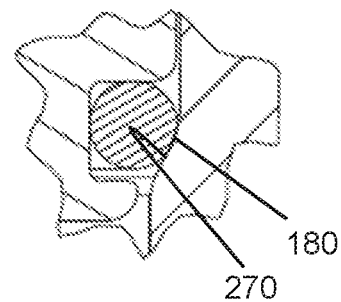
FIG. 22
FIG. 20

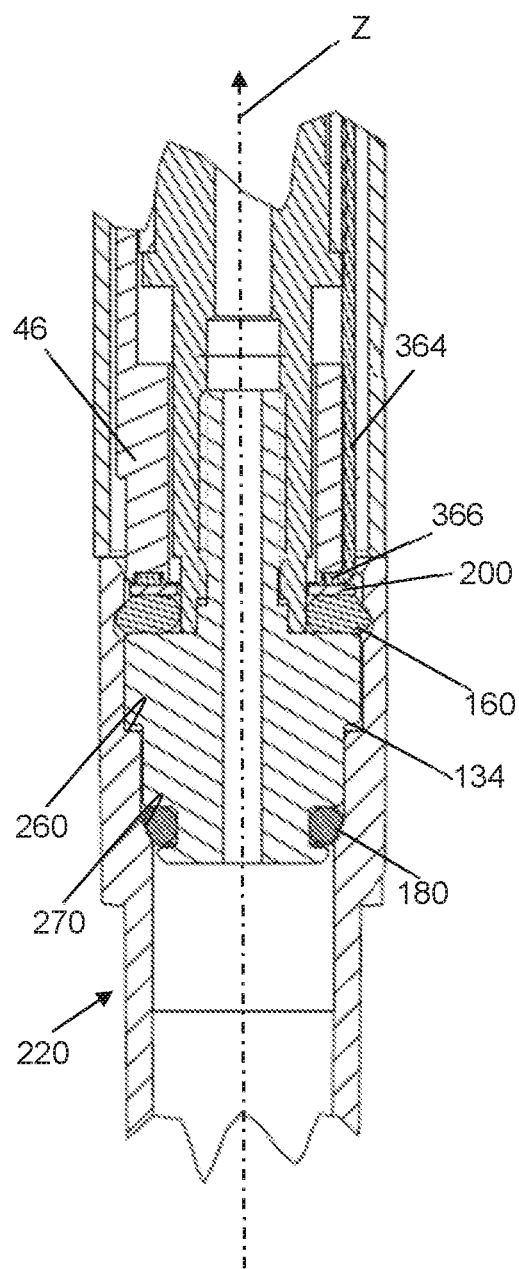
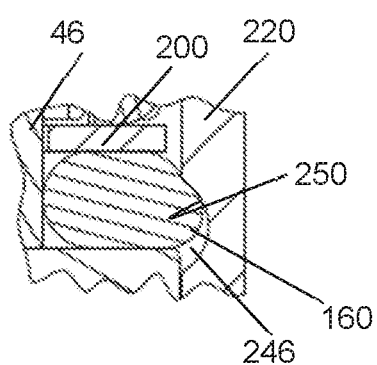
FIG. 24
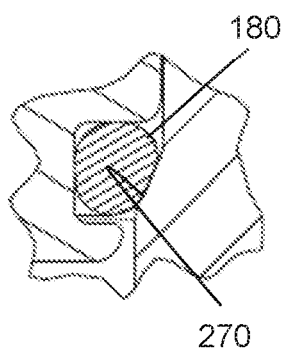
FIG. 23  FIG. 25

PIPETTING DEVICE, PIPETTE TIP COUPLER, AND PIPETTE TIP: DEVICES AND METHODS

CROSS-REFERENCE TO RELATED APPLICATIONS

This application is a continuation of and claims the benefit of priority from U.S. patent application Ser. No. 15/474,678, which is entitled "Pipetting Device, Pipette Tip Coupler, and Pipette Tip: Devices and Methods" and filed on Mar. 30, 2017, which claims the benefit of priority from two (2) U.S. Provisional Patent Application Nos. 62/350,291 filed Jun. 15, 2016, and 62/350,302 filed Jun. 15, 2016, all of which are fully incorporated herein by reference.

FIELD

This disclosure pertains generally to pipetting devices, and more particularly to pipette tip couplers, disposable pipette tips, coupler and tip combinations, and coupling and decoupling methods of at least one disposable pipette tip to or from at least one pipette tip coupler carried by a pipette device.

BACKGROUND

Pipette devices are used in a multitude of industries for the transfer of liquids to conduct experimental analysis. As such, to provide control within the experiments being performed, disposable pipette tips are used and intended for one-time use. Disposable pipette tips are employed with both manual pipette devices and automated pipette devices having a large number of pipette units arranged in a row or in a matrix for aspirating samples simultaneously from a large number of vessels and dispensing them elsewhere.

Disposable pipette tips have been constructed historically to interface to either a conical or stepped coupling stud. In the cases where a conical coupling stud is used, the disposable tip is constructed in a manner that it must be pre-stressed onto the coupling stud to provide an air tight seal. Due to the tolerances of the two interfacing components, the distance to the end of the tip that comes in contact with liquid is not well controlled. In addition, high press forces are required to pre-stress the tip to create the air tight seal. As a result, microfissures may be formed in the pipette tip which are a cause of leakage. Moreover, the high press forces upon placement of the pipette tip have the disadvantage that for the release of the pipette tip correspondingly high forces have to be applied.

The assignee of the present application, HAMILTON Company, teaches in U.S. Pat. No. 7,033,543, issued Apr. 25, 2006, a stepped coupling stud in conjunction with an O-ring that provides a solution for reducing the high press force required to create an air tight seal as well as providing well defined axial positioning of the end of the tip that comes in contact with liquid. As the O-ring is compressed, it provides an axially directed force to not only provide the air-tight seal, but to engage an axial coupling feature on the coupling stud to a counter axial coupling feature on the tip.

Notwithstanding, current systems utilizing a stepped coupling stud and a solitary O-ring configuration are problematic when the O-ring becomes compromised because the result is an impairment in the air-tight seal and the performance of the pipette device.

Additionally, the compression of the O-ring results in the deformation of the O-ring which in turn provides the axially directed force and air-tight seal against the working surface of the pipette tip. Counter to this operation, when the compression of the O-ring is removed, the O-ring must disengage from the working surface of the pipette tip to allow the pipette tip to be removed from the coupling stud and the pipette device for disposal. If the O-ring does not fully decompress, some residual force will remain resulting in keeping the tip engaged to the coupling stud and thus requiring an automated external axial counterforce to remove the tip for disposal.

Moreover, as the size of the holes to and/or from which liquid is transferred decreases, the need for precision positioning of all of the tips in a controlled manner increases in order to allow successful targeting.

Hence, there is a need to ameliorate or overcome one or more of the significant shortcomings delineated hereinabove.

SUMMARY

Accordingly, and in one aspect, an embodiment of the present disclosure ameliorates or overcomes one or more of the shortcomings of the known prior art by providing a pipette tip coupler device and a disposable pipette tip combination which comprises dual elastomeric elements in the form of, but not limited to, dual O-rings carried on the coupler and dual complemental interior working surfaces formed in the pipette tip to respectively engage the dual O-rings to provide dual coacting seals to preclude impairment in an air-tight seal by a single point seal deterioration or failure.

In particular, and in one aspect, an embodiment of the present disclosure provides a pipette tip coupler device and disposable pipette tip combination which comprises a first seal achieved from a compression of an upper or primary elastomeric element of the coupler against a first working surface of the pipette tip which pre-stresses the pipette tip axially upward causing a lower or secondary elastomeric element of the coupler to be pre-stressed against a second working surface of the pipette tip forming a second seal. This dual seal configuration eliminates the single point seal deterioration or failure of the known prior art.

In addition, and in one aspect, the secondary elastomeric element, when compressed against the second working surface, provides a counter axial force to the primary elastomeric element wherein at least one benefit of this counter axial force is that additional force is applied to the first working surface by the primary elastomeric element when the primary elastomeric element is in its compressed state for providing a stronger seal.

A further benefit of the counter axial force is that when the primary elastomeric element is uncompressed, the counter axial force of the secondary elastomeric element defines a counter axially directed disengaging force that aids in the removal of the pipette tip from the pipette tip coupler for disposal.

In another aspect, an embodiment of the present disclosure provides a pipette tip coupler and disposable pipette tip device combination comprising dual elastomeric elements in the form of, but not limited to, dual O-rings on the coupler and dual complemental working surfaces in the pipette tip to provide a resultant axial force achieved from a compression of an upper or primary elastomeric element and a lower or secondary elastomeric element pre-stressing the disposable pipette tip into an axial coupling position which is provided by a distally facing axial stop surface of the pipette tip coupler and a proximally facing complimentary counter axial stop surface of the disposable pipette tip such that a perpendicular datum is established to a longitudinal axis of a channel of a pipette device carrying the pipette tip coupler and disposable pipette tip combination which provides for tip straightness and controlled concentricity.

One benefit of the resultant axial force coupling position over the known prior art is the establishment of this perpendicular datum which provides for tip straightness and controlled concentricity. Concentricity becomes worse as an angle defined herein as "ø" between a transverse axis and the longitudinal axis perpendicular to the transverse axis is allowed to increase. Thus, controlled concentricity becomes especially important on a multi-channel system and targeting multiple wells. Accordingly, the pipette tip coupler device and disposable tip combination provides tighter concentricity to allow for tighter precision of all the tips in a controlled manner allowing successful targeting of multiple wells and/or smaller holes to and/or from which liquid is transferred.

In another aspect, an embodiment of the present disclosure provides a pipette tip coupler device and disposable tip combination comprising dual elastomeric elements in the form of, but not limited to, dual O-rings on the coupler and dual complementary working surfaces in the pipette tip to provide precise control of an axial coupled position defined as an axial distance from a distally facing axial stop surface of the pipette tip coupler to the end of the pipette tip that contacts liquid when the pipette tip coupler and disposable pipette tip are in a coupled configuration. This, combined with tip straightness, allows for a pipette device carrying the pipette tip coupler and disposable tip combination to target smaller holes. Additionally, smaller volumes of liquid can be transferred resulting from the known fixed distance of the disposable pipette tip allowing for a controlled touch of the pipette tip/liquid to a working surface onto or from which liquid is to be transferred.

In yet another aspect, an embodiment of the present disclosure provides a pipette tip coupler device and disposable pipette tip combination comprising an angled squeeze mechanism that directs the motion of the upper or primary elastomeric element as it is compressed and comes into contact with the first working surface of the pipette tip. The result is more axial force to pre-stress the pipette tip into the axial coupling position.

Further aspects of the embodiments of the present disclosure will become apparent from the detailed description provided below, when taken together with the attached drawings and claims. It should be understood, however, that numerous modifications and adaptations may be resorted to without departing from the scope and fair meaning of the claims as set forth below following the detailed description of preferred embodiments of the present disclosure.

BRIEF DESCRIPTION OF THE SEVERAL VIEWS OF THE DRAWINGS

The foregoing summary, as well as the following detailed description of the disclosure, will be more fully understood by reference to the following drawings which are for illustrative purposes only, and are not intended to limit the scope of the present disclosure. Also, it is appreciable that the drawings are not necessarily in scale as some components may be shown to be enlarged or to be out of proportion relative to the size in actual implementation in order to more clearly illustrate one or more concepts of the present disclosure. In the drawings:

FIG. 20 is a fragmentary, longitudinal sectional, side elevational view of the first example embodiment of the pipette tip coupler moved into the disposable pipette tip with the squeeze ring being pushed on for squeezing the primary O-ring from an unsqueezed state to a first compressed and extruded state for starting a process of lifting the tip up to engage the coupler while starting a process of compressing the secondary O-ring.

FIG. 21 is a longitudinal sectional, side elevational, fragmented detailed view of squeezing the primary O-ring to the first compressed and extruded state as is illustrated in FIG. 20.

FIG. 22 is a longitudinal sectional, side elevational, fragmented detailed view of the secondary O-ring in the first compressed state against the tip sealing seat or surface as is illustrated in FIG. 20.

FIG. 23 is a fragmentary, longitudinal sectional, side elevational view of the first example embodiment of the pipette tip coupler moved into the tip a further amount with the tip being lifted up while pushing down on the squeeze ring for defining a second or subsequent state of squeezing the primary O-ring to a second or subsequent compressed and extruded state.

FIG. 24 is a longitudinal sectional, side elevational, fragmented detailed view of the primary O-ring in the subsequent compressed and extruded state as is illustrated in FIG. 23.

FIG. 25 is a longitudinal sectional, side elevational, fragmented detailed view of the secondary O-ring in a second or subsequent compressed state against the tip sealing seat or surface as is illustrated in FIG. 23.

Figure 1:
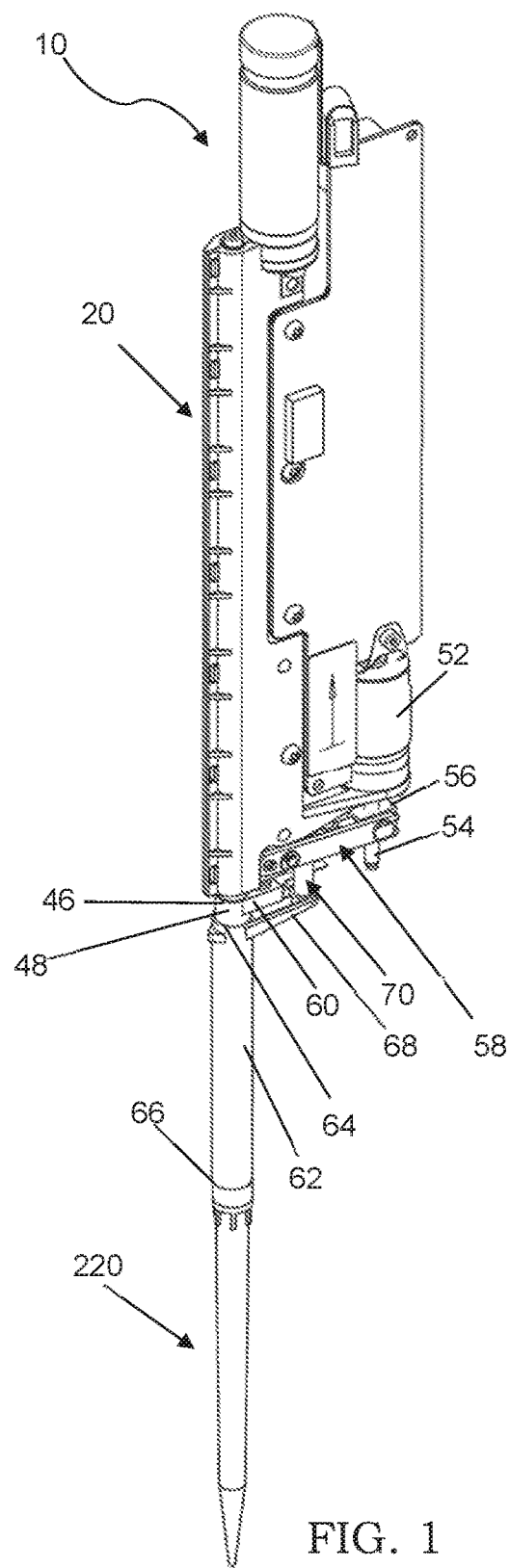
FIG. 1 is a perspective view of an example embodiment of an air displacement pipette device assembly of an automated liquid handling system.

Although various example embodiments may be numbered herein, these embodiments should not be limited by these terms. These terms are only used to distinguish one embodiment from another. Additionally, these terms do not imply a sequence or order.

DETAILED DESCRIPTION

For the purpose of illustrating the disclosure, there are shown in the drawings embodiments which are presently preferred. These example embodiments will now be described more fully with reference to the accompanying drawings wherein like reference numerals are used to denote like parts or portions throughout the description of the several views of the drawings.

Pipette Device Assembly with Pipette Tip Coupler and Disposable Pipette Tip

FIG. 1 illustrates an example embodiment of a pipette device assembly 10 comprising an example embodiment of a pipette device 20, an example embodiment of a pipette tip coupler device 100 (FIG. 2), and an example embodiment of a disposable pipette tip 220 removably coupled to the pipette device 20 by way of the pipette tip coupler 100.

Pipette Device 20

Figure 2:
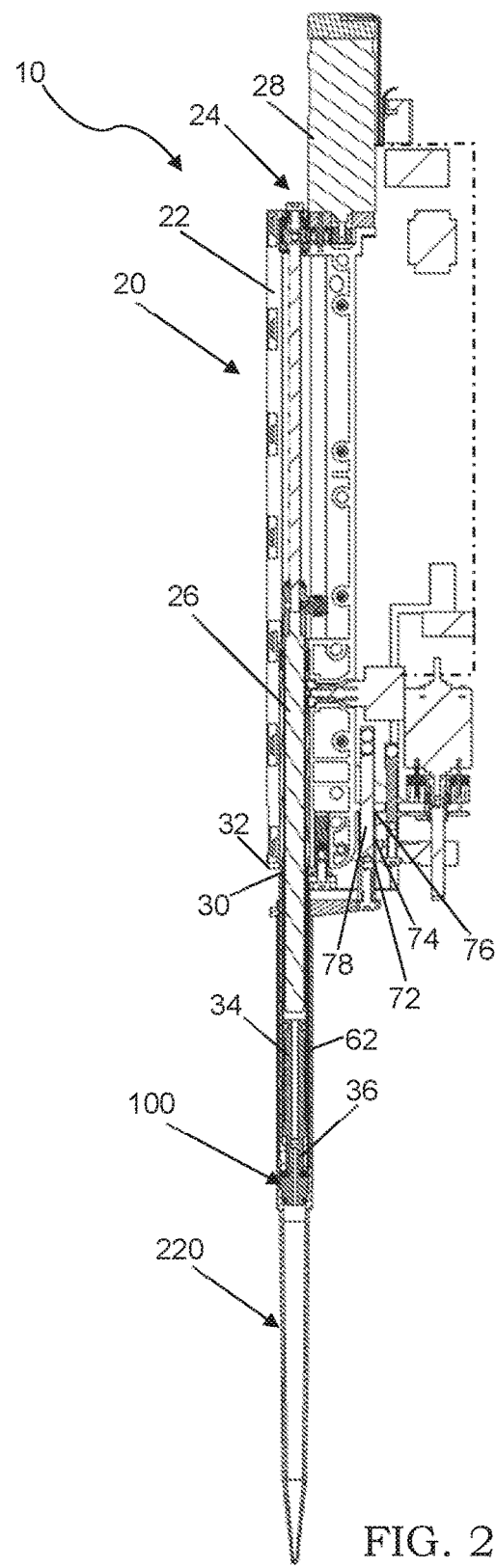
FIG. 2 is a longitudinal sectional, side elevational view of the example embodiment of the pipette device assembly.

Referring to FIG. 2, and in one example embodiment, the pipette device 20 comprises a body 22 supporting an aspirating and dispensing device 24 comprising a plunger 26 operatively coupled to and driven by a motor 28. The plunger 26 resides within a plunger cylinder 30 extending from a distal or lower end 32 of the body 22 of the pipette device 20. Pipette device 20 further comprises an aspirating and dispensing cylinder 34 that is at least partially disposed within plunger cylinder 30 at a location axially aligned with and distally below the plunger 26. The aspirating and dispensing cylinder 34 terminates to a distal mounting flange 36 for attaching with the pipette tip coupler 100 which, in turn, removably couples with the disposable pipette tip 220.

Figure 3:
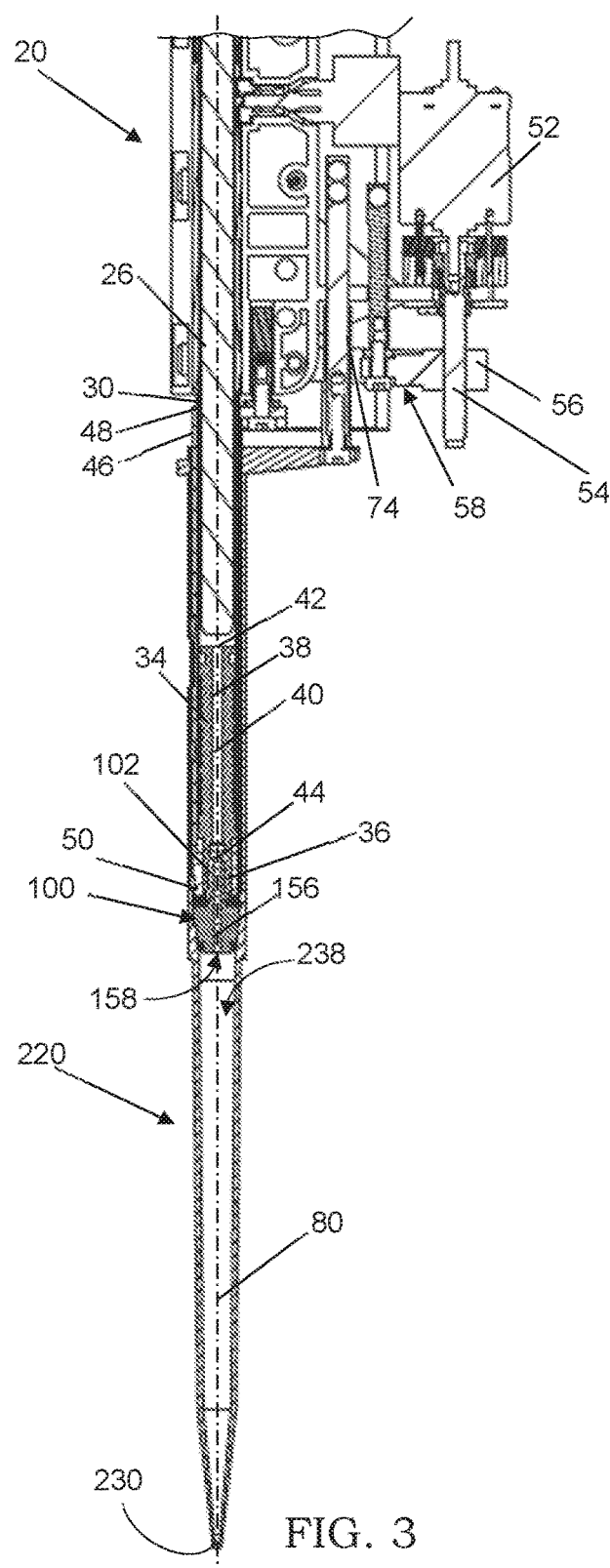
FIG. 3 is a fragmentary longitudinal sectional, side elevational view of the example embodiment of the pipette device assembly comprising a pipette device operatively coupled to a first example embodiment of a pipette tip coupler and a disposable pipette tip in combination.

As illustrated in FIG. 3, the aspirating and dispensing cylinder 34 further comprises an interior circumscribing side wall 38 that defines an open-ended pipette channel 40 extending therethrough. The open ended pipette channel 40 longitudinally extends along a longitudinal channel axis 80 of the pipette device assembly 10 (FIG. 1) between an open upper end portion 42 and open lower end portion 44 of the aspirating and dispensing cylinder 34 for providing open communication between plunger 26 and an exterior area adjacent distal mounting flange 36 wherein the distal mounting flange 36 is operatively connected to the pipette tip coupler 100 comprising an open ended cylindrically shaped central channel 158 extending therethrough to provide open communication between the passage opening 238 of the tip 220 and the aspirating and dispensing cylinder 34 via the pipette tip coupler 100.

Piston or Squeeze Sleeve 46

Referring to FIG. 3, the pipette device 20 further comprises a hollow piston or squeeze sleeve 46 having a proximal or upper end 48 and a distal or lower end 50. The squeeze sleeve 46 circumscribes both the plunger cylinder 30 and the aspirating and dispensing cylinder 34 and is operatively coupled to a squeeze motor 52.

Figure 4:
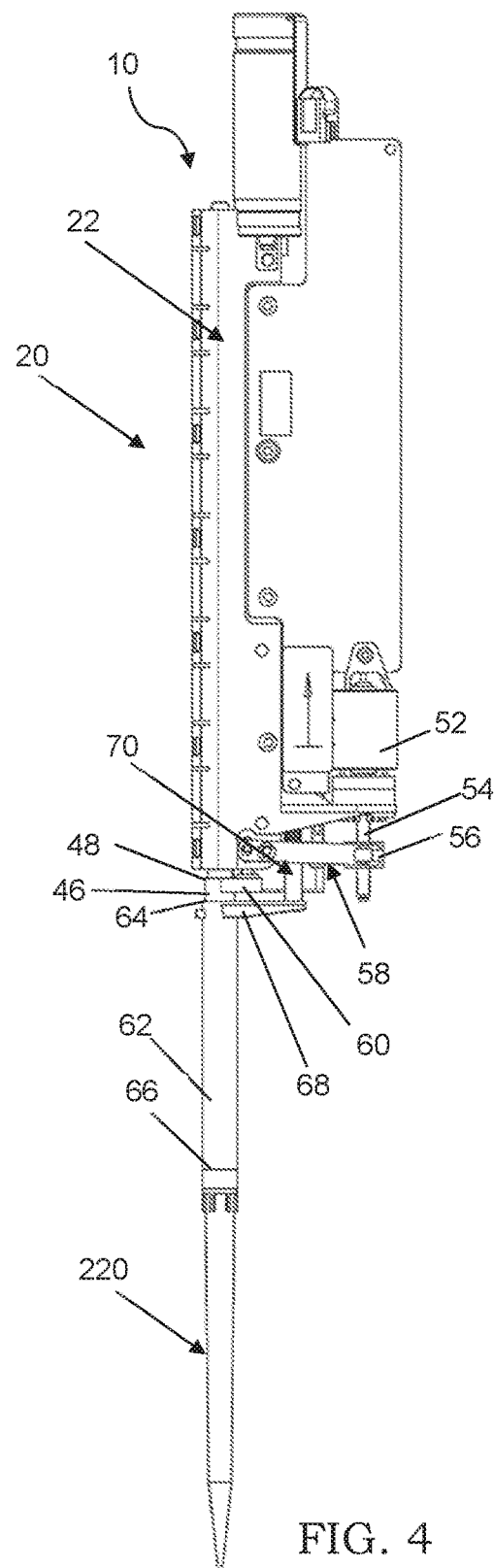
FIG. 4 is a side elevational view of the example embodiment of the pipette device assembly.

As illustrated in FIG. 4, the squeeze motor 52 of pipette device assembly 10 is supported on the body 22 of the device 20 and is operatively coupled to and drives a lead screw 54 that couples to an axially translating lead nut 56 that is operatively coupled to a squeeze linkage 58. Additionally, the squeeze linkage 58 is operatively coupled to the proximal or upper end 48 of squeeze sleeve 46 via squeeze linkage arm 60 such that rotation of the squeeze motor 52 in a first direction results in linear axial translation of squeeze sleeve 46 in a distal or vertically downward direction along longitudinal channel axis 80 (FIG. 3) to contact and push on an annular wedge or squeeze ring 200 (FIG. 5) of the coupler 100 as described below. Furthermore, subsequent rotation of the squeeze motor 52 in a second or opposite direction results in linear counter axial translation of the squeeze sleeve 46 in a proximal or vertically upward direction opposite the distal or vertically downward direction along longitudinal channel axis 80 (FIG. 3).

Ejection Sleeve 62

Referring to FIG. 4, the pipette device 20 further comprises an ejection sleeve 62 used to eject the disposable pipette tip 220 from the pipette device 20 wherein the ejection sleeve 62 is axially movable relative to the aspirating and dispensing cylinder 34 (FIG. 2) and comprises a proximal or upper end 64, a distal or lower end 66, and an ejection sleeve arm 68 attached at a first end to the ejection sleeve 62 adjacent upper end 64 and having an opposing second end attached to a first end of a plunger device 70.

Figure 5:
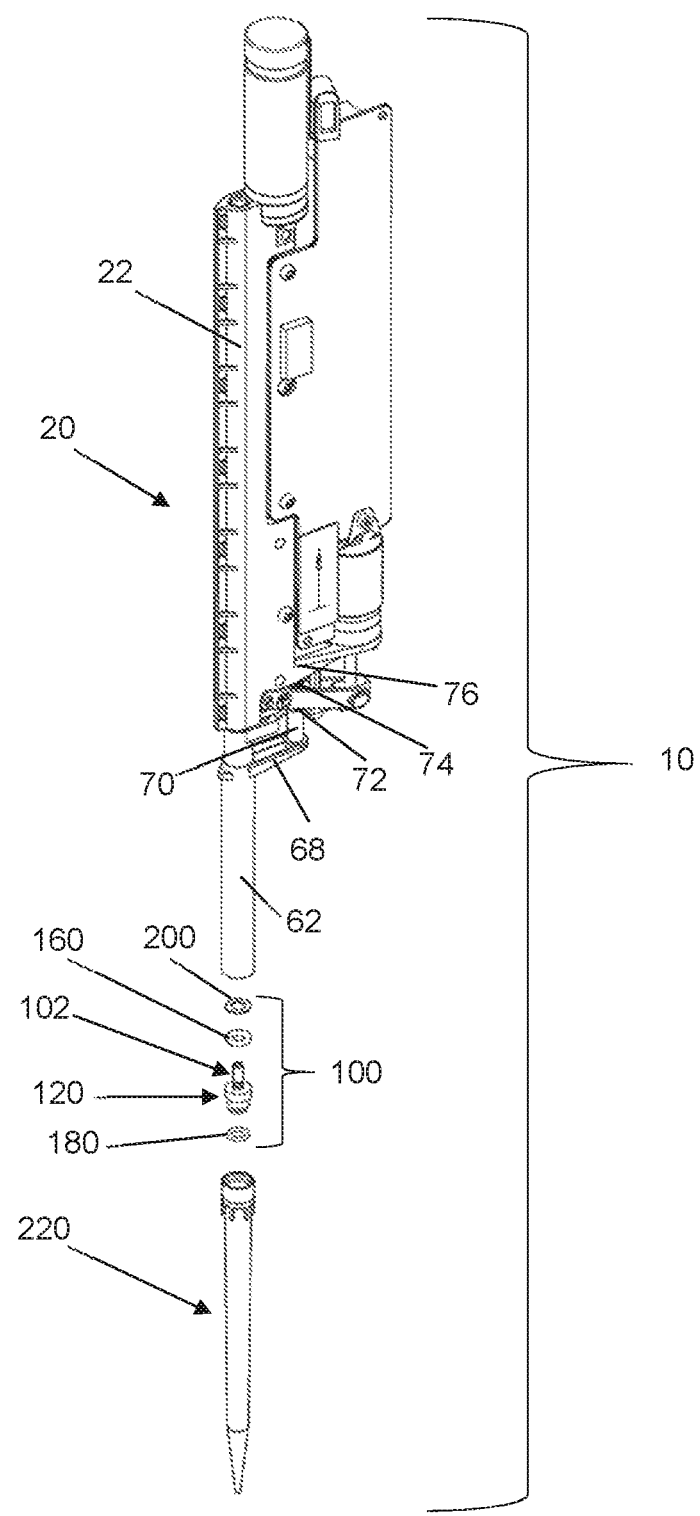
FIG. 5 is a partial exploded parts perspective view of the example embodiment of the pipette device assembly detailing parts of the first example embodiment of the pipette tip coupler interposed between the disposable pipette tip and the pipette device.

As illustrated in FIG. 5, the plunger device 70 comprises an opposing end surface 72 abutting one end of an ejection sleeve spring 74 having an opposing spring end abutting against an upper surface portion 76 of the body 22 of device 20 wherein the ejection sleeve spring 74 is captured between the surfaces 72, 76 to be spring loaded to bias the plunger device 70 and attached sleeve 62 in a normally pipette tip ejected state.

FIG. 2 illustrates the retracted state of the ejection sleeve 62. The normally pipette tip ejected state is configured to require a force, such as coupling to pipette tip 220, to overcome the ejection sleeve spring force in order to axially push the ejection sleeve 62 to a retracted state as illustrated in FIG. 2. Additionally, FIG. 2 illustrates that the spring 74 circumscribes a central spring guide member 78 to retain the shape of the spring 74 and to preclude the spring 74 from buckling.

Furthermore, and referring to FIG. 5, the spring 74 is dimensioned in such a way that the force exerted on the pipette tip 220 by sleeve 62 in the course of its relaxation is sufficient to assist in ejecting the tip 220 from the pipette tip coupler 100.

It should be appreciated that the pipette tip coupler device 100 (and coupler devices 400 and 500 detailed below) and the disposable pipette tip 220 can be practiced on other embodiments of pipette devices wherein the embodiment of pipette device 20 is provided by way of example only and not limitation.

Pipette Tip Coupler Device 100

Figure 6:
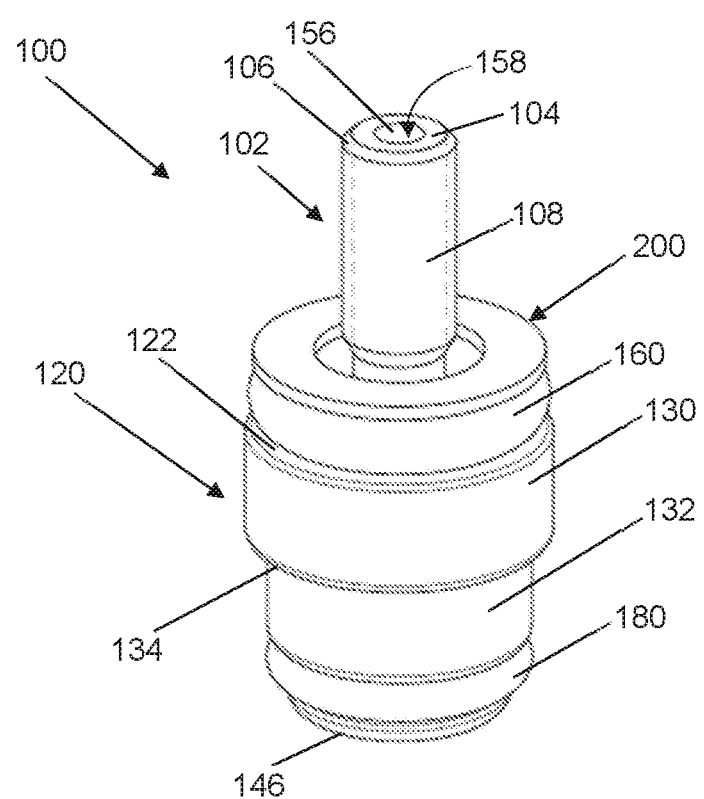
FIG. 6 is a top and side perspective view of the first example embodiment of the pipette tip coupler.
Figure 8:
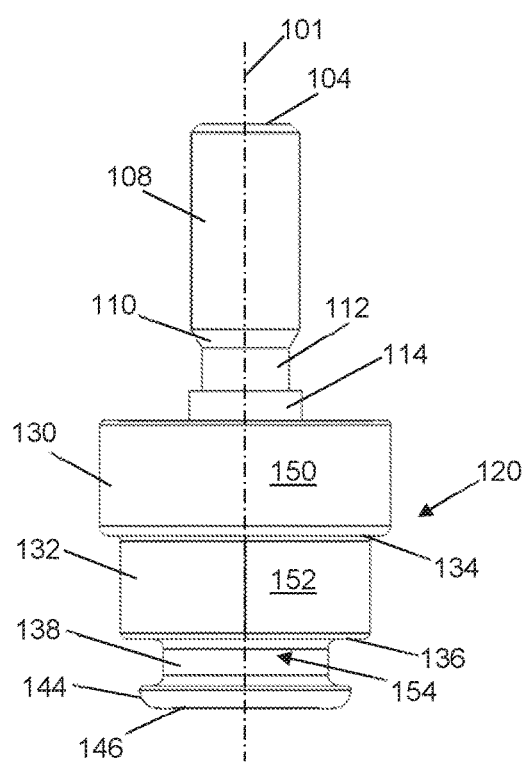
FIG. 8 is a side elevational view of the pipette tip coupler body member.

Referring to FIG. 6, and in one example embodiment, the pipette tip coupler device 100 comprises an elongated head or shank member 102 surmounting a pipette tip coupler body member 120 terminating to a distal stem portion 138 (FIG. 8). Additionally, the pipette tip coupler 100 comprises a primary, upper, or proximal elastomeric element 160 carried at a proximate or upper end portion of the pipette tip coupler body 120. Pipette tip coupler 100 further comprises a squeeze member in the form of, but not limited to, an annular planar squeeze ring 200 surmounting the primary elastomeric member 160 such that the primary elastomeric member 160 is interposed between the pipette tip coupler body 120 and the squeeze member in the form of, but not limited to, annular planar squeeze ring 200. Moreover, the pipette tip coupler 100 comprises a secondary, lower, or distal elastomeric element 180 carried by distal stem portion 138 (FIG. 8).

Shank Member 102

As illustrated in FIG. 3, the shank member 102 of the pipette tip coupler 100 is fitted in the distal mounting flange 36 of the aspirating and dispensing cylinder 34 for operatively coupling the pipette tip coupler 100 to the pipette device 20 of the pipette device assembly 10 (FIG. 1).

Figure 7:
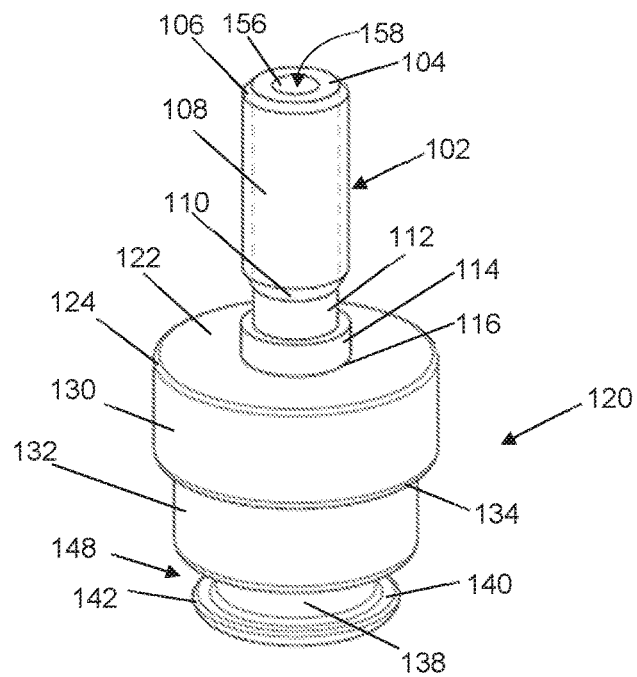
FIG. 7 is a top and side perspective view of an example embodiment of a pipette tip coupler body member of the first example embodiment of the pipette tip coupler.

More particularly, and referring to FIG. 7, the shank member 102 comprises an annular proximal end face 104 defining a proximal or upper end face of the pipette tip coupler 100 (FIG. 6). Annular proximal end face 104 comprises an outer periphery 106 that can be chamfered and that transitions into an elongated tubular body 108. In one embodiment, the elongated tubular body 108 of the shank member 102 can be threaded to mount into distal mounting flange 36 (FIG. 3) which can be threaded with a mating female thread. Distal from annular proximal end face 104, the elongated tubular body 108 transitions into an annular tapered portion 110 that decreases in diameter and transitions into a cylindrical neck portion 112. The cylindrical neck portion 112 distally transitions into a cylindrical collar 114 that has a diameter greater than a diameter of the cylindrical neck portion 112. The cylindrical collar 114 distally terminates to a distal end 116 that defines the distal end of the shank member 102 that surmounts the pipette tip coupler body 120.

Pipette Tip Coupler Body 120

As illustrated in FIG. 7, the pipette tip coupler body 120 comprises a superior, proximal, or upper end surface 122 radially outwardly extending from the distal end 116 of the cylindrical collar 114 and transitioning into an outer peripheral edge 124 that is rounded. In one example embodiment, the upper circular body end surface 122 is substantially planar surface that radially outwardly extends from the distal end 116 of the cylindrical collar 114 to the outer peripheral edge 124.

As also illustrated in FIG. 7, the pipette tip coupler body 120 comprises a multi cylindrical section comprising a first cylindrical portion or stop disk portion 130 that distally extends axially away from the upper end surface 122 and that is distally followed by a second cylindrical portion 132 that is reduced in diameter for forming a distally facing axial shoulder surface or stop shoulder surface 134 between the adjoining first and second cylindrical portions 130, 132 wherein an embodiment of the surface 134 is substantially perpendicular to a longitudinal central axis 101 (FIG. 8) of the pipette tip coupler body 120.

As illustrated in FIG. 8, the second cylindrical portion 132 distally extends from the stop shoulder surface 134 to a distally lower under surface 136 that radially inwardly transitions into a reduced diameter distal cylindrical stem portion 138. As illustrated in FIG. 7, the distal cylindrical stem portion 138 terminates to a radially outwardly extending upper surface 140 of a generally round end plate 142 which comprises a rounded peripheral edge 144 (FIG. 8) that provides a circumferential rounded transition between the upper surface 140 of the generally round end plate 142 and a lower generally planar surface 146 (FIG. 8) of the generally round end plate 142 defining the distal end face of the pipette tip coupler body 120 of pipette tip coupler 100 illustrated in FIG. 6.

Referring to FIGS. 7 and 8, and as noted above, the first cylindrical portion 130 comprises the first diameter that is greater than the second diameter of the second cylindrical portion 132 for forming the axial shoulder surface or stop shoulder surface 134 between the first and second cylindrical portions 130, 132. Additionally, and as illustrated in FIG. 7, the second diameter of the second cylindrical portion 132 is greater than a diameter of the generally round end plate 142. Furthermore, a diameter of the distal cylindrical stem portion 138 is less than both the second diameter of the second cylindrical portion 132 and the diameter of the generally round end plate 142 for defining a lower, distal groove 148 between the second cylindrical portion 132 and the generally round end plate 142 as illustrated in FIG. 7.

As illustrated in FIG. 8, and in one example embodiment, the first and second cylindrical head portions 130 and 132 respectively comprise generally smooth exterior cylindrical surfaces 150, 152 and the distal cylindrical stem portion 138 comprises a generally smooth exterior cylindrical surface or groove surface 154.

As further illustrated in FIG. 7, the pipette tip coupler body 120 further comprises the open ended, interior cylindrical channel surface 156 that defines the open ended cylindrically shaped central channel 158 illustrated in FIG. 3. The central channel 158 runs along the longitudinal central axis 101 (FIG. 8) of the pipette tip coupler body 120 from the annular proximal end face 104 to the lower generally planar surface 146, which respectively define the proximal and distal end faces of the pipette tip coupler 100 illustrated in FIG. 6. Accordingly, and as also noted above, the open ended cylindrically shaped central channel 158 provides open communication between the aspirating and dispensing cylinder 34 and the pipette tip 220 wherein the aspirating and dispensing cylinder 34 is also in open communication with the aspirating and dispensing plunger 26.

Primary Elastomeric Element 160

Figure 9:
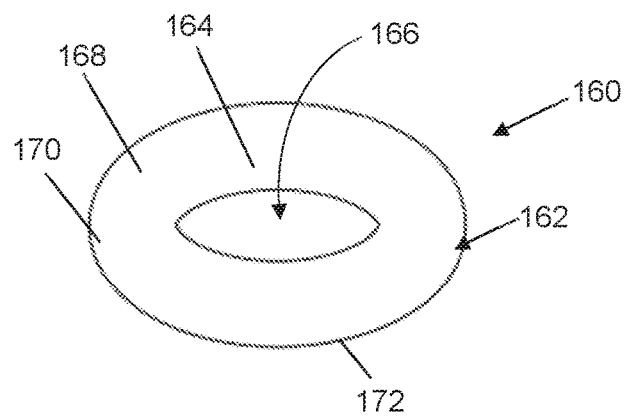
FIG. 9 is a top and side perspective view of an example embodiment of an upper or primary elastomeric element or O-ring of the first example embodiment of the pipette tip coupler.

FIG. 9 illustrates one example embodiment of the primary elastomeric element 160 that is carried, as illustrated in FIG. 6, at the proximate end portion of coupler body 120 of the pipette tip coupler 100.

As illustrated in FIG. 9, the primary elastomeric element 160 is in the form of, but not limited to, an O-ring comprising an annular body 162 having an interior surface 164 defining a central opening 166, a top surface 168, a peripheral exterior surface 170, and a bottom surface 172.

Figure 12:
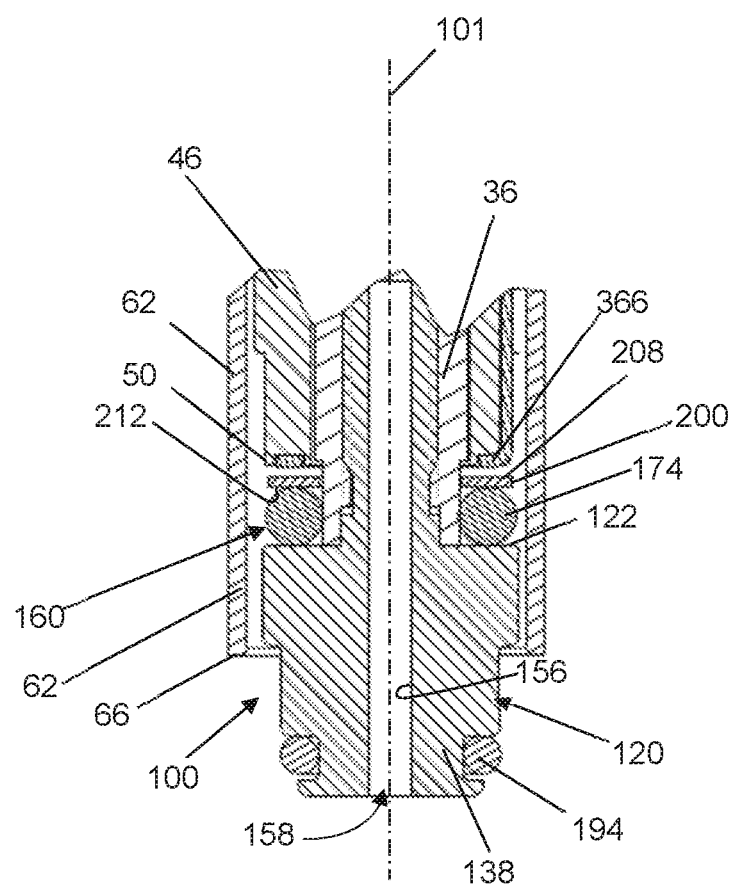
FIG. 12 is a fragmentary, longitudinal sectional, side elevational view of the example embodiment of the pipette device operatively coupled to the first example embodiment of the pipette tip coupler.

Referring to FIGS. 9 and 12, the central opening 166 of the upper elastomeric element 160 is dimensioned to allow the distal mounting flange 36, with the pipette tip coupler 100 fitted therein, to pass through the central opening 166 so as to allow a seating abutment of at least the bottom surface 172 of the upper elastomeric element 160 with the upper end surface 122 of the pipette tip coupler body 120 wherein the pipette tip coupler body 120 carries the upper elastomeric element 160 on the upper end surface 122 in the form of, but not limited to, the planar end surface described above. In a relaxed or unsqueezed state, the upper elastomeric element 160 comprises a circumferentially continuous, generally circular cross sectional area 174 as illustrated in FIG. 12.

Secondary Elastomeric Element 180

Figure 10:
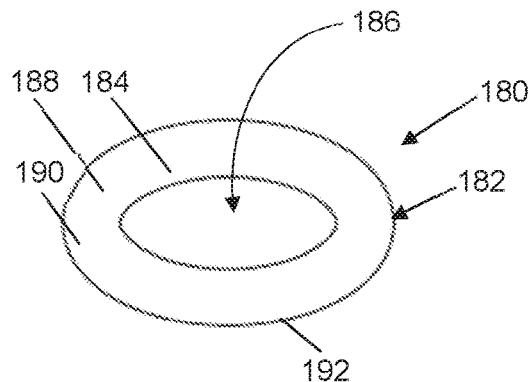
FIG. 10 is a top and side perspective view of an example embodiment of a lower elastomeric element or O-ring of the first example embodiment of the pipette tip coupler.

FIG. 10 illustrates one example embodiment of secondary or distal elastomeric element 180 that is carried, as illustrated in FIG. 6, at the distal end portion of coupler body 120 of the pipette tip coupler 100. Accordingly, the pipette tip coupler body 120 carries the secondary or distal elastomeric element 180 axially distally spaced from the primary or upper elastomeric element 160 by way of the distal cylindrical stem portion 138.

As illustrated in FIG. 10, the secondary or distal elastomeric element 180 is in the form of, but not limited to, an O-ring comprising an annular body 182 having an interior surface 184 defining a central opening 186, a top surface 188, a peripheral exterior surface 190, and a bottom surface 192. In a relaxed or unsqueezed state, the lower elastomeric element 180 comprises a circumferentially continuous, generally circular cross sectional area 194 as is illustrated in FIG. 12.

Referring to FIGS. 10 and 12, the central opening 186 of the lower elastomeric element 180 is dimensioned to closely or tightly circumscribe the distal cylindrical stem portion 138 of the pipette tip coupler 100 and allow a seating abutment between the lower elastomeric element 180 and the distally lower under surface 136 (FIG. 8) of the of the second cylindrical portion 132 (FIG. 8) of the pipette tip coupler body member 120 wherein surface 136 is in the form of, but not limited to, a planar, conical or concaved configuration.

Annular Planar Squeeze Ring 200

As illustrated in FIG. 6, and as noted above, one example embodiment of the pipette tip coupler 100 further comprises the squeeze member in the form of, but not limited to, the annular planar squeeze ring 200 surmounting the upper elastomeric element 160 such that the upper elastomeric element 160 is interposed between the first cylindrical portion or stop disk portion 130 of the pipette tip coupler body 120 and the annular planar squeeze ring 200.

Figure 11:
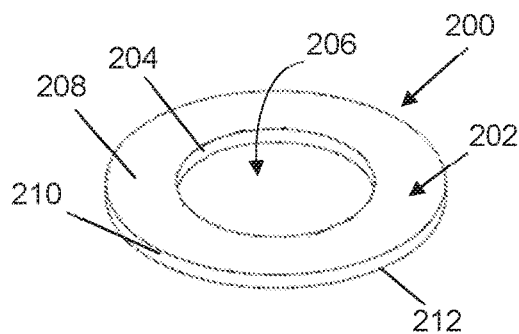
FIG. 11 is a top and side perspective view of an example embodiment of a squeeze member in the form of an annular planar squeeze ring of the first example embodiment of the pipette tip coupler.

In one example embodiment, and referring to FIG. 11, the annular planar squeeze ring 200 comprises a resilient planar annular body 202 having an interior circular surface 204 defining a central opening 206, a top planar surface 208, a circular peripheral edge 210, and a bottom planar surface 212.

Referring to FIGS. 11 and 12, the central opening 206 of the annular planar squeeze ring 200 is dimensioned to allow the distal mounting flange 36, with the pipette tip coupler 100 fitted therein, to pass through the central opening 206 of the annular planar squeeze ring 200 so as to allow a seating abutment of the bottom planar surface 212 of ring 200 with the top surface 168 (FIG. 9) of the primary or upper elastomeric member 160. As illustrated in FIG. 12, the top planar surface 208 of the annular squeeze ring 200 is initially spaced from the distal end 50 of the squeeze piston 46 in a home position such that the upper elastomeric element 160 is in the relaxed or unsqueezed state.

Motor Actuation

Figure 26:
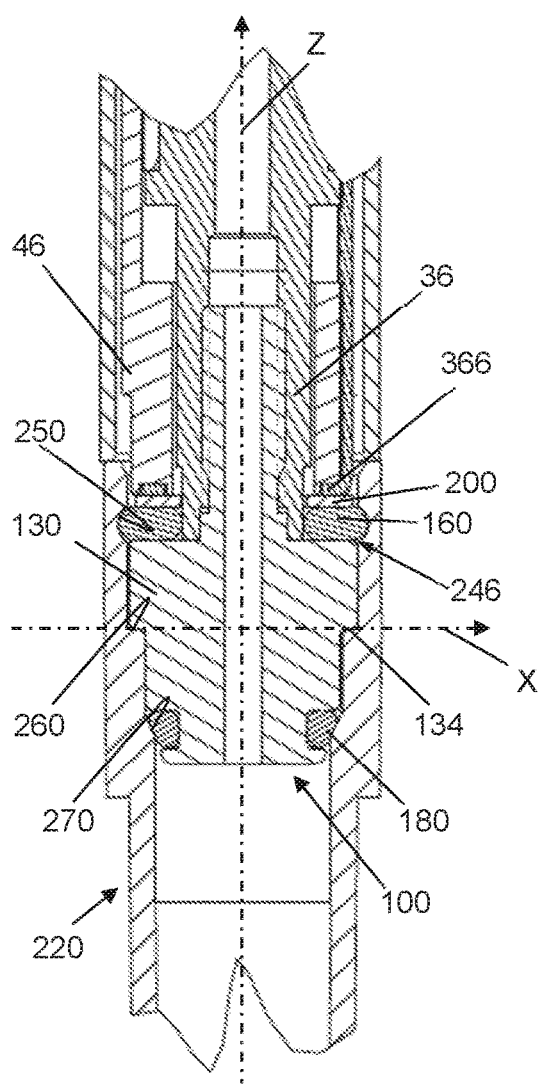
FIG. 26 is a fragmentary, longitudinal sectional, side elevational view of the first example embodiment of the pipette tip coupler moved into the example embodiment of the disposable pipette tip to a final amount with the tip being lifted up to its final seated state to engage the coupler by the method of moving the squeeze ring into its final position thereby defining a final state of coupling with the distal elastomeric element or O-ring in a final compressed and seated sealing state.

With the pipette tip coupler device 100 fitted to the distal mounting flange 36 as illustrated in FIG. 12, the top planar circular surface 208 of the annular squeeze ring 200 is adjacent the distal end 50 of the squeeze sleeve 46. Accordingly, actuation of the squeeze motor 52 (FIG. 1) in a first direction results in linear axial translation of the squeeze sleeve 46 in a distal or vertically downward direction for applying a force axially on the top surface 208 of the annular squeeze ring 200 via an LLD circuit ring end 366 detailed below for forcing the bottom planar surface 212 to push uniformly against the upper elastomeric element 160 for axially squeezing the upper elastomeric element 160 between the bottom planar surface 212 of the annular squeeze ring 200 and the upper end surface 122 of the pipette tip coupler body 120 and into contact with surface 250 of groove 246 of the disposable pipette tip 220 as illustrated in FIG. 26, detailed in FIG. 27, and described below.

Subsequent actuation of the squeeze motor 52 (FIG. 1) in a second direction, opposite the distal or vertically downward direction, returns the distal end 50 of the squeeze sleeve 46 to a home position as illustrated in FIG. 12 such that the annular squeeze ring 200 axially slides up thereby allowing the upper elastomeric element 160 to return to the relaxed or unsqueezed state as illustrated in FIG. 12.

Pipette Tip 220

Figure 13:
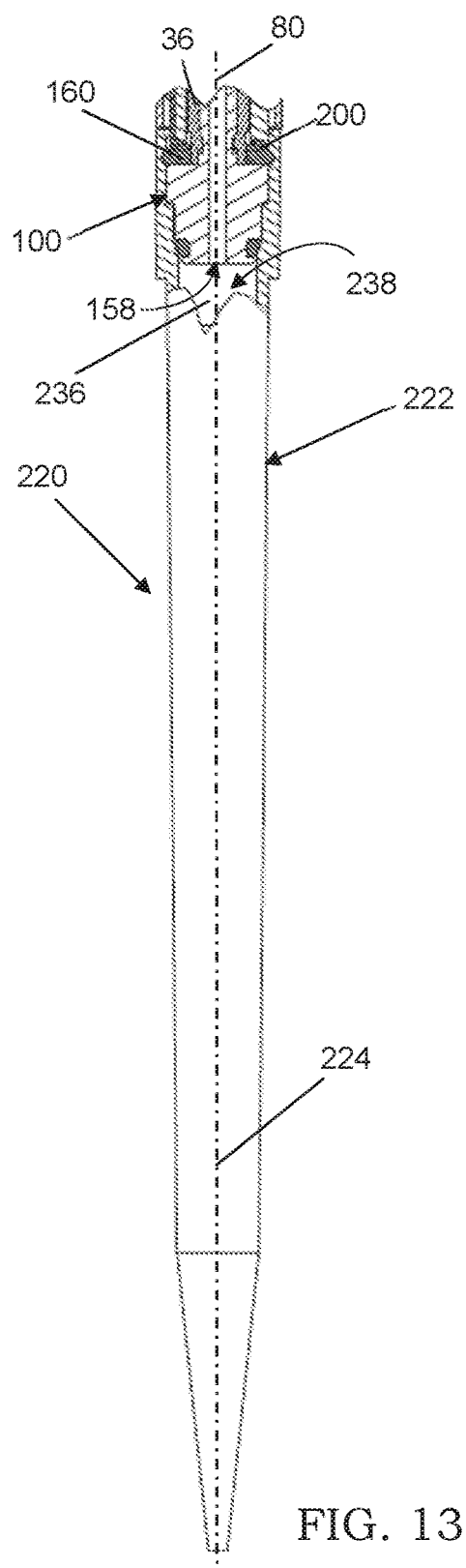
FIG. 13 is a fragmentary, partially sectional, side elevational view of the example embodiment of the pipette device operatively coupled to the first example embodiment of the pipette tip coupler coupled to the disposable pipette tip.

Referring to FIG. 13, and in one example embodiment, the disposable pipette tip 220 comprises an elongated tubular pipette tip body 222 having a central longitudinal axis 224.

Figure 14:
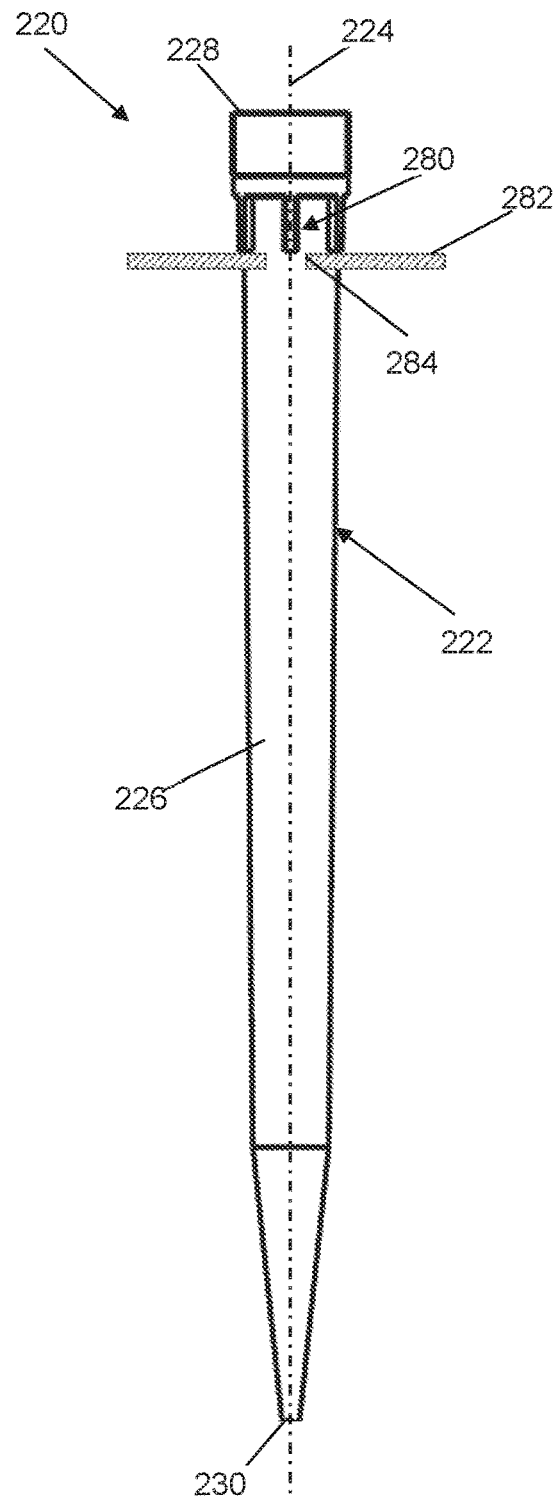
FIG. 14 is a side elevational view of the example embodiment of the disposable pipette tip illustrated in a supported position.
Figure 15:
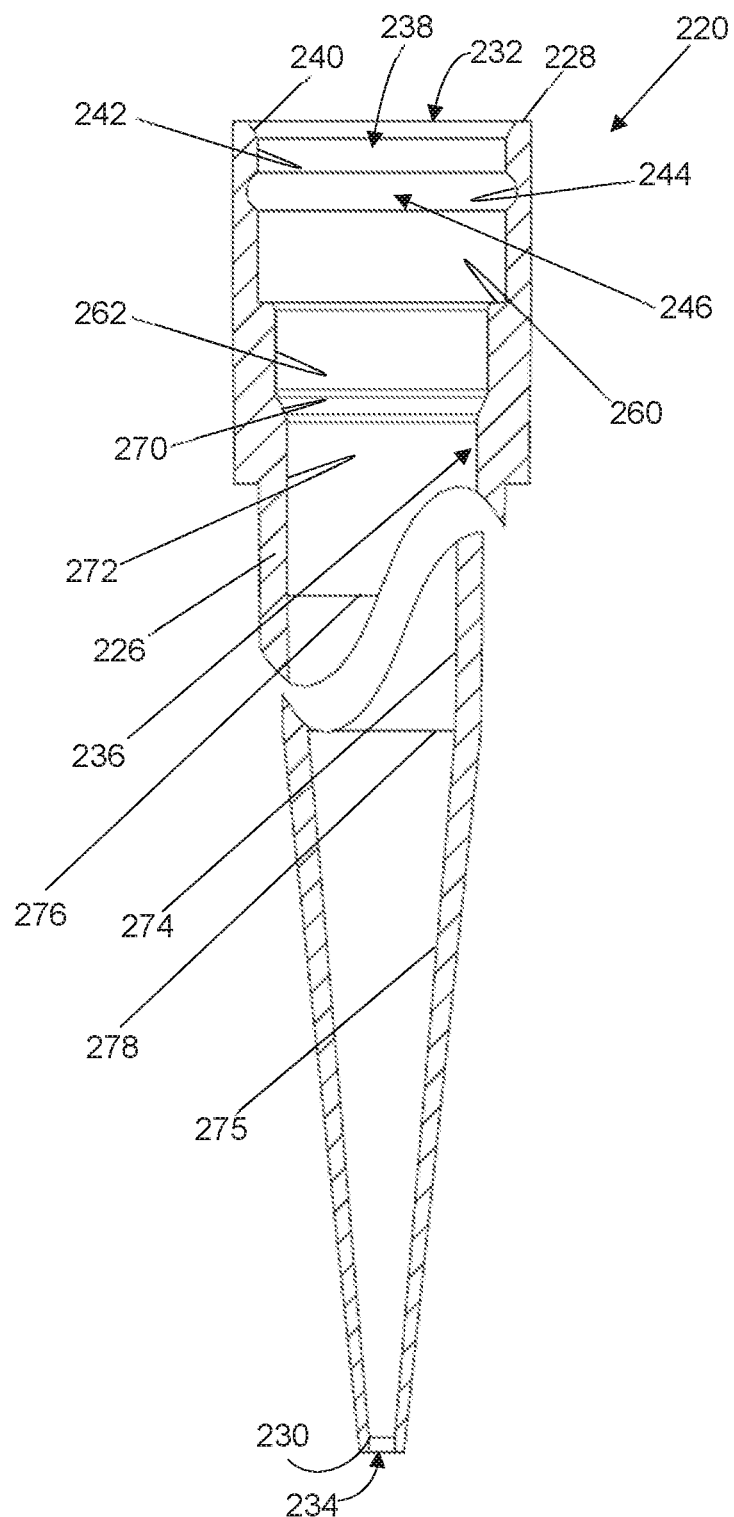
FIG. 15 is a fragmentary, longitudinal sectional, side elevational view detailing the interior of the example embodiment of the disposable pipette tip.

As illustrated in FIG. 14, the pipette tip body 222 comprises an elongated circumscribing sidewall 226 longitudinally extending along the central longitudinal axis 224 between a proximal or upper annular end face 228 and a distal or lower annular end face 230 defining, as illustrated in FIG. 15, circumscribing open proximal and distal annular ends 232 and 234 respectively.

As illustrated in FIG. 13, the elongated circumscribing sidewall 226 (FIG. 14) further comprises an interior surface 236 defining a pipette tip passage opening 238 extending longitudinally along the central longitudinal axis 224 of the pipette tip body 222 between the open upper and lower annular ends 232, 234 illustrated in FIG. 15.

Accordingly, and referring to FIG. 3, the pipette tip passage opening 238 provides open communication from an area exterior to the open distal annular end 234 (FIG. 15), through the pipette tip 220, and to the pipette device channel 40 by way of the central channel 158 of the pipette tip coupler 100 when the pipette tip coupler 100 is coupled between the pipette device 20 and the pipette tip 220. In this configuration, the central longitudinal axis 224 of the pipette tip body 222 of the pipette tip 220 is coextensive with the longitudinal channel axis 80 as is illustrated in FIG. 13.

First Substantially Cylindrical Interior Surface Section

Referring to FIG. 15, and in one example embodiment, the interior surface 236 of the elongated circumscribing sidewall 226 comprises an annular chamfered interior surface 240 that distally extends radially inward from the proximal annular end face 228 of the pipette tip 220 and terminates by transitioning into a first substantially cylindrical interior surface section 242 having a first diameter.

Axially Arcuate Circumferential Surface Defining a Groove

As illustrated in FIG. 15, and in one example embodiment, the first substantially cylindrical interior surface section 242 comprises an axially arcuate circumferential interior surface 244 formed into the elongated circumscribing sidewall 226 defining a circumferential annular groove 246. Annular groove 246 divides the first substantially cylindrical interior surface section 242 into an upper first substantially cylindrical interior surface portion and a lower first substantially cylindrical interior surface portion of substantially equal diameter. Accordingly, the annular groove 246 provides a circumferential radially outwardly extending concavity shaped interior surface interruption of the first substantially cylindrical interior surface section 242 with an arcuate surface longitudinal cross section. The arcuate circumferential interior surface 244 is also configured in alternative surface cross sections as discussed below. And in one embodiment, the first substantially cylindrical interior surface section 242 is devoid of arcuate circumferential interior surface 244 defining the circumferential annular groove 246 as also discussed below.

Figure 16:
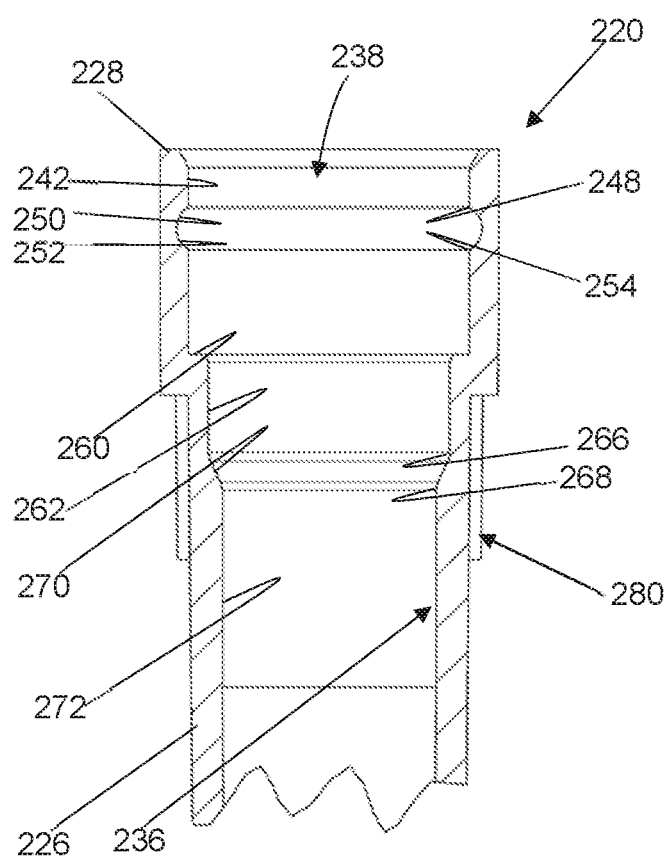
FIG. 16 is an upper detail fragmentary, longitudinal sectional, side elevational view detailing the upper interior of the example embodiment of the disposable pipette tip.

Referring to FIGS. 15 and 16, the axially arcuate circumferential interior surface 244 defining the annular groove 246 comprises an upper annular transition edge 248 distally transitioning into an upper axially arcuate circumferential surface sector portion 250 of the axially arcuate circumferential interior surface 244. In succession, the upper axially arcuate circumferential surface sector portion 250 distally transitions into a lower axially arcuate circumferential surface sector portion 252 of the axially arcuate circumferential surface 244. Then, lower axially arcuate circumferential surface sector portion 252 terminates to a lower annular transition edge 254.

The upper axially arcuate circumferential surface sector portion or upper portion 250 provides the annular groove 246 with an increasing radius relative to the central longitudinal axis 224 of the pipette tip 220 from the upper annular transition edge 248 to a maximum radius of the annular groove 246 relative to the central longitudinal axis 224 that defines a circumferential annular center of the annular groove 246. The lower axially arcuate circumferential surface sector portion or lower portion 252 provides the annular groove 246 with a decreasing radius relative to the central longitudinal axis 224 of the pipette tip 220 from the maximum radius defining the circumferential annular center of the annular groove 246 to the lower annular transition edge 254.

Second Interior Surface Section and Annular Shoulder Stop Surface

As illustrated in FIG. 15, the first substantially cylindrical interior surface section 242 is axially distally proceeded by a second substantially cylindrical interior surface section 262 having a second diameter less than the first diameter of the first substantially cylindrical interior surface section 242 for forming a proximally facing, radially inwardly extending annular shoulder seat surface or stop surface 260 interposed between the first and second substantially cylindrical interior surface sections 242, 262.

In one example embodiment, the proximally facing axial stop surface 260 is substantially planar and generally perpendicular to the central longitudinal axis 224 of the pipette tip body 222 (FIG. 14).

Third Interior Surface Section and Sealing Seat

As illustrated in FIG. 15, the second substantially cylindrical interior surface section 262 is axially distally proceeded by a third substantially cylindrical interior surface section 272 having a third diameter less than the second diameter of section 262. Interposed between the second section 262 and the third section 272 is a frustoconical annular sealing seat or stop surface 270 defining a circumferential radially inwardly angled and distally extending distal working surface 270.

As illustrated in FIG. 16, the frustoconical annular sealing seat surface 270 comprises an upper annular sealing seat edge 266 defining an annular border between the second substantially cylindrical interior surface section 262 and the frustoconical annular sealing seat surface 270. The sealing seat surface 270 further comprises a lower annular sealing seat edge 268 defining an annular border between the frustoconical annular sealing seat surface 270 and the third interior surface section 272 wherein a diameter of the upper annular sealing seat edge 266 is greater than a diameter of the lower annular sealing seat edge 268.

Accordingly, the frustoconical annular sealing seat surface 270 defines the circumferential radially inwardly angled and distally extending distal working surface, abutment, or sealing seat surface 270 interposed between the second substantially cylindrical interior surface section 262 and the third substantially cylindrical interior surface section 272.

As illustrated, the sealing seat surface 270 is disposed at an acute angle relative to the central longitudinal axis 224 (FIG. 14) wherein the acute angle defines an acute sealing seat surface angle relative to the central longitudinal axis 224. In one embodiment, the preferred acute sealing seat surface angle relative to the central longitudinal axis 224 is about 15 degrees to about 35 degrees with a preferred angle of about twenty-five degrees.

In one alternative embodiment to the sealing seat surface 270, the pipette tip 220 comprises an alternative sealing seat surface angle of substantially ninety degrees relative to the central longitudinal axis 224 (FIG. 14) of the pipette tip 220. This alternative embodiment is discussed below and illustrated in FIG. 54 wherein the sealing seat surface angle of an alternative sealing seat surface 2270 relative to the illustrated central longitudinal Z-axis is substantially 90 degrees.

Lower Interior Surface Portion

FIG. 15 further illustrates that in succession to the third substantially cylindrical interior surface section 272 is a fourth interior surface section 274 that is distally followed by a fifth interior surface section 275.

In one example embodiment, the fourth interior surface section 274 distally tapers or decreases in diameter from a distal annular end 276 of the third substantially cylindrical interior surface section 272 to a proximal annular end 278 of the fifth interior surface section 275. In turn, the fifth interior surface section 275 distally tapers or decreases in diameter from the proximal annular end 278 of the fifth interior surface section 275 to the open distal annular end 234 of the pipette tip 220 that is intended for immersion. Additionally, and in one example embodiment, the fifth interior surface section 275 has a greater taper than the fourth interior surface section 274.

External Longitudinal Ribs

Referring to FIG. 14, and in one example embodiment, the pipette tip 220 comprises a plurality of circumferential spaced apart longitudinally extending external ribs 280 disposed on the tubular pipette tip body 222 adjacent the periphery of the proximal annular end face 228 and longitudinally extending externally therefrom to an exterior area of the circumscribing sidewall 226 that is adjacent to the third substantially cylindrical interior surface section 272 as illustrated in FIG. 16.

In one example embodiment, and as illustrated in FIG. 14, the plurality of circumferential spaced apart longitudinally extending external ribs 280 may be utilized to provide support for the pipette tip 220 on or in a support surface 282 that the pipette body 222 has passed through via, for example, a support surface aperture opening 284. One example embodiment of the support surface 282 can be in the form of, but not limited to, lab ware in the form of a tip rack as is known in the art, and informed by the present disclosure.

Automated Pipetting Workstation or System 300

Figure 17:
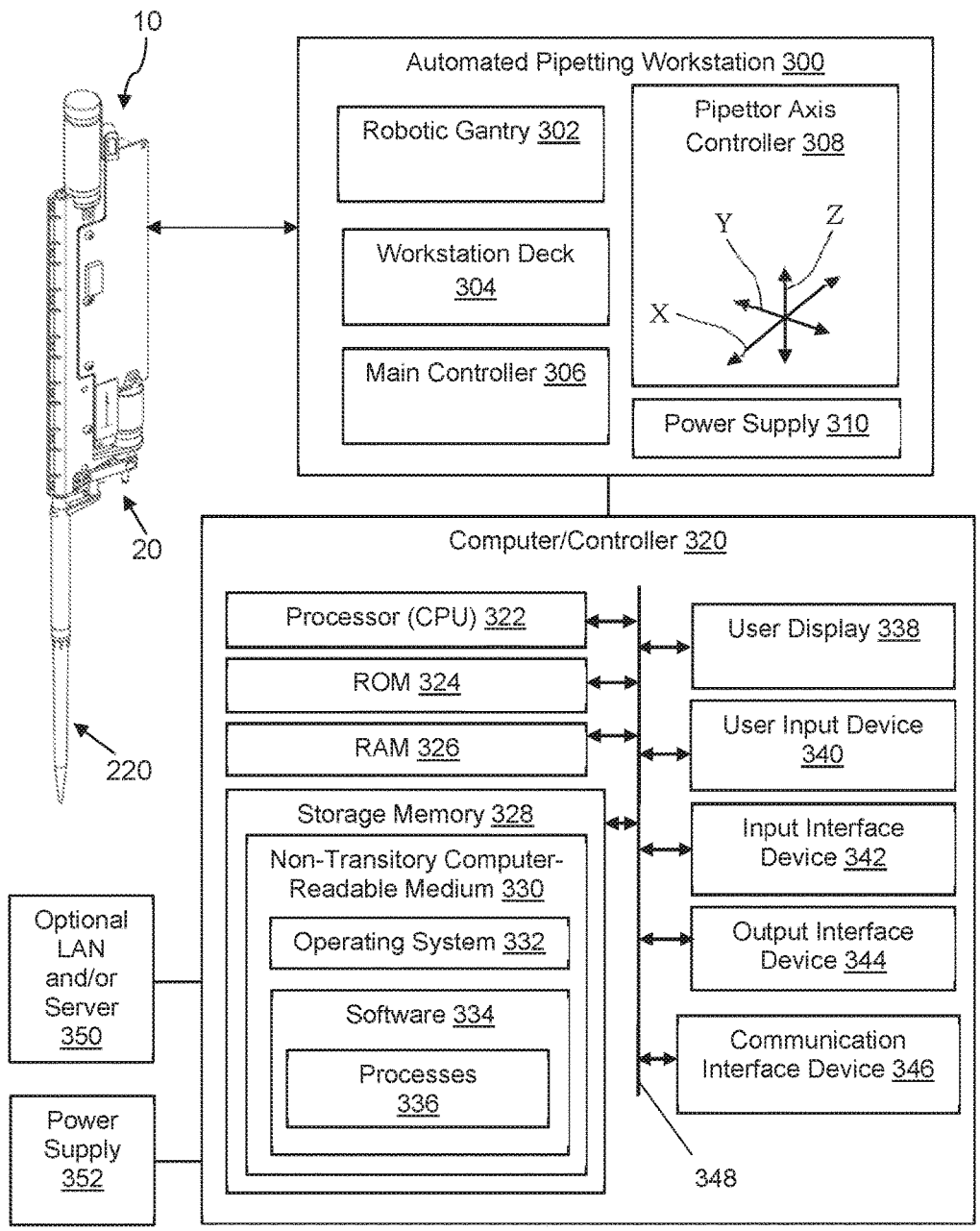
FIG. 17 is a diagrammatical block diagram view of an example embodiment of an automated pipetting workstation or system.

Referring to FIG. 17, and in one example of use and operation, at least one pipette device assembly 10 is employed in an automated pipetting workstation or system 300 that generally provides, but is not limited to, programmed transfers of liquid between containers which comprises mounting and ejection processes of one or more disposable pipette tips 220 to the pipette tip coupler 100 (FIG. 2) operatively carried by the pipette device 20 for carrying out, for example, the programmed transfers of liquid between containers.

The automated pipetting workstation 300 generally comprises a robotic gantry 302 that carries the at least one pipette device assembly 10 vertically above a horizontally disposed workstation deck 304 wherein the pipette device assembly 10 can comprise a single channel pipetting head or a multi-channel pipetting head.

Additionally, the robotic gantry 302 typically provides two or three degrees of freedom wherein three degrees of freedom comprises longitudinal translation along an axis defining an X-axis, latitudinal translation along an axis defining a Y-axis, and vertical (up and down) translation along an axis defining a Z-axis so that the at least one pipette device assembly 10 can move along the length (X-axis) and width (Y-axis) of the deck and vertically up and down (Z-axis) relative thereto. With two degrees of freedom, the robotic gantry is typically provided with the ability to translate the at least one pipette device assembly 10 vertically and either longitudinally or laterally.

In one example embodiment, the automated pipetting workstation 300 further comprises a main controller 306, a pipette axis controller 308, and a power supply 310 that provides power for the main controller 306, the pipette axis controller 308, and at least one pipette device assembly 10.

Additionally, and in one example embodiment, a computer/controller 320 can also be employed with the workstation 300 and communicate with the main controller 306 and the pipette axis controller 308 for controlling the robotic gantry 302 and the at least one pipette device assembly 10 including the associated process protocols of the at least one pipette device assembly 10 such as the disposable pipette tip 220 attaching and ejection (coupling and decoupling) processes detailed below.

In one example embodiment, the computer/controller 320 typically comprises a processor device or central processing unit (CPU) 322, a hardware read only memory device (ROM) 324, a hardware main memory device (RAM) 326, a hardware storage memory 328 comprising a non-transitory computer readable medium or memory 330 having an operating system 332 and software 334 such as user defined processes 336 for the pipette device assembly 10 stored thereby, a user display 338, a user input device 340, an input interface 342, an output interface 344, a communication interface device 346, and a system bus 348 that comprises one or more conductor or communication paths that permit communication among the devices of the computer/controller 320. Computer/controller 320 may also be operatively coupled to LAN and/or server 350. A power supply 352 provides power for the computer/controller 320.

Examples of the above delineated automated pipetting workstation 300 including software are presently manufactured and sold by Hamilton Company, the assignee of the present patent application, located at 4970 Energy Way, Reno, Nev. 89502, United States of America.

Pipette Tip Pickup Process with Pipette Tip Coupler 100

FIGS. 18 through 28 illustrate details of successive stages of an example method of securing attachment of the pipette tip 220 to the pipette tip coupler 100 operatively carried by the pipette device 20. As noted above, and in one example embodiment, the pipette tip 220 may be initially supported for pickup by the support surface 282 disposed on, for example, deck 304.

Figure 18:
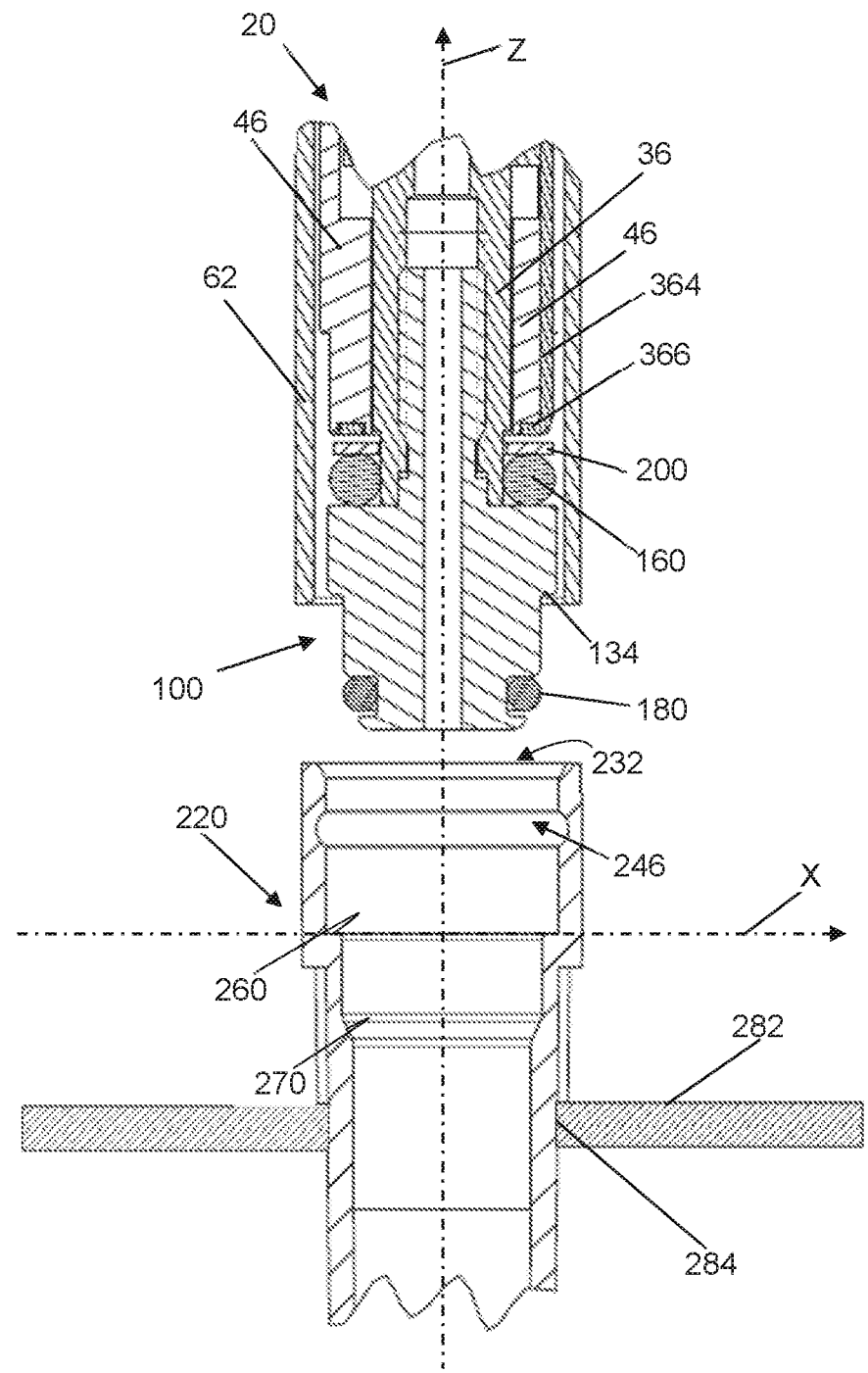
FIG. 18 is a fragmentary, longitudinal sectional, side elevational view of the first example embodiment of the pipette tip coupler axially aligned over the disposable pipette tip.

With the pipette tip coupler 100 connected to the pipette device 20, and upon initialization, the pipette tip coupler 100 is positioned over the open proximal end 232 of the supported pipette tip 220 wherein their respective central longitudinal axes 101 (FIG. 12) and 224 (FIG. 14) are generally aligned along the Z-axis as illustrated in FIG. 18. The eject sleeve 62 is in the eject position, the squeeze piston 46 is in the unsqueezed position, and the primary and secondary O-rings 160, 180 are in the unsqueezed state.

Figure 19:
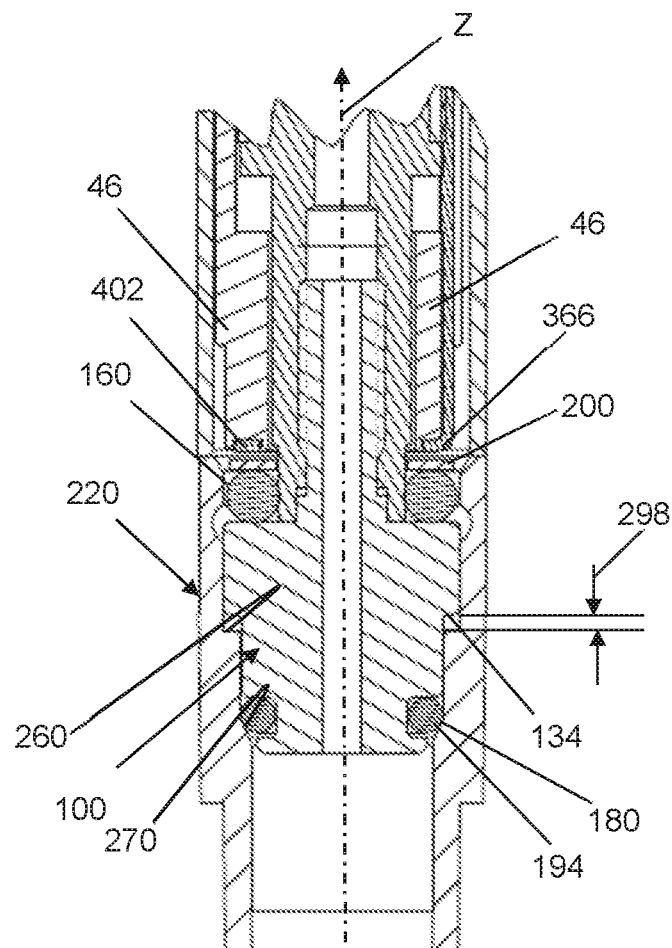
FIG. 19 is a fragmentary, longitudinal sectional, side elevational view of the first example embodiment of the pipette tip coupler axially aligned over and moved into the example embodiment of the disposable pipette tip for defining a stage of coupling of the coupler with the tip to bring the secondary O-ring into contact with a sealing seat or surface while maintaining the primary O-ring in the unsqueezed state such that a gap is maintained between an annular shoulder seat of the disposable pipette tip and a stop shoulder surface of the coupler.

Next, FIG. 19 illustrates the step of the pipette tip coupler 100 being moved down along the Z-axis into the pipette tip 220 and then lowered, causing the distal, elastomeric carrying portions, of the pipette tip coupler 100 to pass into the interior cylindrical proximal end portions of the pipette tip 220 to bring the secondary O-ring 180 into contact with the tip annular sealing seat or stop surface 270 while maintaining the primary O-ring 160 in the unsqueezed state and before the annular shoulder seat or stop surface 260 of the pipette tip 220 and the axial stop shoulder surface 134 of the pipette tip coupler 100 are mated such that a gap 298 is maintained between the annular shoulder seat or stop surface 260 of the pipette tip 220 and the axial stop shoulder surface 134.

Next, FIGS. 20 through 22 illustrate the step of the squeeze sleeve 46 being moved down along the Z-axis and pushing against the LLD circuit ring end 366 which contacts with and pushes against the top surface 208 of the annular squeeze ring 200 having the bottom end 212 surmounting the primary O-ring 160 wherein the primary O-ring 160 starts to be squeezed and subsequently extruded into the groove 246. As illustrated in FIG. 21, and in particular, the primary O-ring 160 is extruded into the groove 246 and into abutment with the upper axially arcuate circumferential surface sector portion 250 of the axially arcuate circumferential interior surface 244 (FIG. 15) defining the groove 246.

Referring to FIG. 20, the action of the primary O-ring 160 extruding into the groove 246 causes an axial upward force that pulls the pipette tip 220 up for starting a process of seating the annular shoulder seat 260 of the pipette tip 220 with the axial stop shoulder surface 134 of the stop disk 130 for closing the gap 298 (FIG. 19) and compressing the secondary O-ring 180 with the frustoconical annular sealing seat 270 of the tip 220.

FIGS. 23 through 25 illustrate a further step of the squeeze piston 46 continuing to move further down along the Z-axis resulting in the annular squeeze ring 200 continuing to push down on and squeeze the primary O-ring 160 for extruding the primary O-ring 160 further into the groove 246 of the pipette tip 220 further closing gap 298 (FIG. 19) and further into abutment with the upper axially arcuate circumferential surface sector portion 250 for pulling the tip axially up along the Z-axis causing the secondary O-ring 180 to be further compressed against annular sealing seat 270 such that its cross-section is no longer circular as illustrated in FIG. 25.

Figure 27:
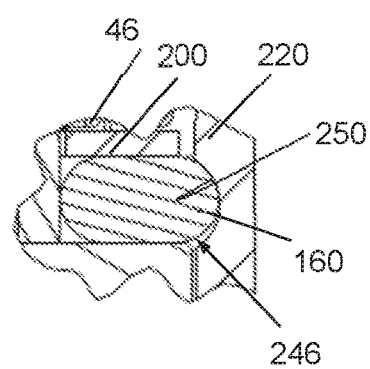
FIG. 27 is a longitudinal sectional, side elevational, fragmented detailed view of the primary O-ring in the final compressed and extruded state as is illustrated in FIG. 26.
Figure 28:
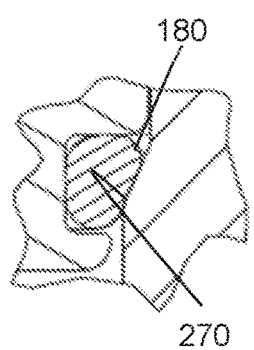
FIG. 28 is a longitudinal sectional, side elevational, fragmented detailed view of the secondary O-ring in the final compressed state against the tip sealing seat or surface as is illustrated in FIG. 26.

FIGS. 26 through 28 illustrate a further step of the squeeze piston 46 being moved down along the Z-axis a pre-calibrated or predetermined length until it is locked in position resulting in the annular squeeze ring 200 being stopped and locked in position by the squeeze piston 46. As a result, the primary O-ring 160 is compressed circumferentially to a desired value for fully seating the axial stop shoulder surface 134 of the pipette tip coupler 100 against the annular shoulder seat surface 260 of the pipette tip 220 with the seating of the two surfaces 134, 260 along an X-axis substantially perpendicular to the Z-axis for forming a normal datum between the X-axis and Z-axis. Concurrently, the secondary O-ring 180 is compressed to a desired value for seating and sealing the secondary O-ring 180 with the annular sealing seat surface 270 of the tip 220 as illustrated in FIG. 28 such that its cross-section is in its final compressed non-circular form. Accordingly, FIGS. 26 through 28 illustrate the completion of the securing attachment process.

Upon completion of the securing attachment process, the primary and secondary elastomeric elements 160, 180 work in combination to produce a fluid-tight seal wherein the first elastomeric element 160 is at least partially seated in the circumferential arcuate interior surface 244 defining the circumferential groove 246 and wherein the second elastomeric element 180 seals against the radially inwardly angled and distally extending surface 270 of the pipette tip 220.

Ejection Process

FIGS. 18 through 28 illustrate, in reverse, details of successive stages of an example method or process of ejecting the pipette tip 220 from the pipette tip coupler 100 operatively carried by the pipette device 20. Thus, the tip ejection process sequence is similar to the attachment or tip pickup securing process sequence detailed above, except in reverse. In one example embodiment, the tip ejection process comprises the steps of: (1) positioning the tip where it is to be discarded, such as a waste container; (2) moving the squeeze piston 46 upward wherein the primary O-ring 160 starts to retract from the groove 246 in the tip 220, secondary O-ring 180 starts to release stored elastic potential energy as a force against the tip, and wherein the spring loaded eject sleeve 62 also pushes against the tip to push it off such that the tip begins to release from the primary O-ring 160 and coupler body member 120; (3) continually moving the squeeze piston 46 upward wherein the primary O-ring 160 continues to retract from the groove 246 in the tip 220 and wherein the secondary O-ring 180 and the spring loaded eject sleeve 62 pushes against the tip 220 to push it off wherein the tip 220 continues to release from the primary O-ring 160 and the coupler body member 120; (4) continually moving the squeeze piston 46 to its upper most position wherein the primary O-ring 160 returns to its original shape and is completely free of the groove 246 in the tip 220 and wherein the secondary O-ring 180 returns to its original shape and the spring loaded eject sleeve 62 pushes against the tip 220 until the tip is pushed off of the coupler body member 120 by the spring loaded eject sleeve 62 and the spring loaded eject sleeve 62 becomes fully extended.

In light of the foregoing, those skilled in the art will appreciate that this tip mounting and ejection processes are applicable to a wide range of mechanically and/or automatically driven pipette types and designs.

Coupling Forces

Figure 29:
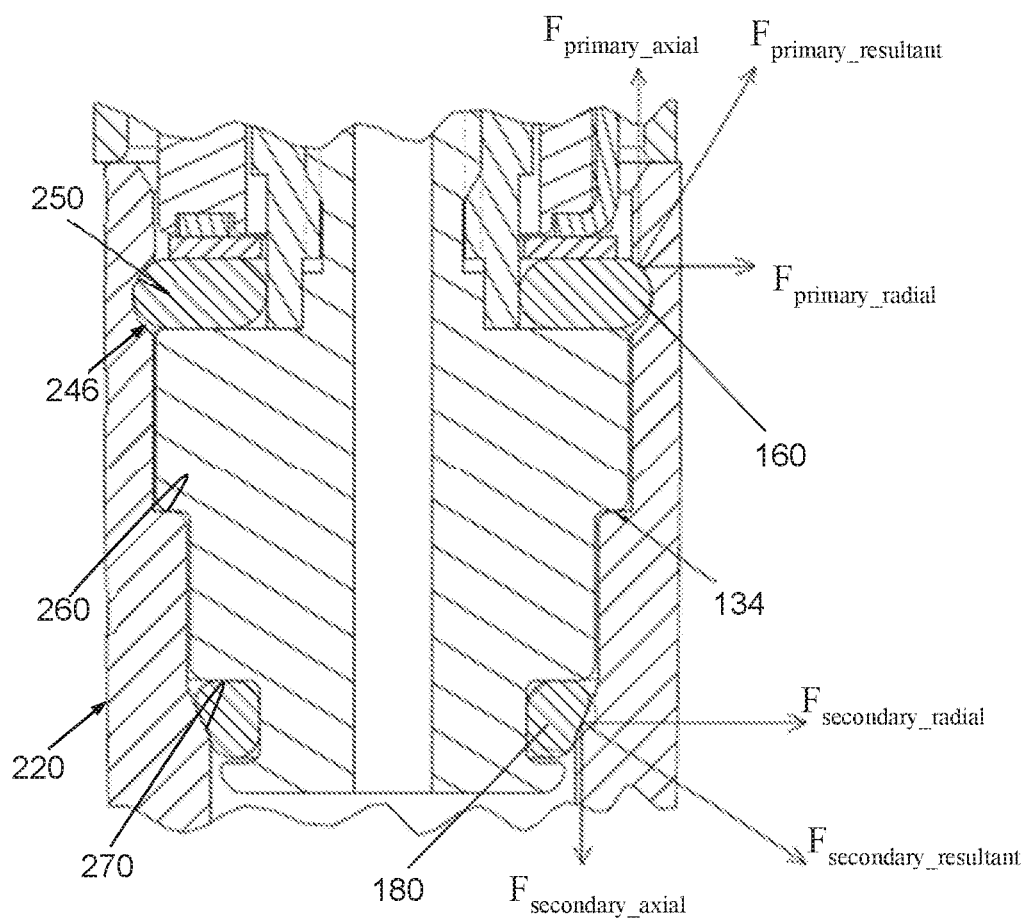
FIG. 29 is a fragmentary, longitudinal sectional, side elevational, detailed view of the completed coupling of the first example embodiment of the pipette tip coupler and disposable pipette tip with associated coupling forces illustrated and identified thereon.

FIG. 29 illustrates a vector diagram of the primary O-ring 160 extruding into the groove 246 and an axial upward force pulling the pipette tip 220 upward wherein the primary O-ring 160 pushes against the upper part 250 (FIG. 27) of the tip groove 246 with a force (Fprimary_resultant) and the secondary O-ring 180 has a force (Fsecondary_resultant) that results from being compressed.

As illustrated in FIG. 29, the primary O-ring force (Fprimary_resultant) is comprised of two components: an axial upward force component (Fprimary_axial) and a radial force component (Fprimary_radial). The primary O-ring axial force component (Fprimary_axial) seats the stop shoulder surface 134 against the axial stop surface 260 of tip 220 and provides the force required to compress the secondary O-ring 180 while the primary O-ring radial force component (Fprimary_radial) provides the radial force needed to seal the primary O-ring 160 against the upper part 250 of the tip groove 246.

As further illustrated in FIG. 29, the secondary O-ring 180 is also comprised of two components: an axial force component (Fsecondary_axial) and a radial force component (Fsecondary_radial).

The secondary O-ring axial force component (Fsecondary_axial) provides a counter force to the primary O-ring axial force component (Fprimary_axial) that benefits the sealing of the primary O-ring 160 by pulling the tip 220 down wherein this pressure further pushes or biases the primary O-ring 160 into the upper corner or upper part 250 of the tip groove 246. The secondary O-ring axial force component (Fsecondary_axial) also provides force to help remove the tip 220 upon ejection.

The secondary O-ring radial force component (Fsecondary_radial) provides the radial force needed to seal the secondary O-ring 180 against the annular sealing seat or stop surface 270 of the tip 220.

The axial shoulder surface 134 of coupler body member 120 and the axial shoulder seat 260 of tip 220 are important for correct tip alignment. Accordingly, and as illustrated in FIG. 29, the coupler 100 and tip 220 are configured so that the primary O-ring axial force pushes the axial shoulder surface 134 and the axial shoulder seat 260 together to preclude misalignment because if the shoulders are not properly mated, especially if they are tilted, a misalignment error (E) is significant as described below.

Misalignment

Figure 30:
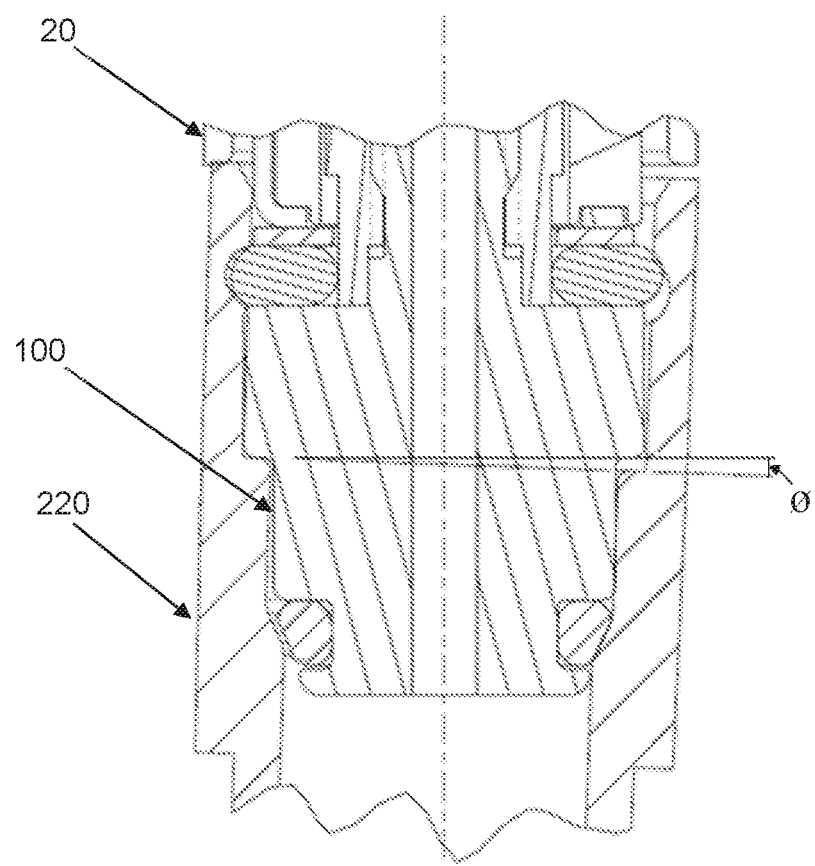
FIG. 30 is a fragmentary, longitudinal sectional, side elevational view of a misaligned coupling between an example embodiment of a pipette tip coupler device and an example embodiment of a disposable pipette tip.
Figure 31:
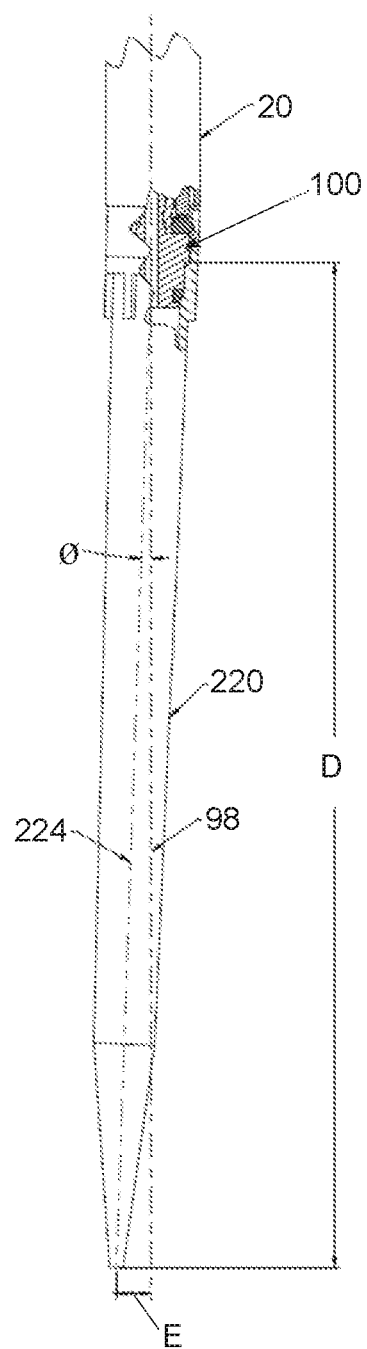
FIG. 31 is a fragmented and cutaway, longitudinal sectional, side elevational view of the misaligned coupling state illustrated in FIG. 30.

Referring to FIGS. 30 and 31, the relationship between the misalignment angle (Ø), the tip axial distance (D) and positional error (E) is: $E = D * TAN(Ø)$. For example, with a misalignment angle (Ø) of two degrees and a tip axial distance of ninety millimeters, the positional error (E) is 3.14 millimeters. This is considered to be very high considering typical positional error tolerances are typically plus or minus 0.5 millimeters.

Alignment

Figure 32:
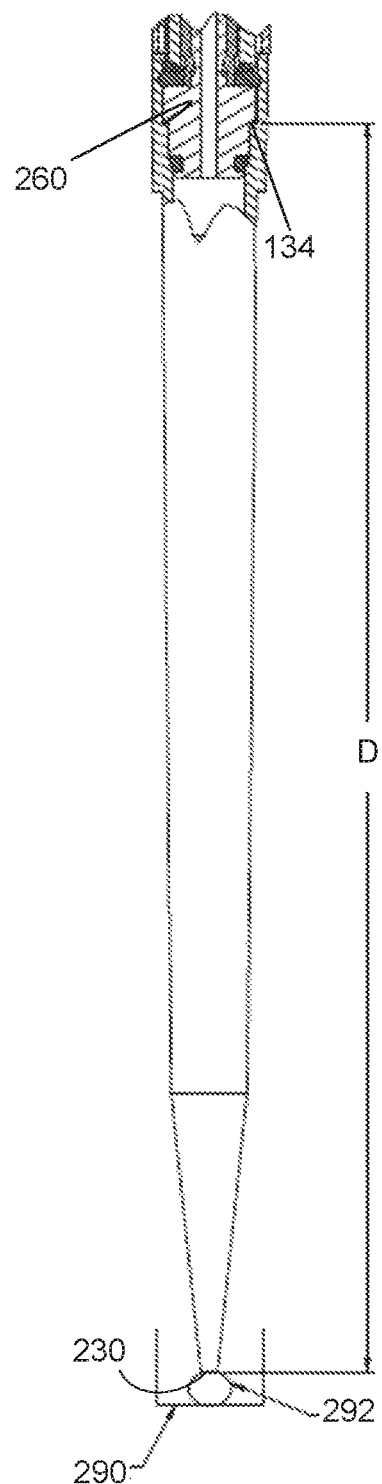
FIG. 32 is a fragmented and cutaway, longitudinal sectional, side elevational view of the air displacement pipette device coupled to the example embodiment of the pipette tip coupler which, in turn, is coupled to the disposable pipette tip illustrated with a small liquid volume interposed between the end of the tip and a working surface and with dimensioning lines illustrated and identified.

FIG. 32 illustrates correct tip alignment with the axial shoulder surface 134 and the axial shoulder seat 260 in flush contact with one another to provide proper alignment and to maintain the tip axial distance D from the tip seat 260 to the distal end 230 constant to establish a known and controlled distance of the pipette tip end 230 along the vertical or axial axis Z (FIG. 26) and a perpendicular axis X (FIG. 26). This is important to allow the pipette device to target small holes and small volumes of liquid. Additionally, smaller volumes of liquid can be transferred resulting from the known fixed distance of the pipette tip allowing for a controlled touch of the pipette tip/liquid to the working surface 290 onto or from which liquid 292 is to be transferred.

Dimensions and Relationships

For proper use and operation, and referring to FIGS. 6 through 16, the dimensions between the coupler 100 and tip 220 are related accordingly. In particular, tip internal diameters of first section 242 and second section 262 must be larger than the diameter of the first cylindrical portion and the second cylindrical portion 130, 132 respectively. However, they must not be too much bigger, as this may result in a poor fit and/or misalignment.

Additionally, the diameter of tip groove 246 must be large enough to allow the primary O-ring 160 to pull the tip up adequately lock the tip 220 in place. Conversely, if it is too big, the primary O-ring 160 may not be able to be extruded sufficiently to get a good lock and/or seal.

The dimension between tip seat 260 to groove 246 dimension must be matched to the stop disk seat 134 to O-ring 160 mounting surface 122 for providing proper coupling between the tip 220 and coupler 100.

The tip seat 260 to secondary O-ring seal land 270 dimensions must match the stop disk seat 134 to secondary O-ring groove 154 dimension. These dimensions control the amount that the secondary O-ring 180 is compressed, and thus how well it seals.

As illustrated in FIG. 32, the tip seat 260 to distal end 230 axial dimension D along with the mating of the coupling seats establish a known and controlled distance of the pipette tip end 230 along the vertical or axial axis Z and a perpendicular axis X. This is important to allow the pipette device to target small holes and small volumes of liquid. Additionally, smaller volumes of liquid can be transferred resulting from the known fixed distance of the pipette tip allowing for a controlled touch of the pipette tip/liquid to the working surface 290 onto or from which liquid 292 is to be transferred.

As illustrated, in FIG. 32 the fully mated tip and stop disk seating/coupling surfaces 134, 260 provide proper alignment and maintain the tip axial distance D.

Liquid Level Detection (LLD) Circuit Contacts

Figure 33:
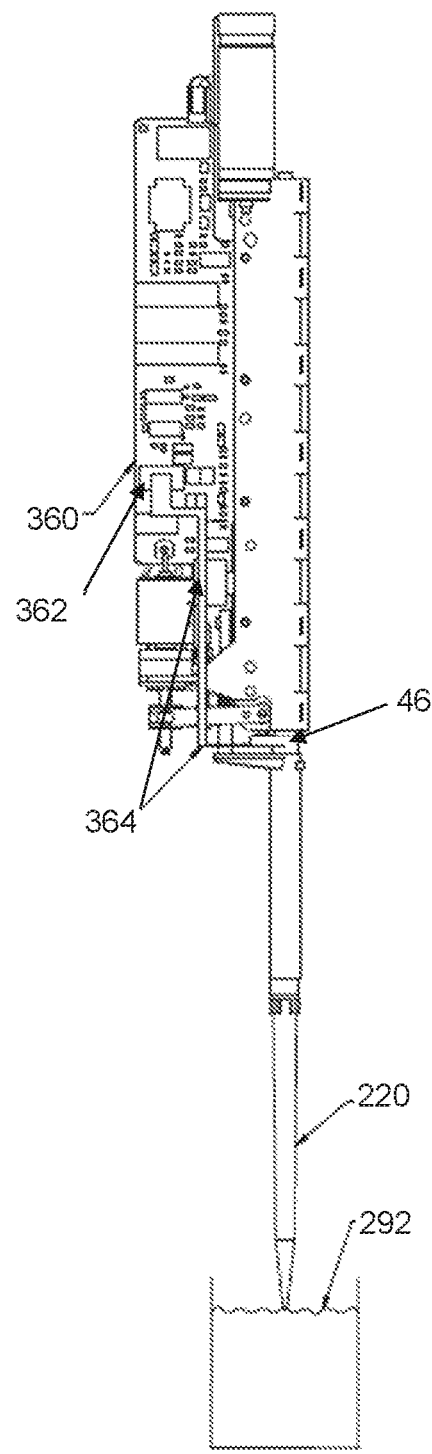
FIG. 33 is a longitudinal side elevational view of the air displacement pipette device assembly illustrating a circuit board that processes the signal from a Liquid Level Detection (LLD) circuit contact wherein the LLD circuit contact is selectively connected between the circuit board and the tip wherein the distal end of the tip is illustrated in contact with the liquid.

Referring to FIGS. 2 and 33, and in one example embodiment of the present disclosure, the pipette device assembly 10 comprise a liquid level detection circuit assembly having an ability to detect a surface of a liquid being transferred or a surface onto or from which liquid is being transferred.

Referring to FIG. 33, and in one example embodiment, the liquid level detection circuit assembly comprises a liquid level detection or LLD circuit board 360 comprising processing circuitry 362 electrically coupled to a LLD circuit contact 364 operatively coupled to the squeeze piston 46 which is made from an electrically non-conducting material so it is insulated from the rest of the assembly. Additionally, the LLD circuit contact 364 terminates to a circuit contact ring end 366 (FIG. 26) recessed in the bottom area of the squeeze sleeve 46 that is configured for selectively contacting the circuit contact ring end 366 with squeeze ring 200 between the non-contact state illustrated in FIG. 18 and the contact state illustrated in FIG. 26. In one example embodiment, the primary O-ring 160 is made using an electrically conductive elastomeric material. Thus, in the contact state, the squeeze ring 200 compresses the primary O-ring 160 for coupling the primary O-ring 160 with the interior first working surface of tip 220 for completing the circuit between the processing circuitry 362 of the LLD circuit board 360 and the tip 220 which is also made from an electrically conductive material.

Additionally, the stop disk mounting post or distal mounting flange 36 (FIG. 26) is made from a non-conducting material. Therefore, the body member 120 (FIG. 6) and primary O-ring 160 are insulated from the rest of the assembly.

Furthermore, the processing circuitry 362 of the LLD circuit board 362 detects a signal change when the tip 220 contacts liquid thereby having an ability to detect a surface of a liquid being transferred or a surface onto or from which liquid is being transferred. Again, actuation occurs when the coupler 100 (FIG. 26) is attached to the tip 220 and the primary O-ring is compressed and locked into the tip groove of the tip 220.

Pipette Device Assembly with Pipette Tip Coupler 400

Figure 34:
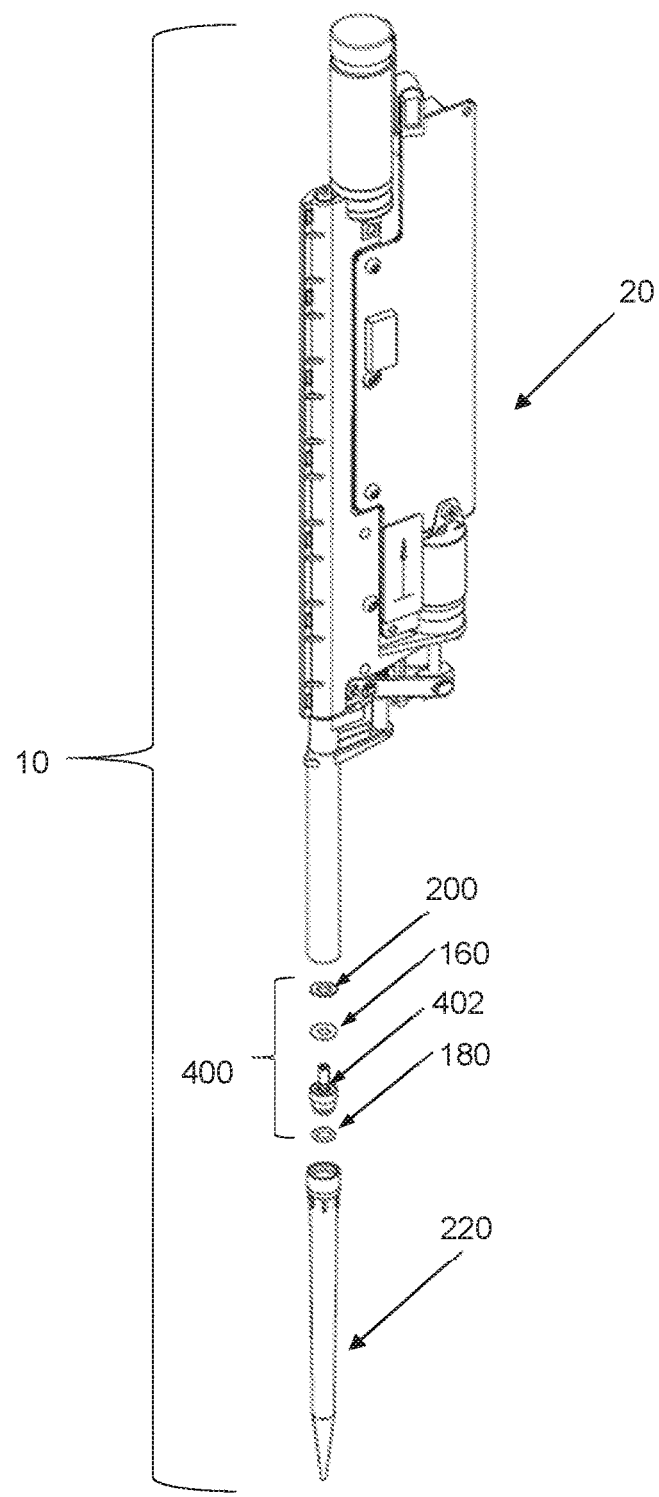
FIG. 34 is a partial exploded parts perspective view detailing parts of another or second example embodiment of the pipette tip coupler device interposed between the disposable pipette tip and the pipette device of the air displacement pipette device assembly.

FIG. 34 illustrates an example embodiment of the pipette device assembly 10 comprising the pipette device 20, a pipette tip coupler 400, and the disposable pipette tip 220 removably coupled to the pipette device 20 by way of the pipette tip coupler 400.

In comparison to one another, the one difference between the pipette tip coupler 400 and the pipette tip coupler 100 are the respective upper circular body end surfaces 122 (FIG. 7) and 402 (FIG. 35); therefore, the numbering of the new portions of the coupler 400 is be updated to reflect the change and all other numbering for like elements and portions remain unchanged.

Figure 35:
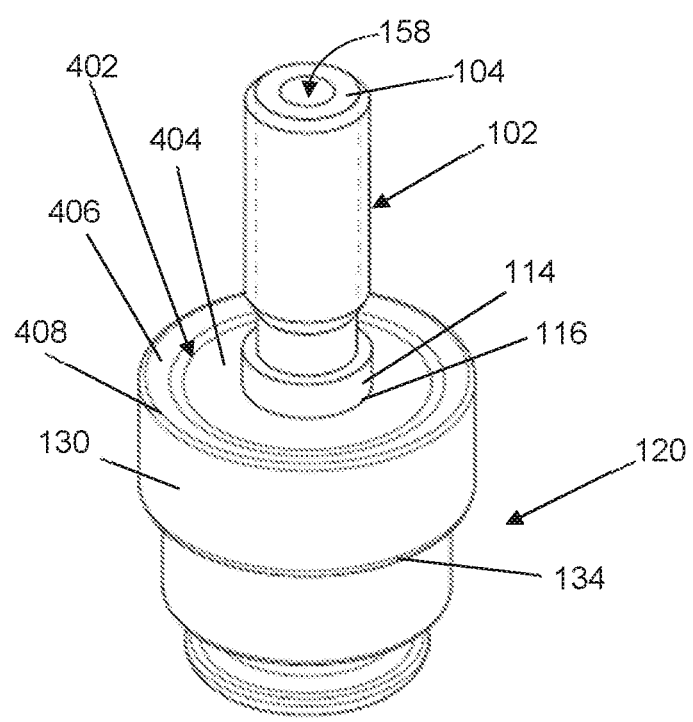
FIG. 35 is a top and side perspective view of a second example embodiment of a pipette tip coupler body of the second example embodiment of the pipette tip coupler.
Figure 36:
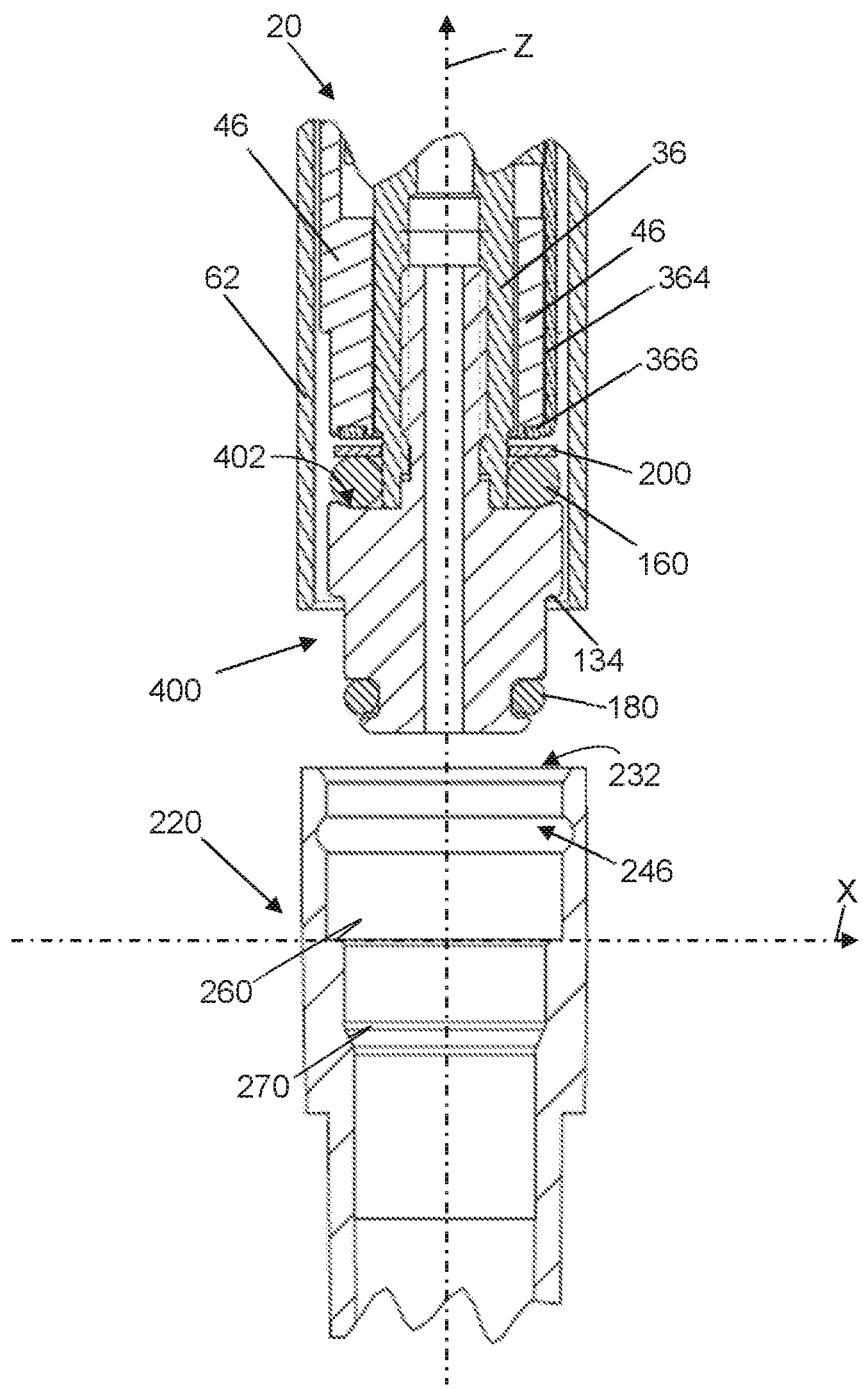
FIG. 36 is a longitudinal sectional, side elevational, fragmented view of the second example embodiment of the pipette tip coupler axially aligned over the example embodiment of the disposable pipette tip.

Referring to FIGS. 34 through 36, an example embodiment of the pipette tip coupler 400 comprises the elongated head or shank member 102 surmounting the pipette tip coupler body member 120, the primary elastomeric element 160 carried at the proximate or upper end portion of the pipette tip coupler body 120, the secondary elastomeric element 180 carried at the distal or lower end portion of the pipette tip coupler body 120, and the squeeze member in the form of, but not limited to, an annular planar squeeze ring 200 surmounting the primary elastomeric element 160 such that the primary elastomeric element 160 is interposed between the superior, or proximal, or upper end surface 402 and the annular planar squeeze ring 200.

Superior, Proximal, or Upper End Surface 402

As illustrated in FIG. 35, the superior, proximal, or upper end surface 402 of the example embodiment of the pipette tip coupler 400 comprises a substantially planar upper inner abbreviated circular surface section 404 radially transitioning from the distal end 116 of the cylindrical collar 114 to an inclined outer annular upper surface section 406 defining an outer conical upper surface section 406 that terminates to an outer peripheral edge 408 of the first cylindrical portion or stop disk 130.

The outer conical upper surface section 406 can also be formed by a plurality of concentrically adjacent outer annular inclined upper surface sections each having a different degree of inclination such as, but not limited to, a first outer annular inclined upper surface section concentrically adjacent and circumscribed by a second outer annular inclined upper surface section having a greater inclination than the first outer annular inclined upper surface section.

Pipette Tip Pickup Process with Pipette Tip Coupler 400

FIGS. 36 through 40 illustrate details of successive stages of an example method of securing attachment of the pipette tip 220 to the pipette tip coupler 400 operatively carried by the pipette device 20. Pipette tip 220 may be supported as detailed above.

With the pipette tip coupler 400 connected to the pipette device 20, and upon initialization, the pipette tip coupler 400 is positioned over the open proximal end 232 of the pipette tip 220 wherein each of their respective central longitudinal axes is aligned along the Z-axis as illustrated in FIG. 36. The eject sleeve 62 is in the eject position, the squeeze piston 46 is in the unsqueezed position, and the primary and secondary O-rings 160, 180 are in the unsqueezed state.

Figure 37:
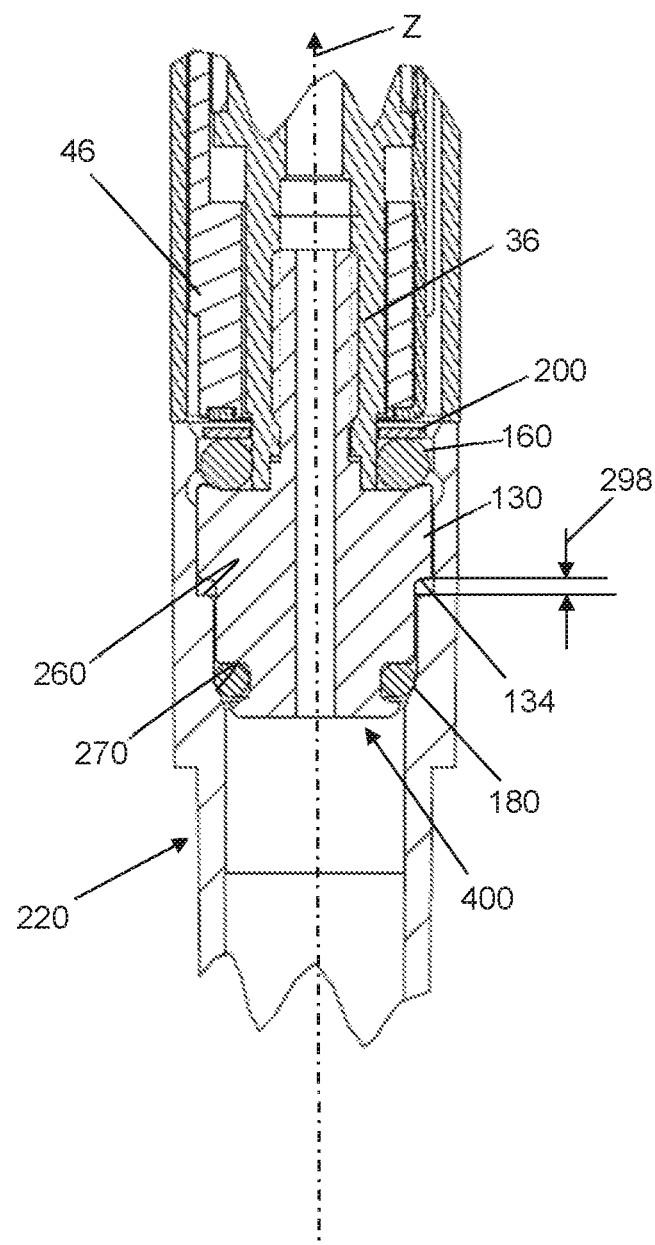
FIG. 37 is a longitudinal sectional, side elevational, fragmented view of the second example embodiment of the pipette tip coupler axially moved into the example embodiment of the disposable pipette tip an amount for defining a stage of coupling that brings a secondary O-ring of the second example embodiment of the pipette tip coupler into contact with the tip sealing seat or surface of the example embodiment of the disposable pipette tip while maintaining a primary O-ring of the second example embodiment of the pipette tip coupler in the unsqueezed state such that a gap is maintained between the shoulder seat of the example embodiment of the disposable pipette tip and a stop shoulder surface of the second example embodiment of the pipette tip coupler.

Next, FIG. 37 illustrates the step of the pipette tip coupler 400 being moved down along the Z-axis into the pipette tip 220 and then lowered, causing the distal, elastomeric carrying portions, of the pipette tip coupler 400 to pass into the interior cylindrical proximal end portions of the pipette tip 220 to bring the secondary O-ring 180 into contact with the tip annular sealing seat or stop surface 270 while maintaining the primary O-ring 160 in the unsqueezed state and before the annular shoulder seat or axial stop surface 260 of the pipette tip 220 and the axial stop shoulder surface 134 of the pipette tip coupler 400 are mated such that a gap 298 is maintained between the annular shoulder seat or stop surface 260 of the pipette tip 220 and the axial stop shoulder surface 134 of the pipette tip coupler 400.

Figure 38:
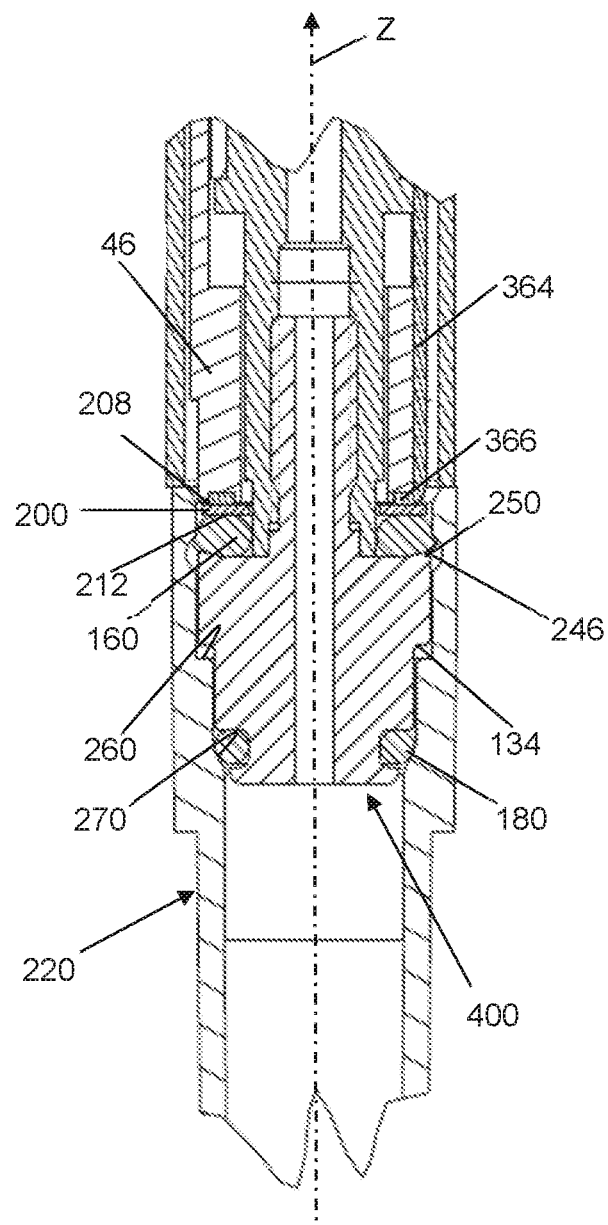
FIG. 38 is a longitudinal sectional, side elevational, fragmented view of the second example embodiment of the pipette tip coupler moved into the tip an additional amount with the tip being lifted up while pushing down on the squeeze ring for defining a stage of squeezing the primary O-ring to a first compressed and extruded state or squeezed state from an unsqueezed state and compressing the secondary O-ring to a first compressed state against the tip sealing seat or surface.

Next, FIG. 38 illustrates the step of the squeeze piston 46 being moved down along the Z-axis and pushing against the LLD circuit ring end 366 which contacts with and pushes against the top surface 208 of the annular squeeze ring 200 having the bottom end 212 surmounting the primary O-ring 160 wherein the primary O-ring 160 starts to be squeezed and subsequently extruded into the groove 246 and into abutment with the upper axially arcuate circumferential surface sector portion 250 of the axially arcuate circumferential interior surface 244 (FIG. 15) defining the groove 246.

As illustrated in FIG. 38, the action of the primary O-ring 160 extruding into the groove 246 causes an axial upward force that pulls the pipette tip 220 up for starting a process of seating the annular shoulder seat surface 260 of the pipette tip 220 with the axial stop shoulder surface 134 of coupler 400 for closing the gap 298 (FIG. 37) and compressing the secondary O-ring 180 with the frustoconical annular sealing seat surface or stop surface 270 of the tip 220.

Figure 39:
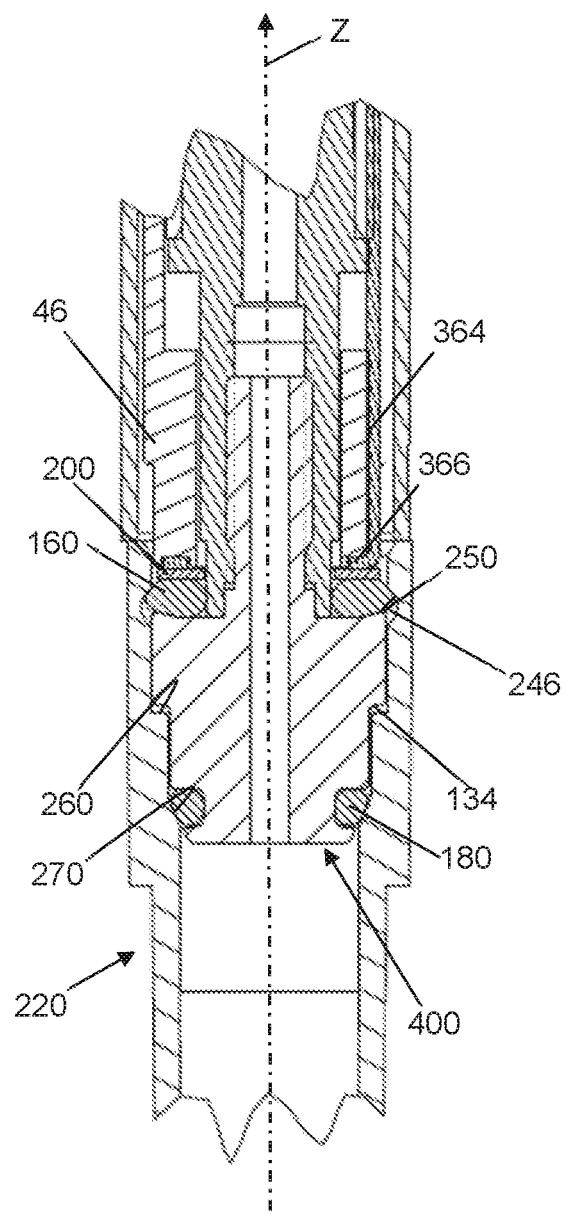
FIG. 39 is a longitudinal sectional, side elevational, fragmented view of the second example embodiment of the pipette tip coupler moved into the tip a further amount with the tip being lifted up while pushing down on a squeeze ring for defining a second or subsequent state of squeezing the primary O-ring to a second or subsequent compressed and extruded state and compressing the secondary O-ring to a second compressed state against the tip sealing seat or surface.

FIG. 39 illustrates the next step of the squeeze piston 46 continuing to move further down along the Z-axis with the annular squeeze ring 200, via LLD circuit ring end 366, continuing to push down on the primary O-ring 160 for extruding the primary O-ring 160 further into the groove 246 of the pipette tip 220 and further into abutment with the upper axially arcuate circumferential surface sector portion 250 for pulling the tip axially up along the Z-axis for further closing gap 298 (FIG. 37) and causing the secondary O-ring 180 to be further compressed against annular sealing seat or stop surface 270 such that its cross-section is no longer circular as illustrated in FIG. 36.

Figure 40:
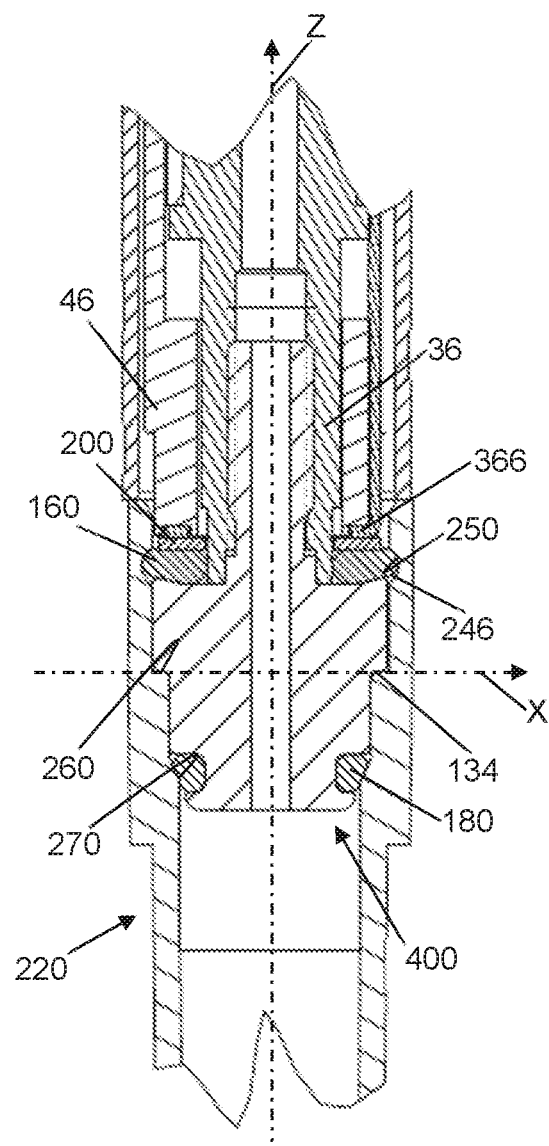
FIG. 40 is a longitudinal sectional, side elevational, fragmented view of the second example embodiment of the pipette tip coupler moved into the example embodiment of the disposable pipette tip to a final amount with the tip being lifted up to its final seated state to engage the coupler by the method of moving the squeeze ring into its final position thereby defining a final state of coupling with the distal elastomeric element or O-ring in a final compressed and seated sealing state.

FIG. 40 illustrates the finishing step of the squeeze piston 46 finishing moving down along the Z-axis a pre-calibrated or predetermined length until it is locked in position resulting in the annular squeeze ring 200 being stopped and locked in position by the squeeze piston 46, via LLD circuit ring end 366. As a result, the primary O-ring 160 is compressed circumferentially to a desired value for fully seating the axial stop shoulder surface 134 of the pipette tip coupler 400 against the annular shoulder seat surface 260 of the pipette tip 220 with the seating of the two surfaces 134, 260 along an X-axis substantially perpendicular to the Z-axis for forming a normal datum between the two axes while the secondary O-ring 180 is compressed to a desired value for seating the secondary O-ring 180 with the annular sealing seat or stop surface 270 of the tip 220 such that its cross-section is in its final compressed non-circular form thereby completing the coupling of the pipette tip coupler 400 with the pipette tip 200. Upon completion of the securing attachment process, the first and second elastomeric elements 160, 180 work in combination to produce a fluid-tight seal wherein the first elastomeric element 160 is at least partially seated in the circumferential arcuate interior surface 244 (FIG. 15) defining the circumferential groove 246 and wherein the second elastomeric element 180 seals against the radially inwardly angled and distally extending surface 270 of the pipette tip 220.

Figure 41:
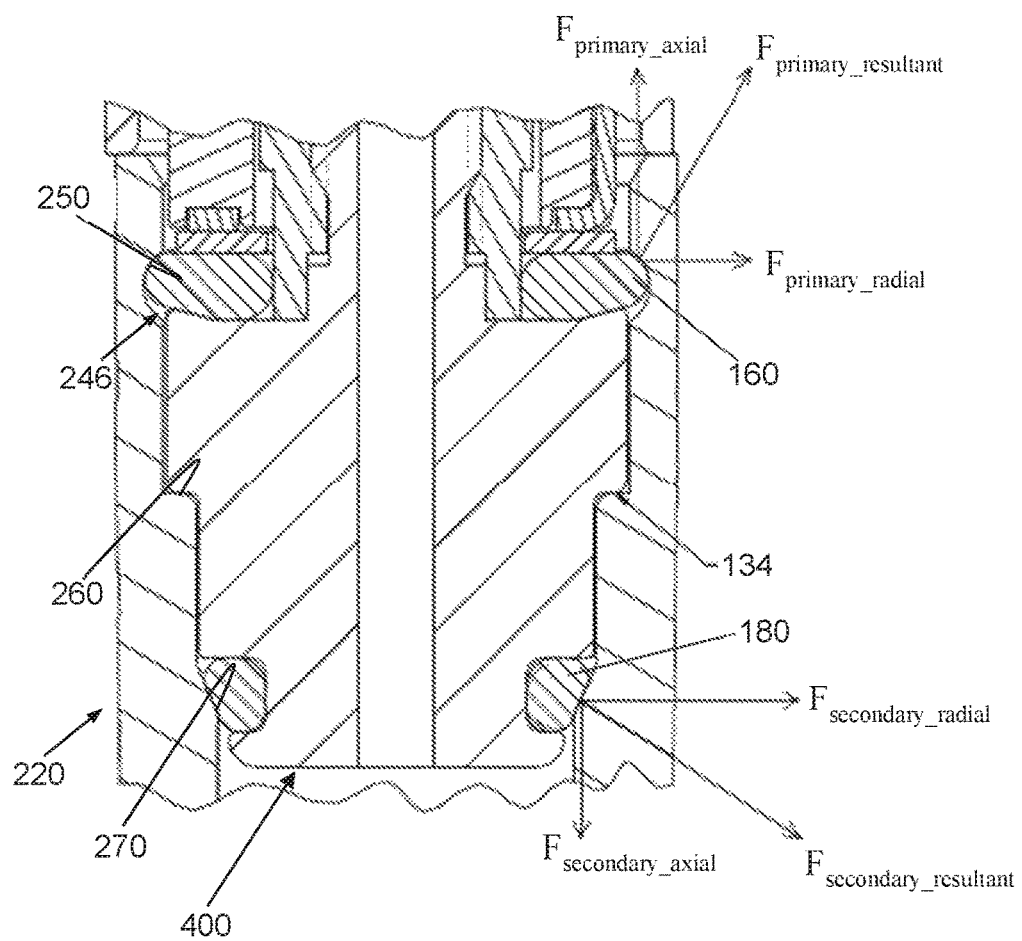
FIG. 41 is a fragmentary, longitudinal sectional, side elevational, detailed view of the completed coupling of the second example embodiment of the pipette tip coupler and the example embodiment of the disposable pipette tip with associated coupling forces illustrated and identified thereon.

It should be noted that the inclined outer annular upper surface section 406 (FIG. 35) results in the extrusion of the primary O-ring 160 to be more concentrated on portion 250 and angled toward the edge 248 (FIG. 16) as illustrated in FIG. 41.

Ejection Process

The tip ejection process sequence follows the attachment or tip pickup securing process sequence except in reverse. In reverse, FIGS. 36 through 40 illustrate, details of successive stages of an example method or process of ejecting the pipette tip 220 from the pipette tip coupler 400 operatively carried by the pipette device 20. This process analogously follows the above detailed description for ejecting the pipette tip 220 from the pipette tip coupler 100, operatively carried by the pipette device 20.

Coupling Forces

FIG. 41 illustrates a diagrammatical vector diagram of the primary O-ring 160 of pipette tip coupler 400 extruding into the groove 246 and the axial upward force pulling the pipette tip 220 upward wherein the primary O-ring 160 pushes against the upper part 250 of the tip groove 246 with a force (Fprimary_resultant) and the secondary O-ring 180 has a force (Fsecondary_resultant) that results from being compressed.

As illustrated in FIG. 41, the primary O-ring force (Fprimary_resultant) is comprised of two components: an axial force component (Fprimary_axial) and a radial force component (Fprimary_radial). The primary O-ring axial force component (Fprimary_axial) seats the stop shoulder surface 134 of pipette tip coupler 400 against the axial stop surface 260 of tip 220 and provides the force required to compress the secondary O-ring 180 while the primary O-ring radial force component (Fprimary_radial) provides the radial force needed to seal the primary O-ring 160 against the upper part 250 of the tip groove 246.

FIG. 41 further illustrates that the secondary O-ring 180 is also comprised of two components: an axial force component (Fsecondary_axial) and a radial force component (Fsecondary_radial). The secondary O-ring axial force component (Fsecondary_axial) provides a counter force to the primary O-ring axial force component (Fprimary_axial) that benefits the sealing of the primary O-ring 160 by pulling the tip 220 down wherein this pressure further pushes or biases the primary O-ring 160 into the upper corner or upper part 250 of the tip groove 246. The secondary O-ring axial force component (Fsecondary_axial) also provides force to help remove the tip 220 during ejection. The secondary O-ring radial force component (Fsecondary_radial) provides the radial force needed to seal the secondary O-ring 180 against the annular sealing seat or stop surface 270 of the tip 220.

Alignment/Misalignment

With respect to coupler 400, it is noted that the axial shoulder surface 134 and the axial shoulder seat 260 of tip 220 follow the same importance for correct tip alignment as described in detail above for coupler 100.

Dimensions and Relationships

For proper use and operation, dimensions between the coupler 400 and tip 220 are related accordingly as described in detail above for coupler 100.

Pipette Device Assembly with Pipette Tip Coupler 500

Figure 42:
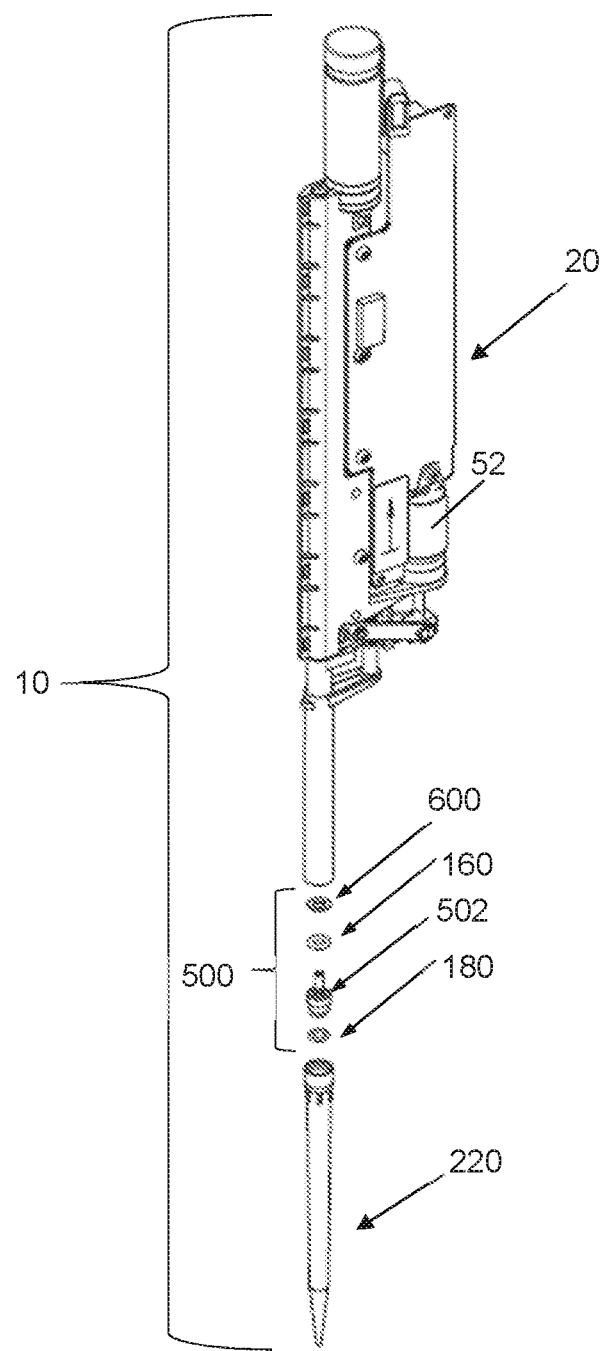
FIG. 42 is a partial exploded parts perspective view detailing parts of another or a third example embodiment of the pipette tip coupler device interposed between the disposable pipette tip and the pipette device of the air displacement pipette device assembly.

FIG. 42 illustrates an example embodiment of the pipette device assembly 10 comprising the pipette device 20, a pipette tip coupler device 500, and the disposable pipette tip 220 removably coupled to the pipette device 20 by way of the pipette tip coupler 500. In comparison to one another, and as detailed below, the difference between the pipette tip coupler 500 and the pipette tip couplers 100 and 400 are respective superior or upper body end surfaces 502 (FIG. 44), 122 (FIG. 7), and 402 (FIG. 35) of each coupler and the squeeze rings 600 (FIG. 45) and 200 (FIG. 11). Accordingly, the numbering of the new portions of the coupler 500 will be updated to reflect these changes and all other numbering for like elements and portions will remain unchanged. However, annular planar squeeze ring 200 may be used with pipette tip coupler 500 in place of annular wedge squeeze ring 600. Similarly, annular wedge squeeze ring 600 may be used with pipette tip coupler 100 or pipette tip coupler 400 in place of annular planar squeeze ring 200.

Pipette Tip Coupler 500

Figure 43:
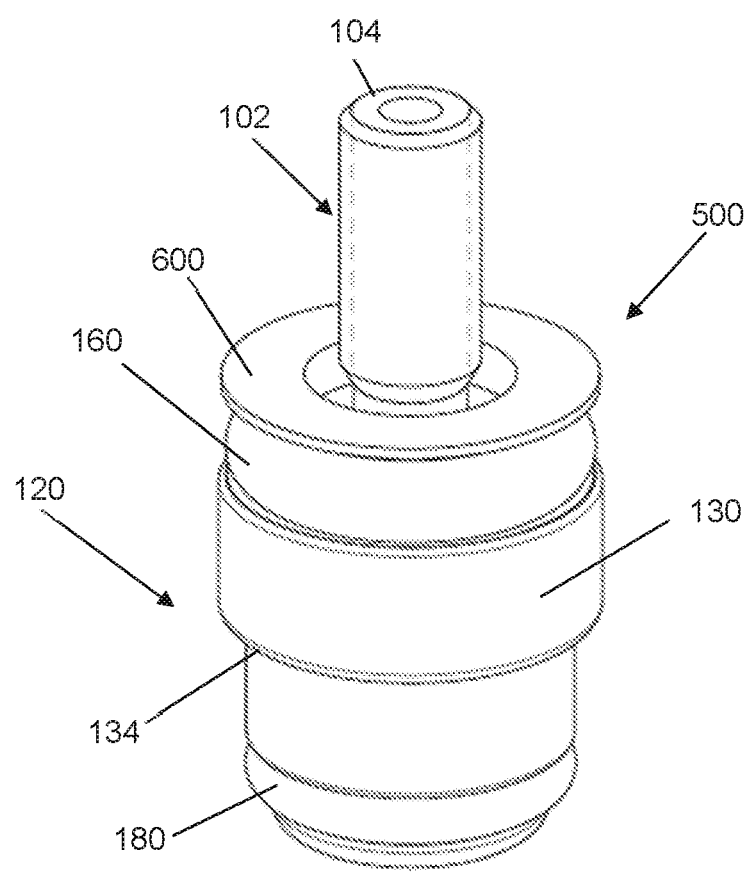
FIG. 43 is a top and side perspective view of the third example embodiment of the pipette tip coupler.

Referring to FIGS. 42 and 43, pipette tip coupler 500 comprises the elongated head or shank member 102 surmounting the pipette tip coupler body member 120, the primary elastomeric element 160 carried at a proximate or upper end portion of the pipette tip coupler body 120, the secondary elastomeric element 180 carried at a distal or lower end portion of the pipette tip coupler body 120, and a squeeze member in the form of, but not limited to, an annular wedge squeeze ring 600. Wedge squeeze ring 600 surmounts the primary elastomeric element 160 such that the primary elastomeric element 160 is interposed between a superior, proximal, or upper end surface 502 (FIG. 44) of the pipette tip coupler body 120 and a wedge side 614 (FIG. 45) of the annular wedge squeeze ring 600.

Superior, Proximal, or Upper End Surface 502

Figure 44:
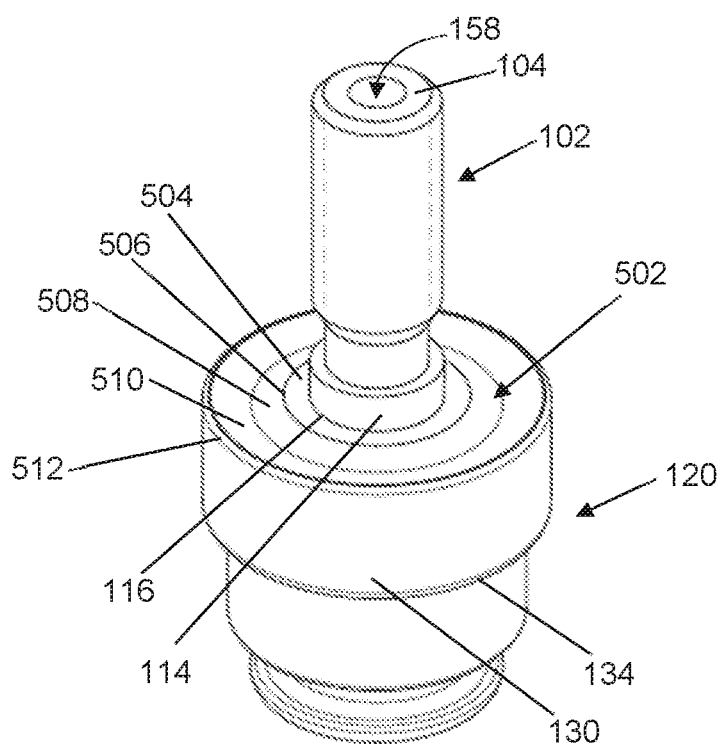
FIG. 44 is a top and side perspective view of a third example embodiment of a pipette tip coupler body of the third example embodiment of the pipette tip coupler.

Referring to FIG. 44, the pipette tip coupler 500 comprises the superior, proximal, or upper end surface 502 of the pipette tip coupler body 120 that comprises a substantially planar inner annular upper surface section 504 that transitions from the distal end 116 of the cylindrical collar 114 to an outer circumference 506 that transitions into a downwardly inclined radially outwardly extending annular upper surface slope section 508 that transitions into a slightly concaved, upwardly inclined, radially outwardly extending annular upper surface section 510 that terminates to a rounded upper lift edge 512 that radially outwardly and downwardly transitions to the outer periphery edge of the pipette tip stop disk 130 of the coupler body 120.

Figure 46:
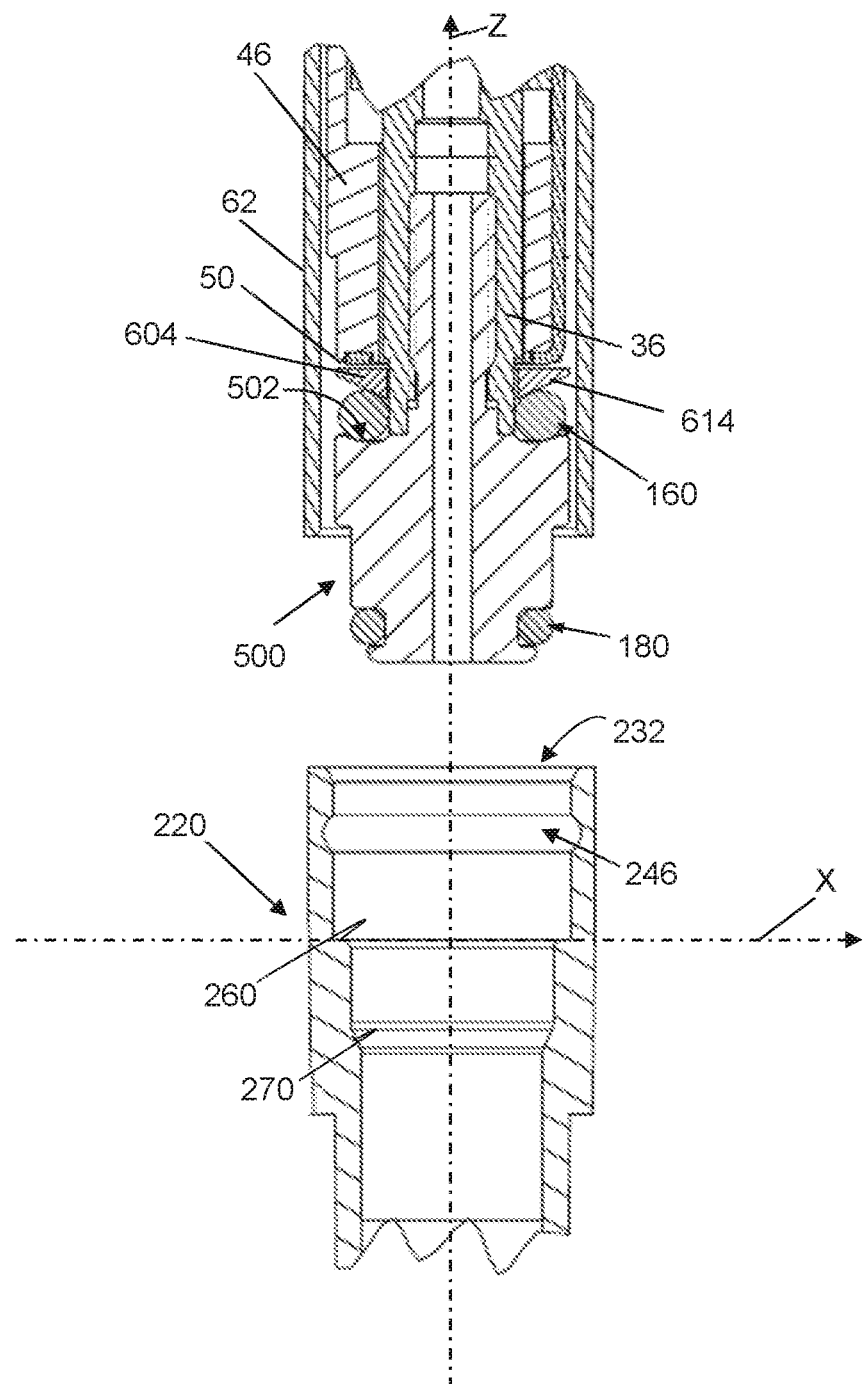
FIG. 46 is a longitudinal sectional, side elevational, fragmented view of the third example embodiment of the pipette tip coupler axially aligned over the example embodiment of the disposable pipette tip.

Accordingly, and as illustrated in FIG. 46, an embodiment of the upper end surface 502 comprises a generally flattened and spread apart U-shaped cross section or concave wedge shaped cross section defined by having an outer leg with a length greater than a length of an inner leg and an outer leg with a slope that is less than an inner leg slope with respect to a central curved portion of the generally flattened and spread apart U-shaped or concave wedge shaped cross section.

Annular Wedge Squeeze Ring 600

Figure 45:
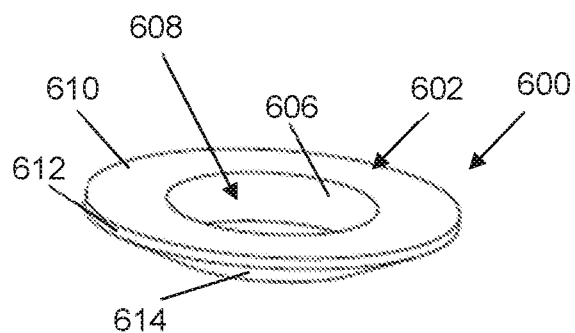
FIG. 45 is a top and side perspective view of an annular wedge squeeze ring of the third example embodiment of the pipette tip coupler.

Referring to FIG. 45, and in one example embodiment, the annular wedge squeeze ring 600 comprises a resilient wedge shaped annular body 602 having a circumferentially continuous, generally wedge shaped or triangular shaped cross section 604 as illustrated in FIG. 46. Additionally, the resilient wedge shaped annular body 602 comprises a central interior annular surface 606 defining a central annular opening 608 extending through the annular body 602. The wedge shaped annular body 602 further comprises a top planar circular surface 610 radially outwardly extending from the central interior annular surface 606 to a circumscribing axially extending outer edge surface 612. Moreover, the wedge shaped annular body 602 comprises a radially outwardly proximally inclined annular bottom surface 614 radially extending from the central interior annular surface 606 to the circumscribing axially extending outer edge surface 612 wherein a first axial length of the central interior annular surface 606 is greater than a second axial length of the outer edge surface 612.

Figure 52:
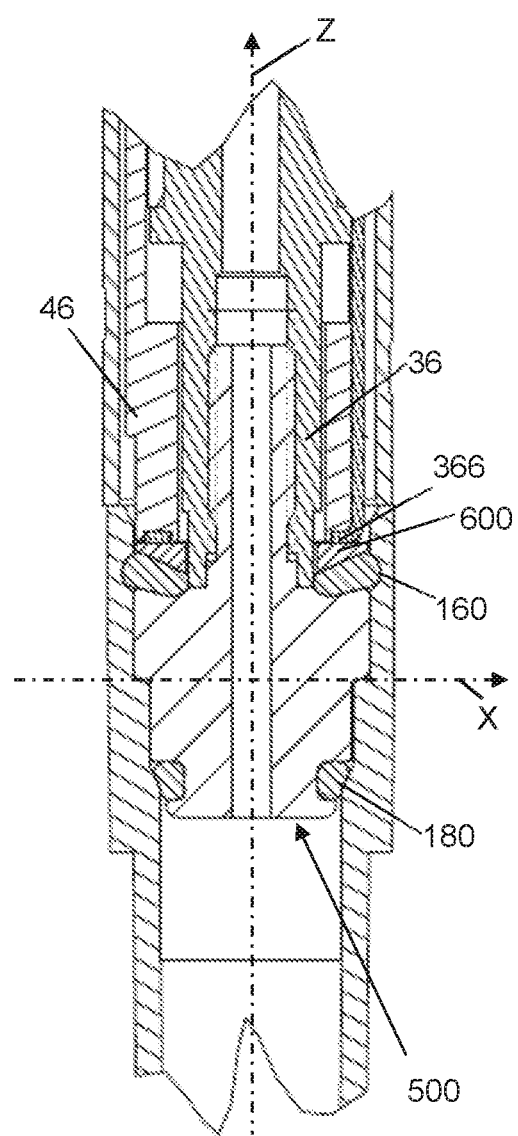
FIG. 52 is a longitudinal sectional, side elevational, fragmented view of the third example embodiment of the pipette tip coupler axially moved into the example embodiment of the disposable pipette tip to a final amount with the tip being lifted up to its final seated state to engage the coupler by the method of moving the squeeze ring into its final position thereby defining a final state of coupling with the distal elastomeric element or O-ring in a final compressed and seated sealing state.

Referring to FIGS. 45 and 46, the central annular opening 606 of the annular wedge squeeze ring 600 is dimensioned to allow the distal mounting flange 36, with the pipette tip coupler 500 fitted therein, to pass through so as to allow a seating abutment of radially outwardly proximally inclined annular bottom surface 614 with primary elastomeric member 160 carried on the upper end surface 502 of the pipette tip coupler body 120 of the pipette tip coupler 500. Additionally, the top planar surface 610 of the annular squeeze ring 600 is initially spaced from the distal end 50 of the squeeze piston 46 in a home position such that the upper elastomeric element 160 is in the relaxed or unsqueezed state. Accordingly, actuation of the squeeze motor 52 (FIG. 42) in the first direction results in linear axial translation of the squeeze sleeve 46 in a distal or vertically downward direction for axially squeezing the primary elastomeric member 160 between the radially outwardly proximally inclined annular bottom surface 614 of the annular squeeze ring 600 and the upper end surface 502 of the pipette tip coupler 500 such that an axial height of the upper elastomeric member 160 increases from an inner to an outer radius and the radial axis is upwardly or proximally inclined in a squeezed state as compared to an at rest state. In other words, the annular wedge squeeze ring 600 provides a radially inclined displacement of the upper elastomeric member 160 upon its axial compression by the axial force applied to the top planar circular surface 610 by a controlled axial pressing engagement of the squeeze sleeve 46 with the top surface 610 of the annular wedge squeeze ring 600 as illustrated in FIG. 52 and described below.

Pipette Tip Pickup Process with Pipette Tip Coupler 500

FIGS. 46 through 52 illustrate details of successive stages of a pipette tip pickup method or a method of securing attachment of the pipette tip 220 to the pipette tip coupler 500 operatively carried by the pipette device 20 (FIG. 42). As noted above, and in one example embodiment, the pipette tip 220 may be supported by the support surface 282 (FIG. 18).

With the pipette tip coupler 500 connected to the pipette device 20, and upon initialization, the pipette tip coupler 500 is positioned over the open proximal end 232 of the pipette tip 220 wherein each of their respective central longitudinal axes is aligned along the Z-axis as illustrated in FIG. 46. The eject sleeve 62 is in the eject position, the squeeze piston 46 is in the unsqueezed position, and the primary and secondary O-rings 160, 180 are in the unsqueezed state.

Figure 47:
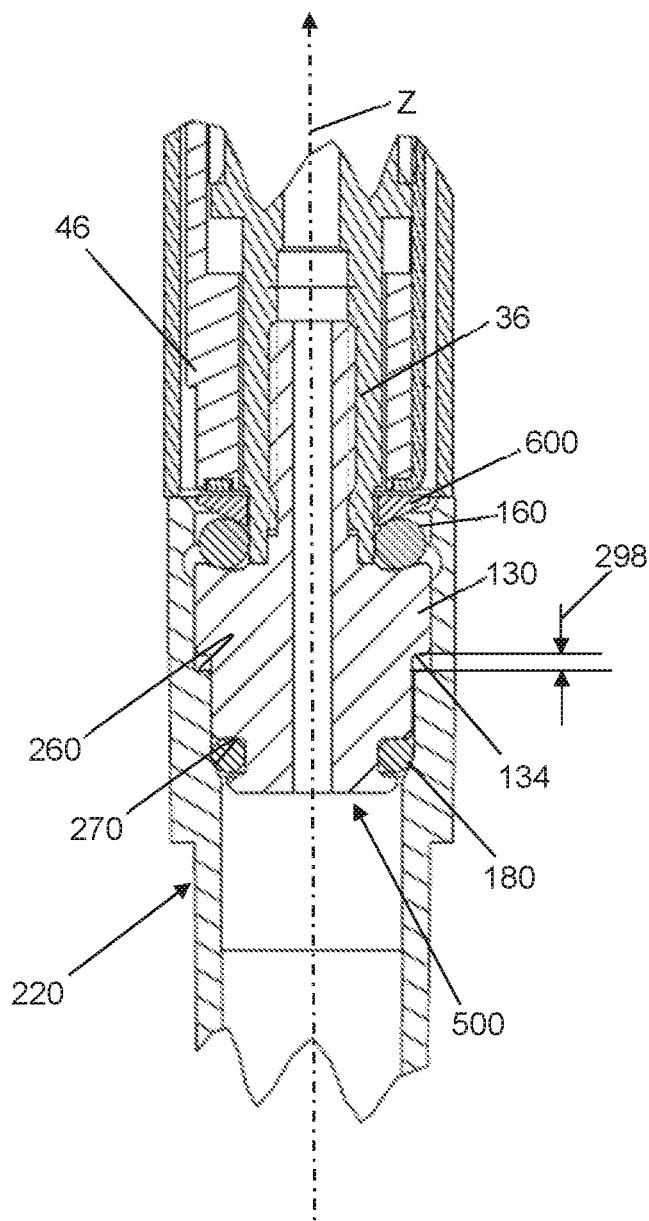
FIG. 47 is a longitudinal sectional, side elevational, fragmented view of the third example embodiment of the pipette tip coupler axially moved into the example embodiment of the disposable pipette tip an amount for defining a stage of coupling that brings a secondary O-ring of the third example embodiment of the pipette tip coupler into contact with the tip sealing seat or surface of the example embodiment of the disposable pipette tip while maintaining a primary O-ring of the third example embodiment of the pipette tip coupler in the unsqueezed state such that a gap is maintained between the shoulder seat of the example embodiment of the disposable pipette tip and a stop shoulder surface of the third example embodiment of the pipette tip coupler.

Next, FIG. 47 illustrates the step of the pipette tip coupler 500 being moved down along the Z-axis into the pipette tip 220 and then lowered, causing the elastomeric carrying portions of the pipette tip coupler 500 to pass into the interior cylindrical proximal end portions of the pipette tip 220 to bring the secondary O-ring 180 into contact with the tip annular sealing seat or stop surface 270 while maintaining the primary O-ring 160 in the unsqueezed state and before the annular shoulder seat or stop surface 260 of the pipette tip 220 and the axial stop shoulder surface 134 of the pipette tip coupler 500 are mated such that a gap 298 is maintained between the annular shoulder seat or stop surface 260 of the pipette tip 220 and the axial stop shoulder surface 134 of the pipette tip coupler 500.

Figure 48:
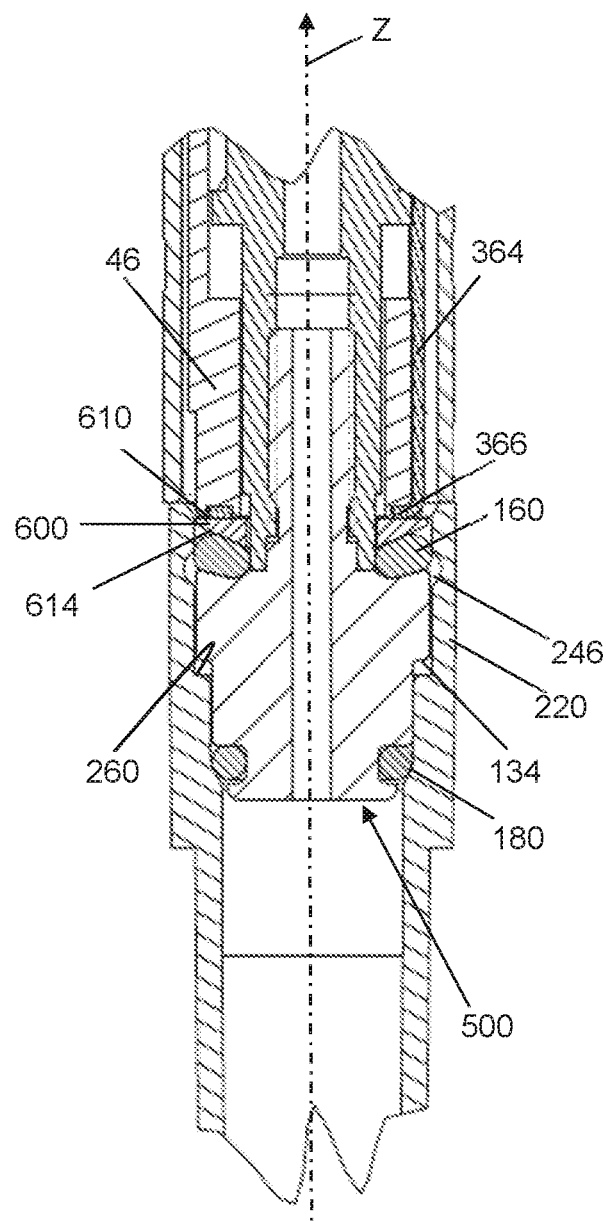
FIG. 48 is a longitudinal sectional, side elevational, fragmented view of the third example embodiment of the pipette tip coupler axially moved into the example embodiment of the disposable pipette tip with the tip being lifted up while pushing down on the wedge squeeze ring for squeezing the primary O-ring to a first compressed and extruded state or squeezed state from an unsqueezed state.

Next, FIG. 48 illustrates the step of the squeeze piston 46 being moved down along the Z-axis into and pushing against the LLD circuit ring end 366 which contacts with and pushes against the top surface 610 of the annular wedge squeeze ring 600 having the bottom end 614 surmounting the primary O-ring 160 wherein the primary O-ring 160 starts to be squeezed and subsequently extruded into the groove 246. As illustrated, the action of the primary O-ring 160 extruding into the groove 246 causes an axial upward force that pulls the pipette tip 220 up for starting a process of seating the annular shoulder seat surface 260 of the pipette tip 220 with the axial stop shoulder surface 134 of the pipette tip coupler 500 for closing the gap 298 (FIG. 47) and compressing the secondary O-ring 180 with the sealing seat surface 270 of the tip 220.

Figure 49:
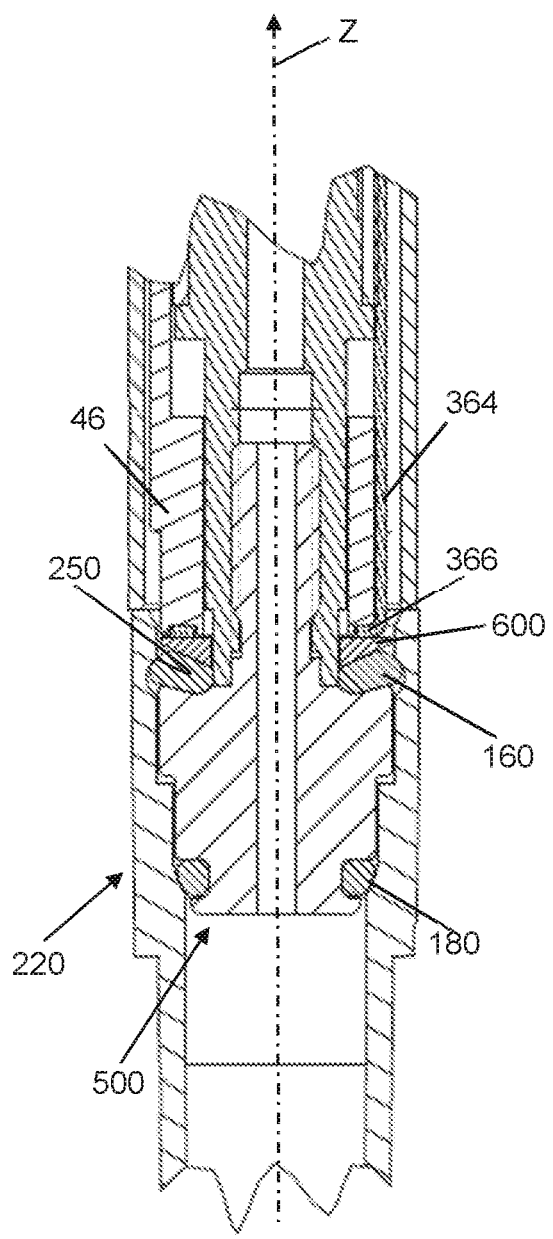
FIG. 49 is a longitudinal sectional, side elevational, fragmented view of the third example embodiment of the pipette tip coupler axially moved into the tip a further amount with the tip being lifted up while pushing further down on the wedge squeeze ring for defining a second or subsequent state of squeezing the primary O-ring to a second or subsequent compressed and extruded state.
Figure 50:
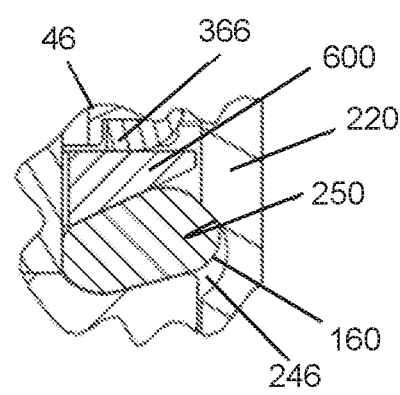
FIG. 50 is a longitudinal sectional, side elevational, fragmented detailed view of the primary O-ring in the subsequent compressed and extruded state as is illustrated in FIG. 49.
Figure 51:
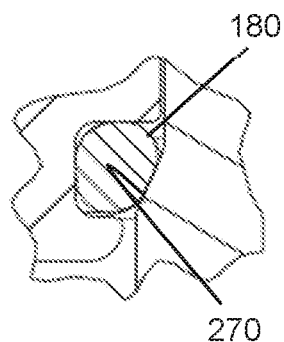
FIG. 51 is a longitudinal sectional, side elevational, fragmented detailed view of the secondary O-ring in the subsequent compressed state against the tip sealing seat or surface as is illustrated in FIG. 49.

Next, FIG. 49 illustrates the step of the squeeze piston 46 continuing to move further down along the Z-axis with the annular wedge squeeze ring 600, via LLD circuit ring end 366, continuing to push down on the primary O-ring 160 for extruding the primary O-ring 160 further into the groove 246 of the pipette tip 220 for providing further abutment with the upper axially arcuate circumferential surface sector portion 250 as illustrated in detail in FIG. 50 for pulling the tip axially up along the Z-axis for further closing gap 298 (FIG. 47) and causing the secondary O-ring 180 to be further compressed against annular sealing seat surface 270 as illustrated in detail in FIG. 51 such that its cross-section is no longer circular.

FIG. 52 illustrates the step of the squeeze piston 46 being moved down along the Z-axis a pre-calibrated or predetermined length until it is locked in position resulting in the annular wedge squeeze ring 600 being stopped and locked in position by the squeeze piston 46 via the LLD circuit ring end 366. As a result, the primary O-ring 160 is compressed circumferentially to a desired value for fully seating the axial stop shoulder surface 134 of the pipette tip coupler 500 against the annular shoulder seat surface 260 of the pipette tip 220 with the seating of the two surfaces 134, 260 along an X-axis substantially perpendicular to the Z-axis for forming a normal datum between the two axes while the secondary O-ring 180 is compressed to a desired value for seating and sealing the secondary O-ring 180 with the annular sealing seat or stop surface 270 of the tip 220 such that its cross-section is in its final compressed non-circular form thereby completing the coupling of the pipette tip coupler 500 with the pipette tip 200. Upon completion of the securing attachment process, the first and second elastomeric elements 160, 180 work in combination to produce a fluid-tight seal wherein the first elastomeric element 160 is at least partially seated in the circumferential arcuate interior surface 244 (FIG. 15) defining the circumferential groove 246 and wherein the second elastomeric element 180 seals against the radially inwardly angled and distally extending surface 270 of the pipette tip 220.

Figure 53:
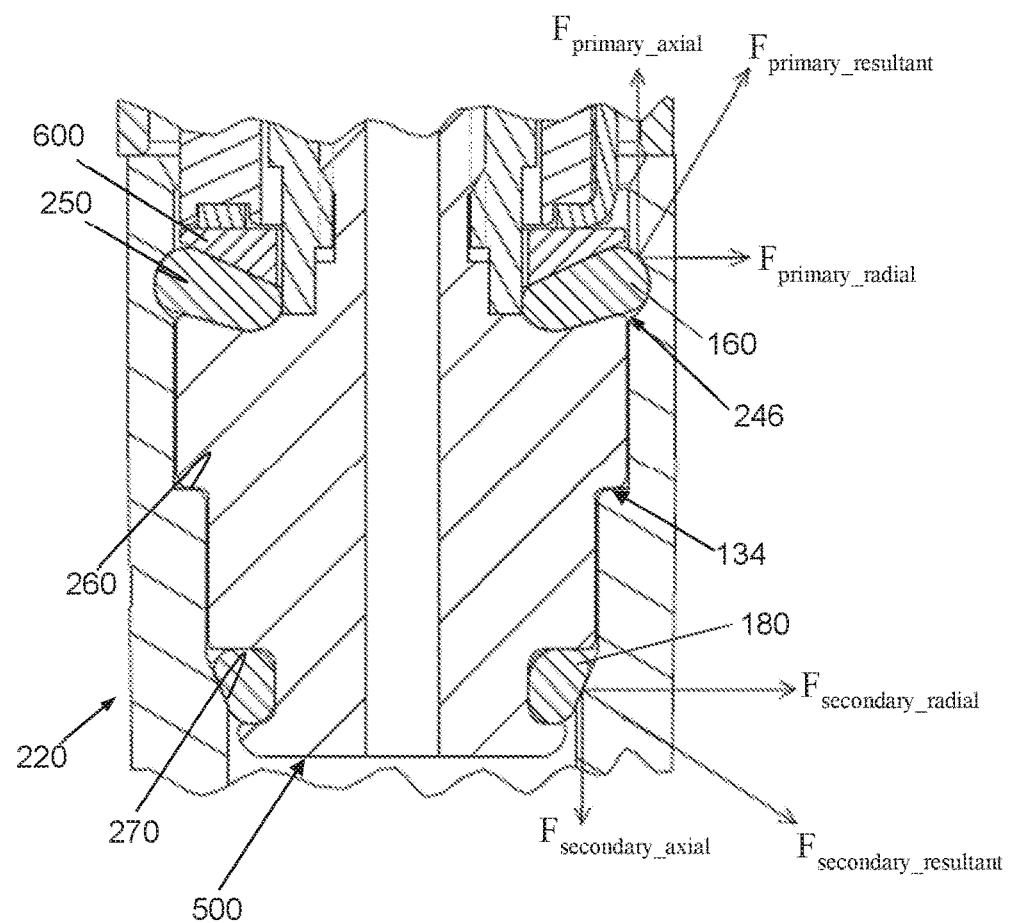
FIG. 53 is a fragmentary, longitudinal sectional, side elevational, detailed view of the completed coupling of the third example embodiment of the pipette tip coupler and disposable pipette tip with associated coupling forces illustrated and identified thereon.

The inclined outer annular upper surface section 510 (FIG. 44) along with the annular wedge squeeze ring 600 provide an extrusion of the primary O-ring 160 to be more concentrated on portion 250 and angled toward the edge 248 (FIG. 16) as illustrated in FIG. 53.

Ejection Process

In reverse, FIGS. 46 through 52 illustrate details of successive stages of an example method or process of ejecting the pipette tip 220 from the pipette tip coupler 500 operatively carried by the pipette device 20. This tip ejection process sequence is similar to the attachment or tip pickup securing process sequence described above except in reverse.

Coupling Forces

FIG. 53 illustrates a diagrammatical vector diagram of the primary O-ring 160 of pipette tip coupler 500 being extruded into the groove 246 by squeezing with a resultant axial upward force pulling the pipette tip 220 upward wherein the primary O-ring 160 pushes against the upper part 250 of the tip groove 246 with a force (Fprimary_resultant) and the secondary O-ring 180 has a force (Fsecondary_resultant) that results from being compressed.

As illustrated in FIG. 53, the primary O-ring force (Fprimary_resultant) is comprised of two components: an axial force component (Fprimary_axial) and a radial force component (Fprimary_radial). The primary O-ring axial force component (Fprimary_axial) seats the stop shoulder surface 134 of coupler 500 against the axial stop surface 260 of tip 220 and provides the force required to compress the secondary O-ring 180 while the primary O-ring radial force component (Fprimary_radial) provides the radial force needed to seal the primary O-ring 160 against the upper part 250 of the tip groove 246.

FIG. 53 further illustrates that the secondary O-ring 180 is also comprised of two components: an axial force component (Fsecondary_axial) and a radial force component (Fsecondary_radial). The secondary O-ring axial force component (Fsecondary_axial) provides a counter force to the primary O-ring axial force component (Fprimary_axial) that benefits the sealing of the primary O-ring 160 by pulling the tip 220 down wherein this pressure further pushes or biases the primary O-ring 160 into the upper corner or upper part 250 of the tip groove 246. The secondary O-ring axial force component (Fsecondary_axial) also provides force to help remove the tip 220 during ejection. The secondary O-ring radial force component (Fsecondary_radial) provides the radial force needed to seal the secondary O-ring 180 against the annular sealing seat or stop surface 270 of the tip 220.

Alignment/Misalignment

With respect to pipette tip coupler 500, it is noted that the axial shoulder surface 134 of coupler 500 and the axial shoulder seat 260 of tip 220 are important for correct tip alignment as noted above for coupler 100.

Dimensions and Relationships

Additionally, respect to pipette tip coupler 500, it is noted that for proper use and operation, dimensions between the coupler 500 and tip 220 are related accordingly as noted above for coupler 100.

Securing Attachment Method

In light of the above detailed disclosure, and in one example embodiment, a method is provided for securing attachment of at least one pipette tip to at least one pipette tip coupler carried by a pipette device, the method comprising: (1) providing a pipette tip comprising a sidewall having an interior circumscribing surface defining a passage opening extending between an open distal end intended for immersion in a medium to be pipetted and an open proximal end opposite in an axial direction to the open distal end; (2) providing a pipette tip coupler comprising a distally facing axial stop shoulder surface formed by an axially stepped coupler shoulder of an exterior circumscribing surface of the pipette tip coupler, the distally facing axial stop shoulder surface complementary to a proximally facing axial stop surface formed by an axially stepped shoulder surface of the interior circumscribing surface of the sidewall of the pipette tip; (3) providing a proximal elastomeric element carried by the pipette tip coupler at a location superior to the axially stepped coupler shoulder; (4) providing a distal elastomeric element carried by the pipette tip coupler at a location inferior to the axially stepped coupler shoulder; (5) locating a distal end of the pipette tip coupler over the open proximal end of the pipette tip with an axial alignment between a central longitudinal axis of the pipette tip coupler and a central longitudinal axis of the pipette tip; (6) translating the distal end of the pipette tip coupler through the open proximal end of the pipette tip until the distal elastomeric element contacts a circumferential radially inwardly angled and distally extending interior working surface of the interior circumscribing surface of the sidewall of the pipette tip distal from the axially stepped shoulder of the interior circumscribing surface of the sidewall of the pipette tip; and (7) axially squeezing the proximal elastomeric element into an axially compressed radially expanded state for extruding the primary O-ring into abutment with an upper axially arcuate circumferential surface sector portion of an axially arcuate circumferential interior surface defining a groove formed into the interior circumscribing surface of the sidewall of the pipette tip at a location superior to the axial stop surface of the pipette tip for providing a proximally directed radial and axial resultant pre-stress force to the pipette tip for energizing the distal elastomeric element into a compressed state configured for providing an axial and radial sealing abutment of the outer circumferential portion of the distal elastomeric element with the circumferential radially inwardly angled and distally extending interior working surface of the interior circumscribing surface of the sidewall of the pipette tip, and for abutting the proximally facing axial stop surface of the pipette tip with the distally facing axial stop surface of said pipette tip coupler body to define an axial coupling position of the pipette tip on the pipette tip coupler device.

Alternative Sealing Seat Surfaces

Figure 54:
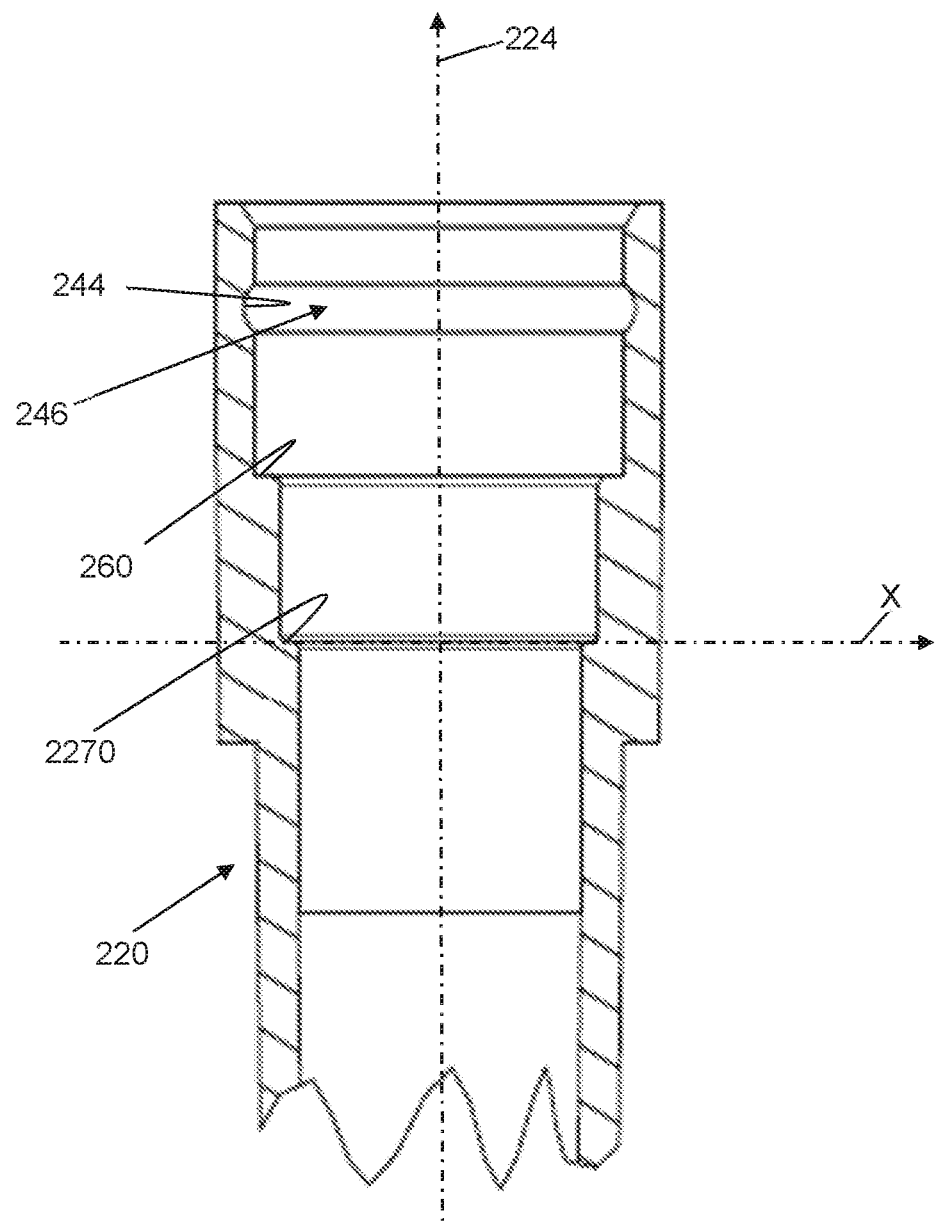
FIG. 54 is a fragmentary, longitudinal sectional, side elevational view of the example embodiment of the disposable pipette tip comprising an alternative sealing seat surface angle of substantially ninety degrees relative to the central longitudinal axis of the pipette tip.

In a further embodiment, FIG. 54 illustrates a fragmentary, longitudinal sectional, side elevational view of the example embodiment of the disposable pipette tip 220 comprising an alternative sealing seat surface 2270 having an angle of substantially ninety degrees relative to the central longitudinal axis 224 of the pipette tip 220.

Figure 55:
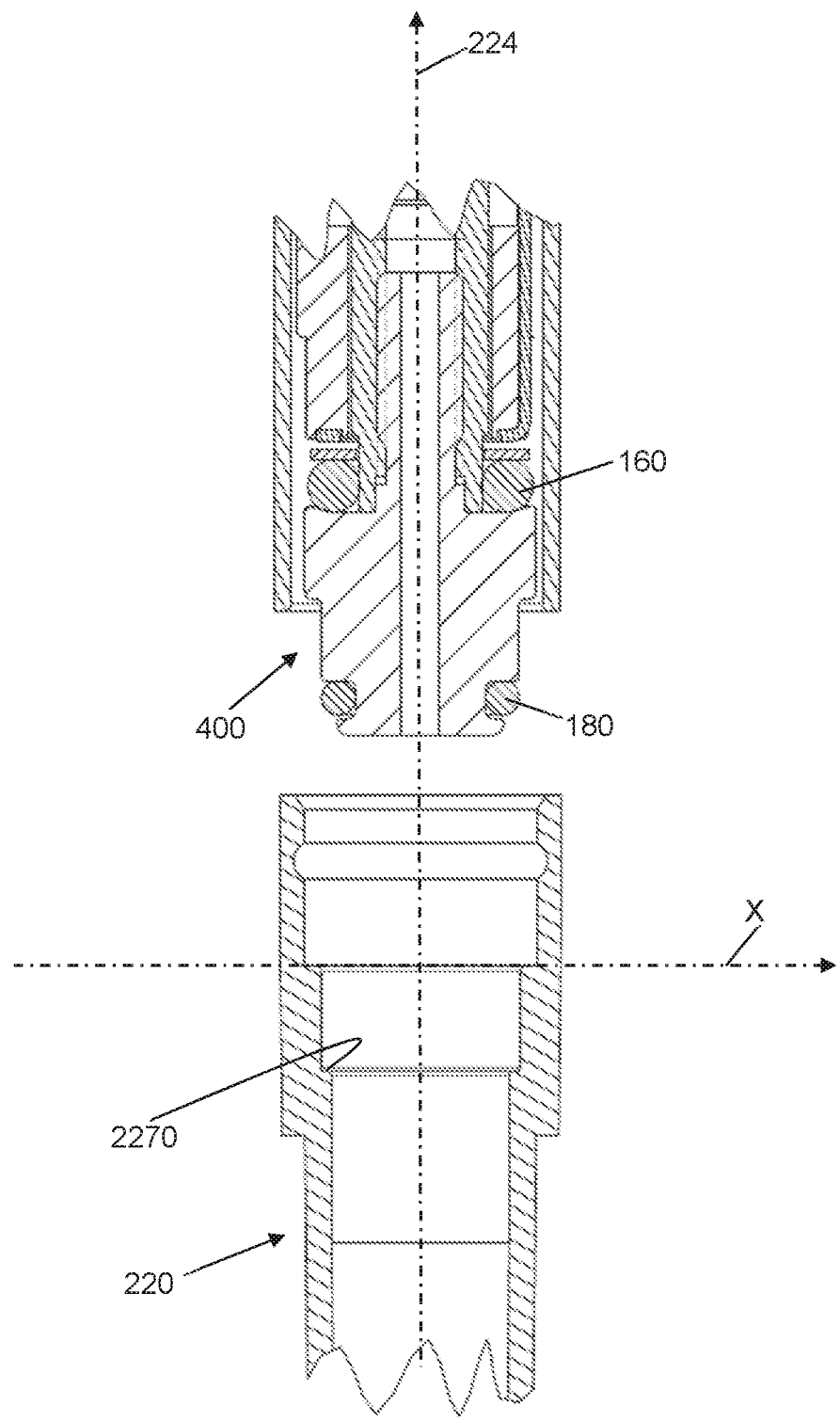
FIG. 55 is a fragmentary, longitudinal sectional, side elevational view of the second example embodiment of the pipette tip coupler device, which is initially illustrated in FIG. 34, axially aligned over the example embodiment of the disposable pipette tip comprising the alternative sealing seat surface angle of substantially ninety degrees.

FIG. 55 illustrates the second example embodiment of the pipette tip coupler device 400 positioned over and axially aligned with the example embodiment of the disposable pipette tip comprising the alternative sealing seat surface 2270.

Figure 56:
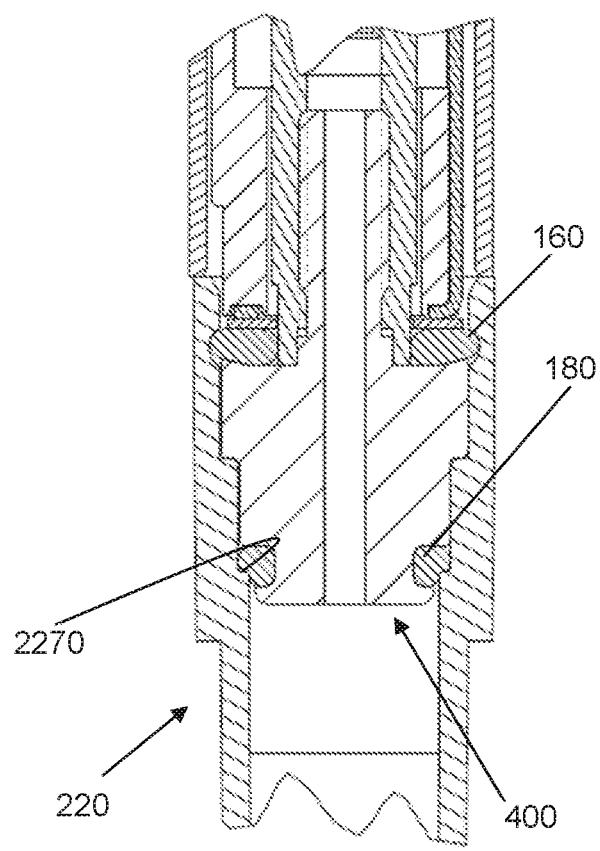
FIG. 56 is a fragmentary, longitudinal sectional, side elevational view of the second example embodiment of the pipette tip coupler device positioned in the disposable pipette tip comprising the alternative sealing seat surface angle of substantially ninety degrees wherein the tip is lifted up to its final seated state with the distal elastomeric element in a final compressed and seated sealing state against the sealing seat surface having the alternative sealing seat surface angle of substantially ninety degrees.

FIG. 56 illustrates the second example embodiment of the pipette tip coupler device 400 positioned in the disposable pipette tip 220 comprising the ninety-degree sealing seat surface 2270 wherein the tip 220 is lifted up to its final seated state with the distal elastomeric element 180 in a final compressed and seated sealing state against the sealing seat surface 2270 having the alternative sealing seat surface angle of substantially ninety degrees.

Figure 57:
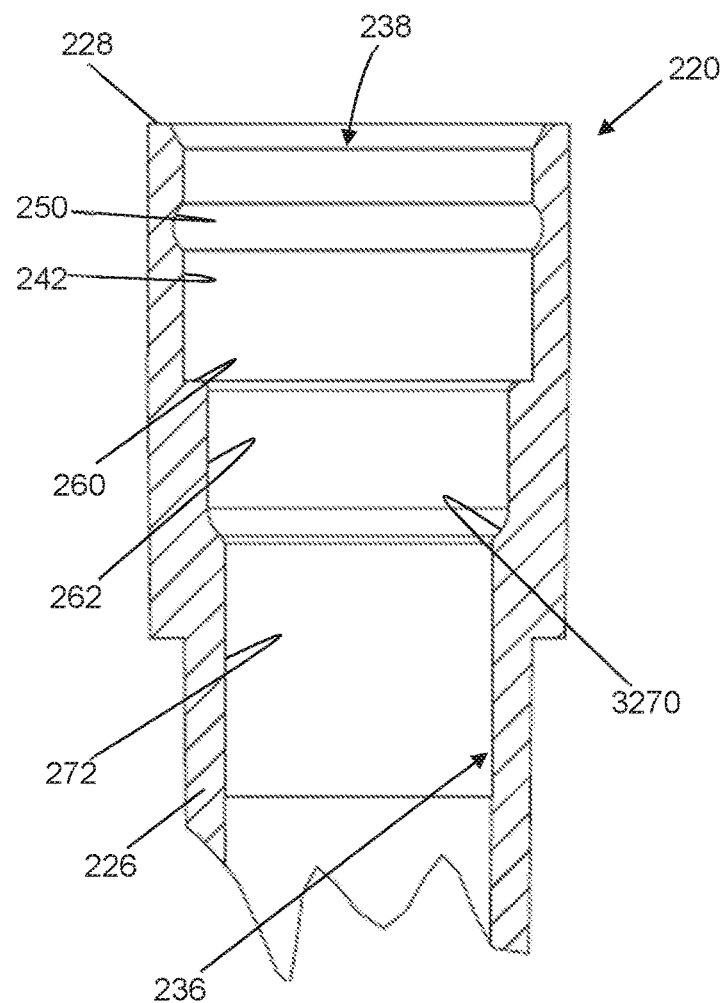
FIG. 57 is a fragmentary, longitudinal sectional, side elevational view of the upper interior of the example embodiment of the disposable pipette tip comprising another alternative sealing seat surface in the form of a circumferential radially concave sealing seat surface.
Figure 58:
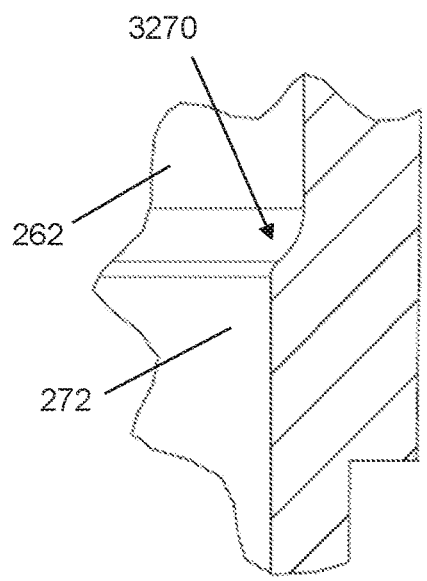
FIG. 58 is a fragmentary, longitudinal sectional, side elevational detailed view of the example embodiment of the disposable pipette tip illustrating detail of the circumferential radially concave sealing seat surface illustrated in FIG. 57.

In a further embodiment, FIG. 57 illustrates a fragmentary, longitudinal sectional, side elevational view of the upper interior of the example embodiment of the disposable pipette tip 220 comprising another alternative sealing seat surface in the form of a circumferential radially concave sealing seat surface 3270 that is further illustrated in detail in FIG. 58.

Figure 59:
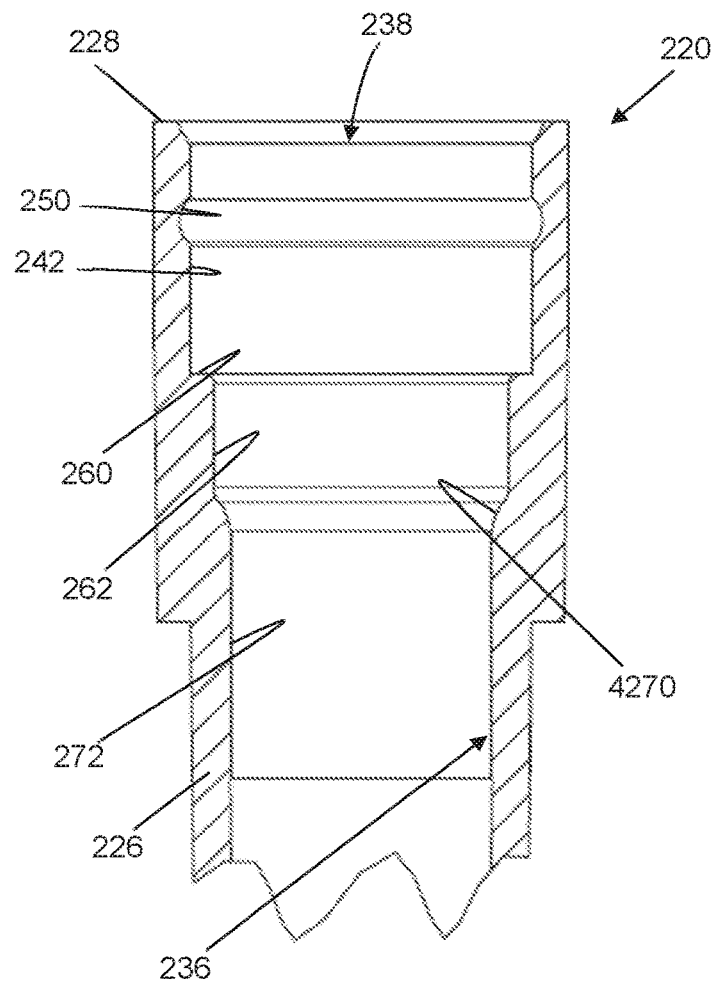
FIG. 59 is a fragmentary, longitudinal sectional, side elevational view of the example embodiment of the disposable pipette tip illustrating detail of a further alternative sealing seat surface in the form of a circumferential radially convex sealing seat surface.
Figure 60:
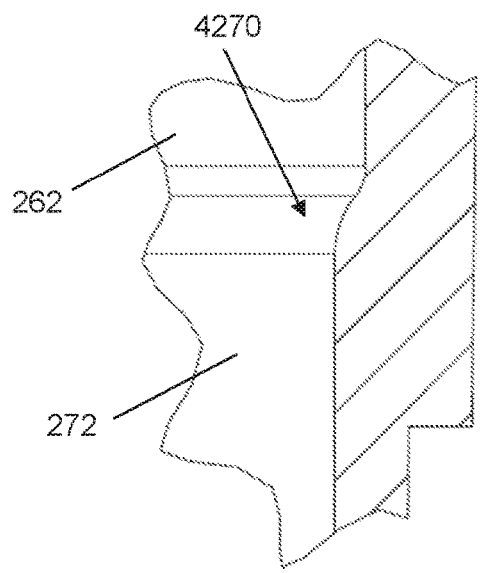
FIG. 60 is a fragmentary, longitudinal sectional, side elevational detailed view of the example embodiment of the disposable pipette tip illustrating detail of the circumferential radially convex sealing seat surface illustrated in FIG. 59.

FIG. 59 is a fragmentary, longitudinal sectional, side elevational view of the example embodiment of the disposable pipette tip 220 illustrating detail of a further alternative sealing seat surface in the form of a circumferential radially convex sealing seat surface 4270 that is further illustrated in detail in FIG. 60.

Figure 61:
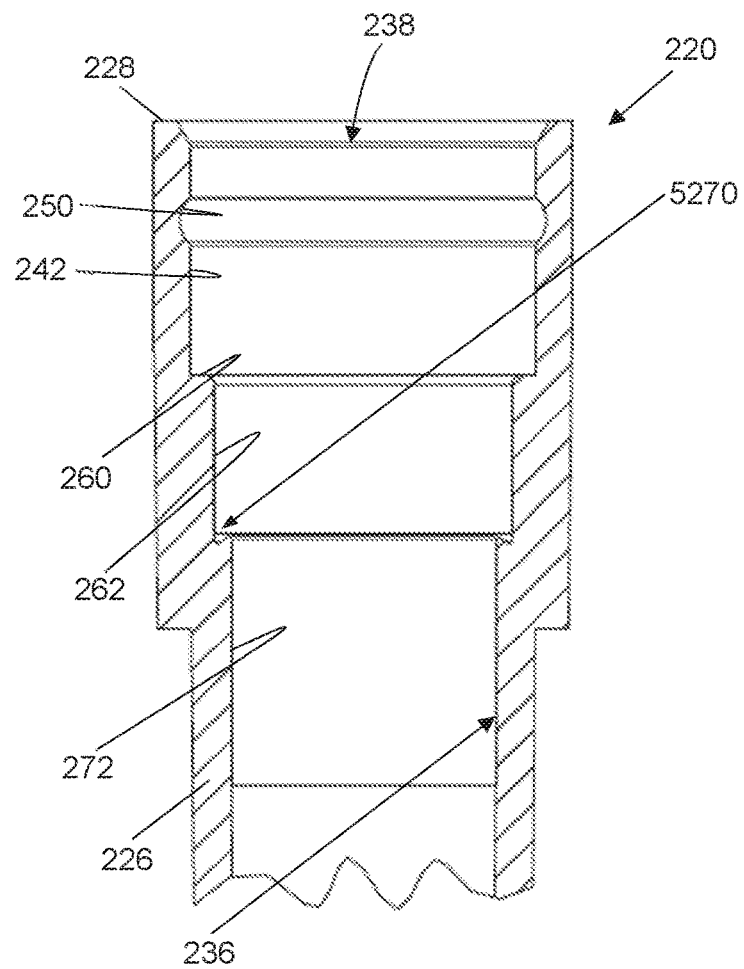
FIG. 61 is a fragmentary, longitudinal sectional, side elevational view of the example embodiment of the disposable pipette tip illustrating a yet further alternative sealing seat surface in the form of a circumferential upward facing tooth edge sealing seat surface.
Figure 62:
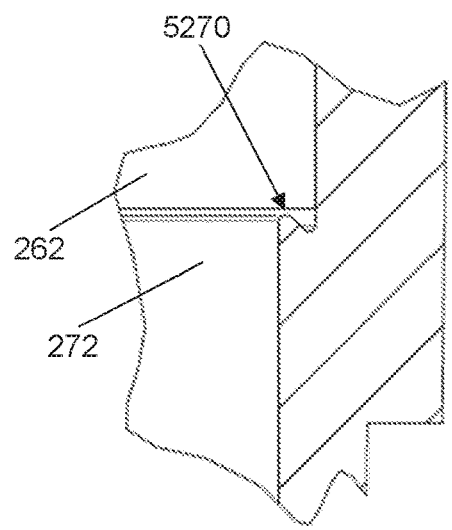
FIG. 62 is a fragmentary, longitudinal sectional, side elevational detailed view of the example embodiment of the disposable pipette tip illustrating detail of the circumferential upward facing tooth edge sealing seat surface illustrated in FIG. 61.

In a further embodiment, FIG. 61 illustrates a fragmentary, longitudinal sectional, side elevational view of the example embodiment of the disposable pipette tip 200 illustrating a yet further alternative sealing seat surface in the form of a circumferential upward facing tooth edge sealing seat surface 5270 that is further illustrated in detail in FIG. 62.

Alternative Groove Shapes

Figure 63:
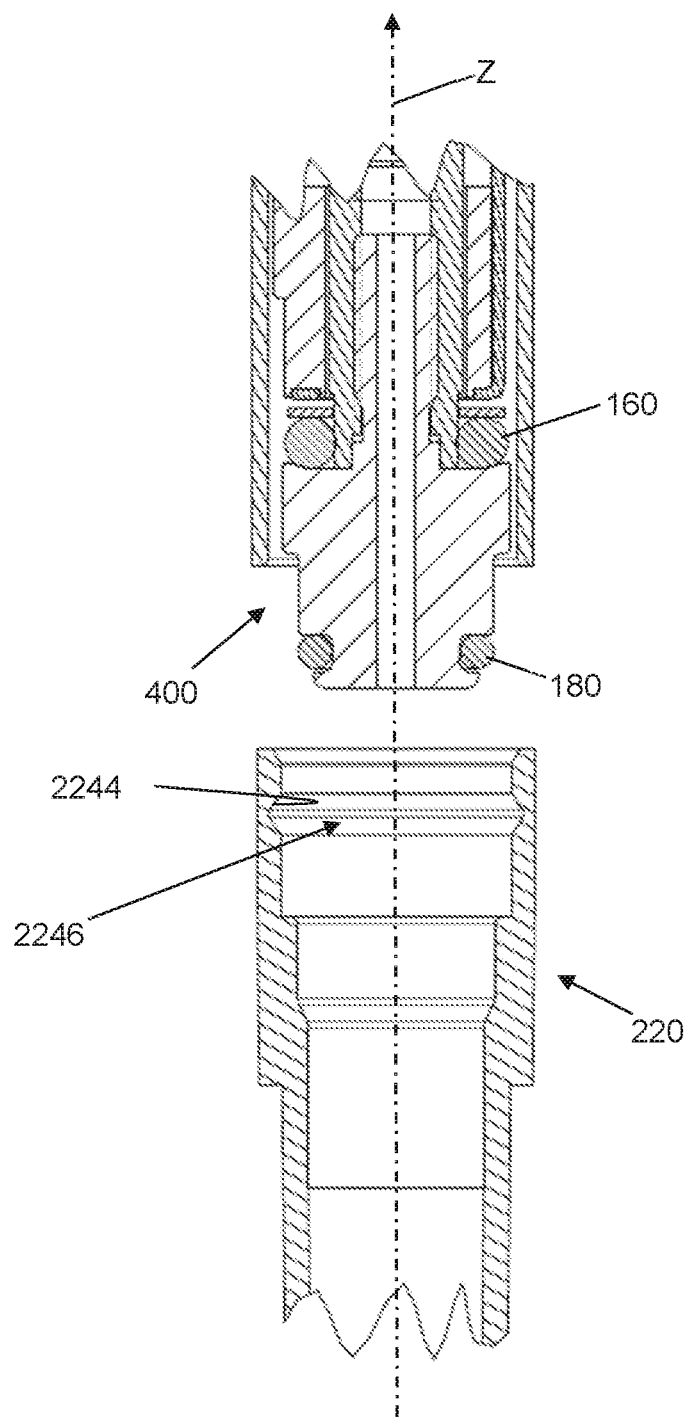
FIG. 63 is a fragmentary, longitudinal sectional, side elevational view of the second example embodiment of the pipette tip coupler device positioned over the example embodiment of the disposable pipette tip comprising an alternative circumferential annular tip groove in the form of a V-shaped groove defined by an V-shaped circumferential interior surface of the disposable pipette tip opening toward the longitudinal axis and having a V-shaped cross section as illustrated.

FIG. 63 illustrates pipette tip coupler device 400 positioned over the example embodiment of the disposable pipette tip 220 comprising an alternative circumferential V-shaped groove 2246 defined by an V-shaped circumferential interior surface 2244 of the disposable pipette tip 220 opening toward the longitudinal Z axis and having a V-shaped cross section as illustrated.

Figure 64:
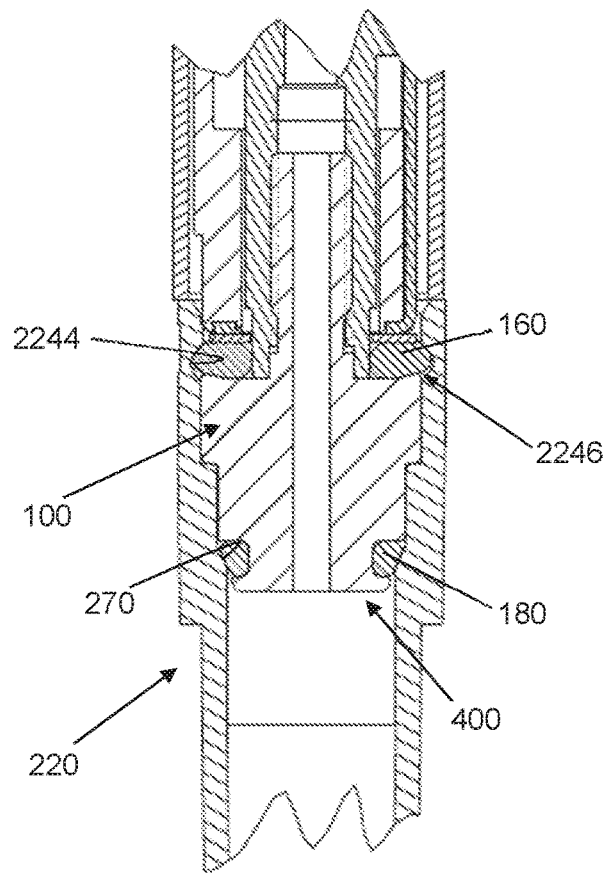
FIG. 64 is a fragmentary, longitudinal sectional, side elevational view of the second example embodiment the pipette tip coupler device positioned in the disposable pipette tip comprising the alternative V-shaped groove wherein the tip is lifted up to its final state with the primary O-ring being compressed and extruded into the V-shaped groove with abutment against the V-shaped circumferential interior surface and with the distal elastomeric element compressed and seated against the sealing seat surface of the tip.

FIG. 64 illustrates the pipette tip coupler device 400 being located in the disposable pipette tip 220 comprising the alternative V-shaped groove 2246 wherein the tip 220 with the alternative V-shaped groove 2246 is lifted up to its final state with the primary elastomeric element 160 being compressed and extruded into the V-shaped groove 2246 and into abutment against the V-shaped circumferential interior surface 2244 with the secondary elastomeric element 180 in the final compressed and seated sealing state against the sealing seat surface 270 of the tip 220.

Figure 65:
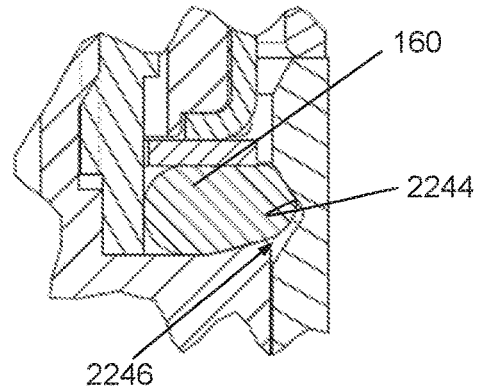
FIG. 65 is a fragmentary, longitudinal sectional, side elevational detailed view of the primary O-ring being in the final state of being compressed and extruded into the V-shaped groove as is illustrated in FIG. 64.
Figure 66:
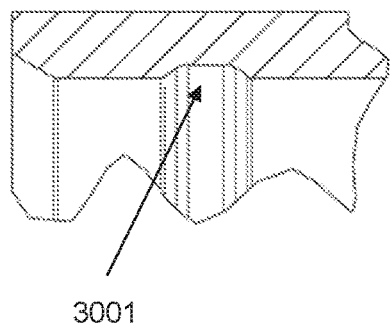
FIGS. 66 through 76 are fragmentary, longitudinal sectional, side elevational views detailing further example embodiments of different circumferential annular tip groove configurations.
Figure 67:
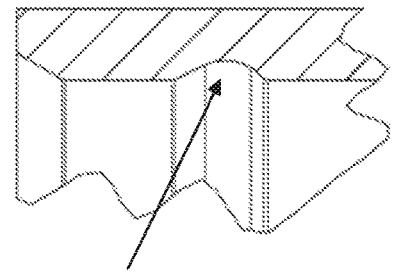
Figure 68:
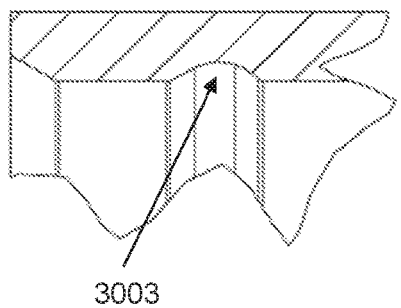
Figure 69:
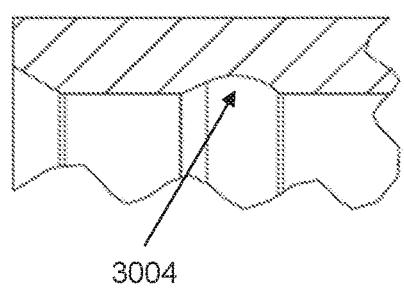
Figure 70:
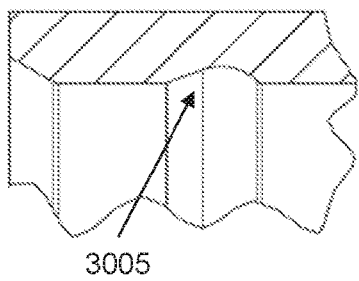
Figure 71:
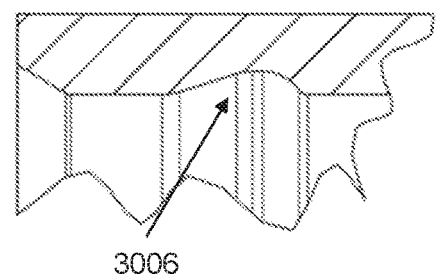
Figure 72:
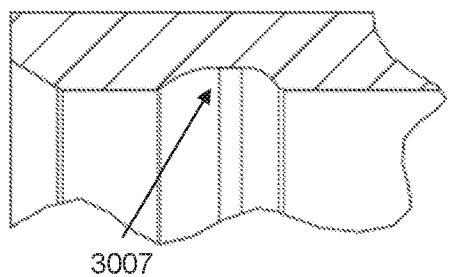
Figure 73:
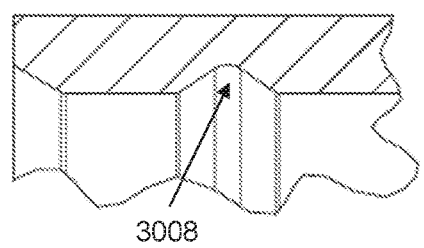
Figure 74:
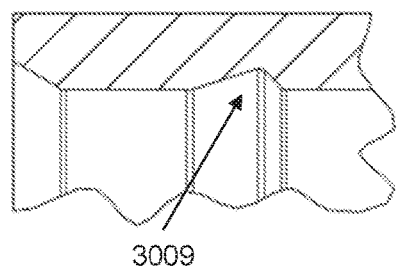
Figure 75:
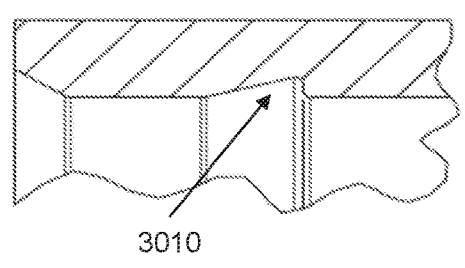

FIG. 65 illustrates the detail of the primary O-ring 160 being in the final state of being compressed and extruded into the V-shaped groove 2246 and into abutment against the V-shaped circumferential interior surface 2244.

Furthermore, FIGS. 66 through 76 illustrate fragmentary, longitudinal sectional, side elevational views detailing further different alternative example embodiments of the circumferential annular tip groove 246 illustrated in FIG. 15. In particular, FIGS. 66 through 76 illustrate respective groove configurations 3001, 3002, 3003, 3004, 3005, 3006, 3007, 3008, 3009, 3010, and 3011. Additionally, the segments of the couplers may comprise radially outwardly extending faces complementary to the respective different alternative example embodiments of the respective groove configurations 3001 through 3011.

Figure 76:
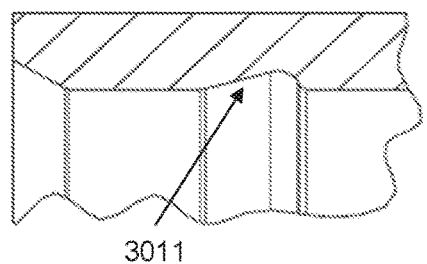

Moreover, any one of the sealing seat geometries 270 (FIG. 15), 2270 (FIG. 54), 3270 (FIG. 57), 4270 (FIG. 59), or 5270 (FIG. 61) may be employed with any one of the circumferential annular tip groove geometries 246 (FIG. 15), 2246 (FIG. 63), 3001 (FIG. 66), 3002 (FIG. 67), 3003 (FIG. 68), 3004 (FIG. 69), 3005 (FIG. 70), 3006 (FIG. 71), 3007 (FIG. 72), 3008 (FIG. 73), 3009 (FIG. 74), 3010 (FIG. 75), or 3011 (FIG. 76). Moreover, the elastomeric element 160 may also have shapes alternate to an O-ring shape and may be in the form of, but not limited to, configurations complementary to any one of the tip sealing seat geometries.

Devoid of Groove/Interruption

Figure 77:
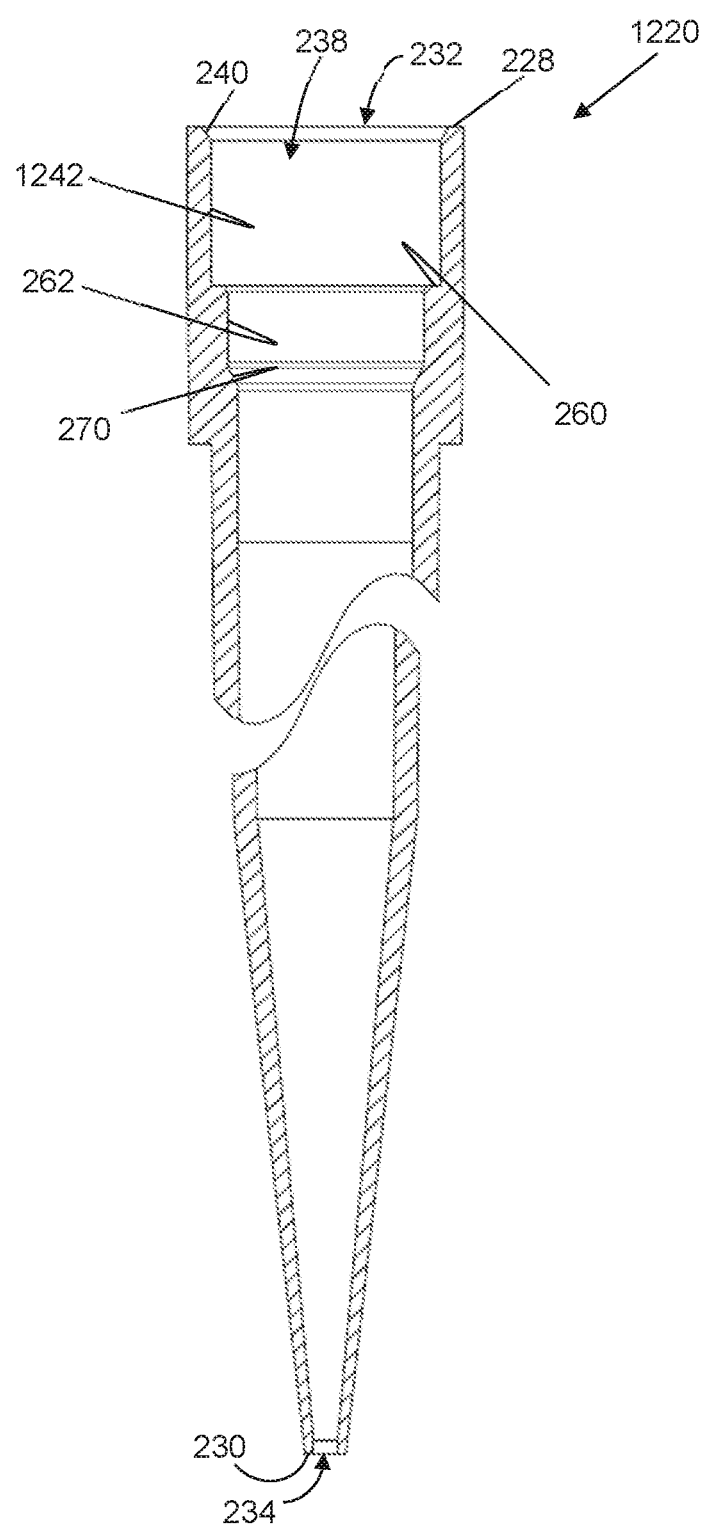
FIG. 77 is a fragmentary, longitudinal sectional, side elevational detailed view detailing an interior of a second example embodiment of a disposable pipette tip.

FIG. 77 illustrates an interior of a second example embodiment of a disposable pipette tip in the form of disposable pipette tip 1220. Disposable pipette tip 1220 is analogous in all portions to disposable pipette tip 220 with the exception that interrupted interior surface section 242 is devoid of interruption such as a groove thereby defining uninterrupted interior surface section 1242 of the disposable pipette tip 1220. Disposable pipette tip 1220 can also alternatively employ one of the alternative sealing seat geometries 270 (FIG. 15), 2270 (FIG. 54), 3270 (FIG. 57), 4270 (FIG. 59), or 5270 (FIG. 61). Disposable pipette tip 1220 can also be used with pipette tip coupler 100, pipette tip coupler 400, or pipette tip coupler 500.

Figure 78:
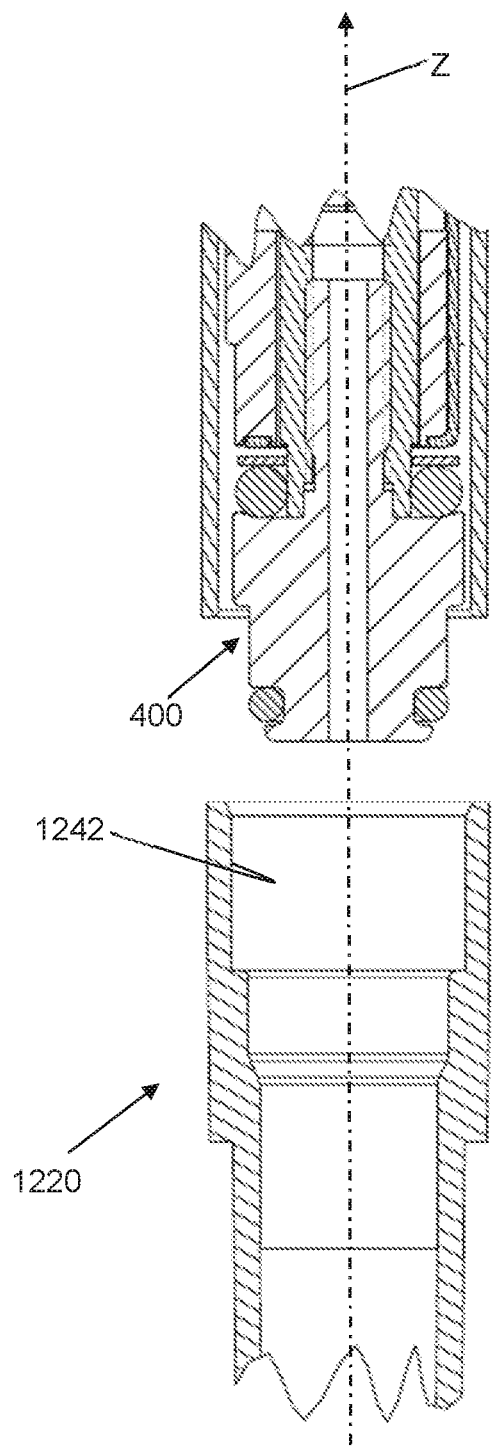
FIG. 78 is a fragmentary, longitudinal sectional, side elevational view of the second example embodiment of the pipette tip coupler device positioned over the second example embodiment of the disposable pipette tip.

FIG. 78 illustrates the pipette tip coupler device 400 aligned over the disposable pipette tip 1220 comprising the uninterrupted interior surface section 1242.

Figure 79:
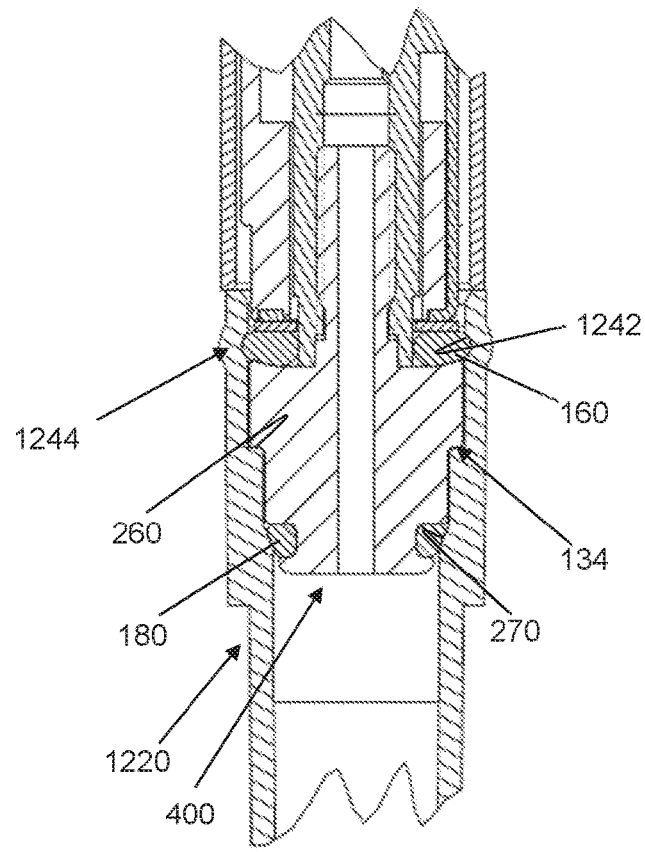
FIG. 79 is a fragmentary, longitudinal sectional, side elevational view of the second example embodiment of the pipette tip coupler device positioned in the second example embodiment of the disposable pipette tip with a stop disk shoulder surface of the second example embodiment of the pipette tip coupler device abutting against an axial stop surface of the second example embodiment of the disposable pipette tip, with the primary O-ring being compressed against an interior surface of a circumscribing sidewall of the second example embodiment of the disposable pipette tip resulting in a deformation of the interior surface, and with the distal elastomeric element in a final compressed and seated sealing state against a sealing seat surface of the second example embodiment of the disposable pipette tip.
Figure 80:
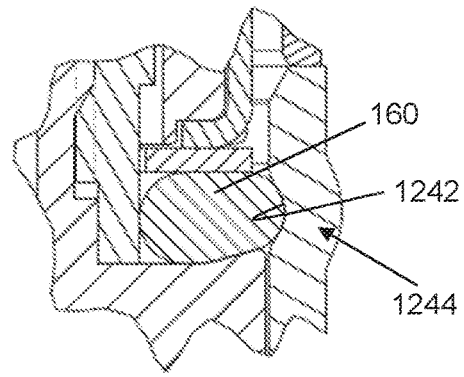
FIG. 80 is a fragmentary, longitudinal sectional, side elevational detailed view of the primary O-ring of the second example embodiment of the pipette tip coupler device being compressed against and deforming the circumscribing sidewall of the second example embodiment of the disposable pipette tip.

FIG. 79 illustrates the pipette tip coupler device 400 positioned in the disposable pipette tip 1220 with the stop shoulder surface 134 of the coupler device 400 abutting against the axial stop surface 260 of disposable pipette tip 1220.

Additionally, FIG. 79 illustrates the primary O-ring 160 being compressed against the interior surface 1242 of the circumscribing sidewall of the disposable pipette tip 1220 resulting in a deformation 1244 of the interior surface 1242 of the disposable pipette tip 1220. FIG. 79 further illustrates the distal elastomeric element 180 in the final compressed and seated sealing state against the sealing seat surface 270 of the disposable pipette tip 1220.

Accordingly, the first working surface is in the form of, but not limited to, one of the respective groove configuration detailed above or an uninterrupted configuration exemplified by the uninterrupted interior surface section 1242 (FIG. 78) of the disposable pipette tip 1220.

Shoulder Seat Surface Comprising Axially Upwardly Projecting Rib 5020

Figure 81:
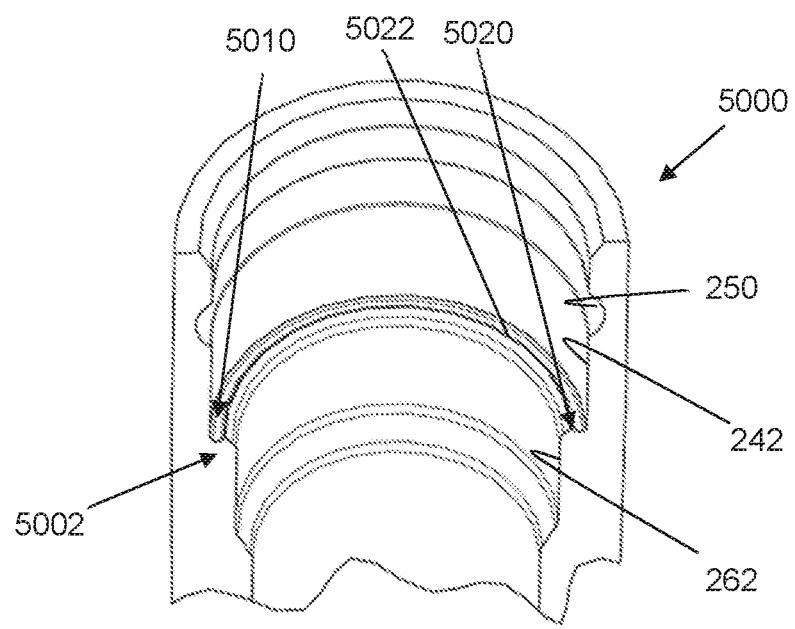
FIG. 81 is an upper fragmentary, longitudinal sectional, top and side perspective view detailing an upper interior of a further example embodiment of a disposable pipette tip comprising an interior axially upwardly facing shoulder seat surface having an axially upwardly facing annular groove coaxially disposed around an interior axially upwardly extending circumscribing rib.
Figure 82:
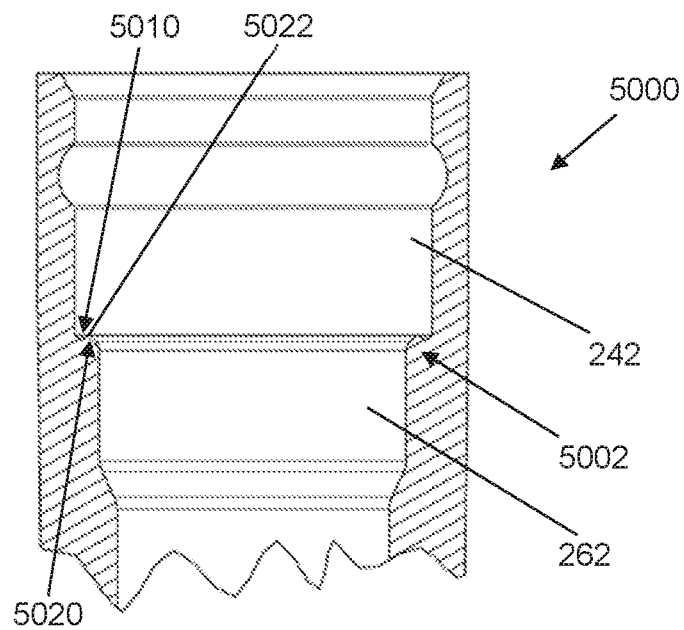
FIG. 82 is a fragmentary, longitudinal sectional, side elevational view of the further example embodiment of the disposable pipette tip comprising the interior axially upwardly facing shoulder seat surface having the axially upwardly facing annular groove coaxially disposed around the interior axially upwardly extending circumscribing rib having a continuous solid circumscribing cross section.

In another example embodiment, FIGS. 81 and 82 detail an upper interior of a disposable pipette tip 5000 that is analogous in all portions to disposable pipette tip 220 (FIG. 15) with the exception of an alternative interior axially upwardly facing shoulder seat surface having an axially upwardly facing annular groove 5010 coaxially disposed around an axially upwardly extending circumscribing rib 5020 having a continuous solid circumscribing cross section.

As illustrated in FIGS. 81 and 82, the first substantially cylindrical interior surface section 242 is axially distally proceeded by the second substantially cylindrical interior surface section 262 having a second diameter less than the first diameter of the first substantially cylindrical interior surface section 242 for forming the proximally facing, radially inwardly extending annular shoulder 5002 comprising the axially upwardly facing annular groove 5010 coaxially disposed around the axially upwardly extending circumscribing rib 5020.

Figure 83:
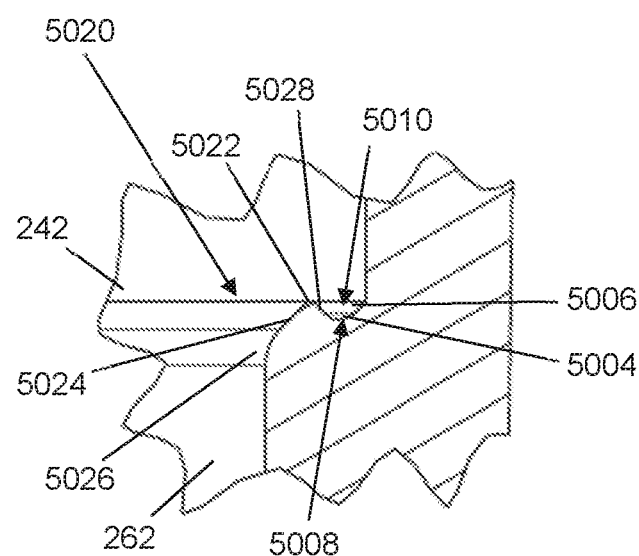
FIG. 83 is a fragmentary, longitudinal sectional, side elevational detailed view of the further example embodiment of the disposable pipette tip illustrating detail of the axially upwardly facing annular groove coaxially disposed around the interior axially upwardly extending circumscribing rib.

In one embodiment, and as illustrated in FIG. 83, the axially upwardly extending circumscribing rib 5020 comprises an uppermost rib seat surface or rib apex 5022 transitioning into sloping rib side surfaces 5024 and 5028. Sloping rib side surface 5024 transitions into an annular convex surface 5026 that transitions to the second substantially cylindrical interior surface section 262. On the outer radial side of the circumscribing rib 5020, sloping side surface 5028 forms a side wall surface of a groove surface 5008 defining the groove 5010. The groove surface 5008 further comprises a lower surface 5004 that transitions between the side surface 5028 and a sloping side surface 5006 that transitions into the first substantially cylindrical interior surface section 242.

In one embodiment, and referring to FIGS. 81 through 83, the axially upwardly extending circumscribing rib 5020 comprising the rib apex 5022 may be formed by, for example, the removal of material from the upper surface of the proximally facing, radially inwardly extending annular shoulder to form the groove 5010 or by the upper surface of the proximally facing, radially inwardly extending annular shoulder being molded to be devoid of material to form the groove 5010.

Figure 84:
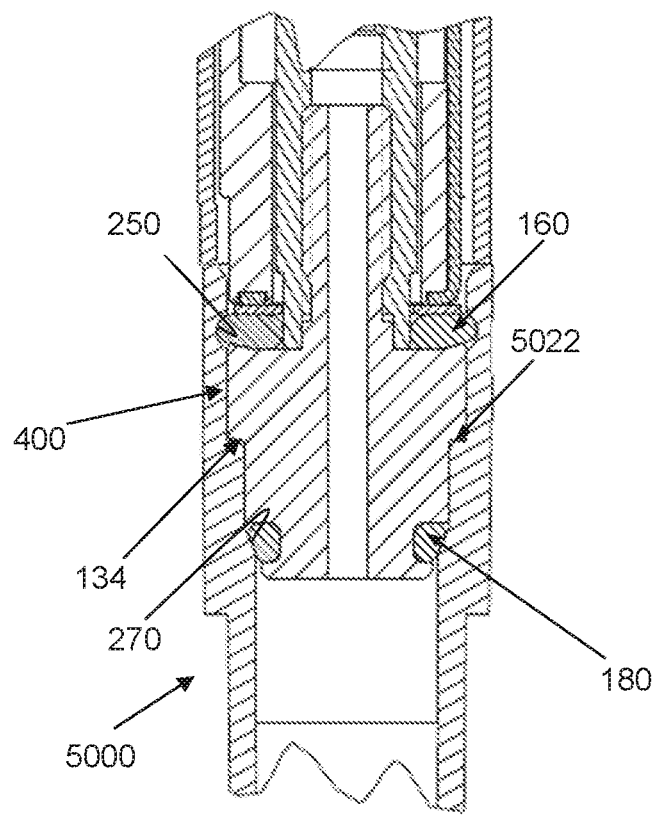
FIG. 84 is a fragmentary, longitudinal sectional, side elevational view of the second example embodiment of the pipette tip coupler device operatively positioned in the further example embodiment of the disposable pipette tip comprising the interior axially upwardly extending circumscribing rib.
Figure 85:
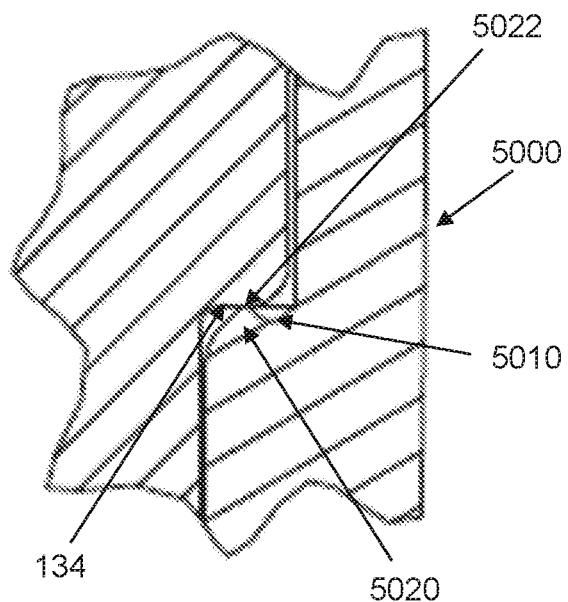
FIG. 85 is a fragmentary, longitudinal sectional, side elevational detailed view of a distally facing axial stop shoulder surface of the second example embodiment of the pipette tip coupler device abutting the interior axially upwardly extending circumscribing rib of the further example embodiment of the disposable pipette tip.

Referring to FIGS. 84 and 85, the disposable pipette tip 5000 can be used with one of the pipette tip coupler devices described above such as pipette tip coupler device 400 wherein reducing the proximally facing surface area of the radially inwardly extending annular shoulder 5002 by forming rib apex 5022 provides an increase in the pressure between the tip 5000 and the stop shoulder surface 134 of the pipette tip coupler device 400.

Specifically, and referring to FIGS. 41, 84, and 85, the axial force (Fprimary_axial) produced by the primary O-ring 160 engaging the groove 250 will push against the rib apex 5022 thereby producing a seal between the tip 5000 and surface 134. Since pressure (P) is equal to force (F) divided by area (A), reducing the surface area of the radially inwardly extending annular shoulder by providing the rib apex 5022 results in increased pressure (P=F/A). This increased pressure between the tip 5000 at the rib apex 5022 and surface 134 provides a seal. Accordingly, the disposable pipette tip 5000 provides a new seal for every use. In alternative embodiments, circumscribing rib 5022 may also be provided by a sealant bead, elastomer washer, O-ring, or other means to provide a configuration exemplified by rib 5022.

Internal Seal Pipette Tip Assembly 6010

Figure 86:
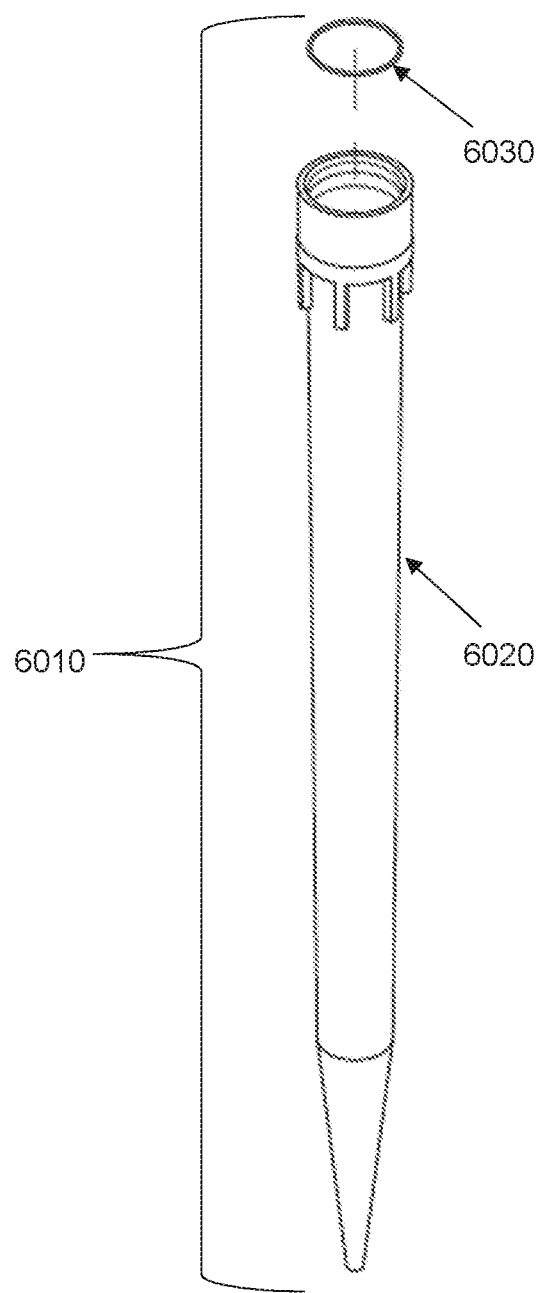
FIG. 86 is an exploded parts perspective view of an example embodiment of an internal seal pipette tip assembly comprising an internal seal pipette tip and an internal seal.

In another example embodiment, FIG. 86 illustrates an example embodiment of an internal seal pipette tip assembly 6010 comprising an internal seal pipette tip 6020 and an internal seal 6030.

Figure 87:
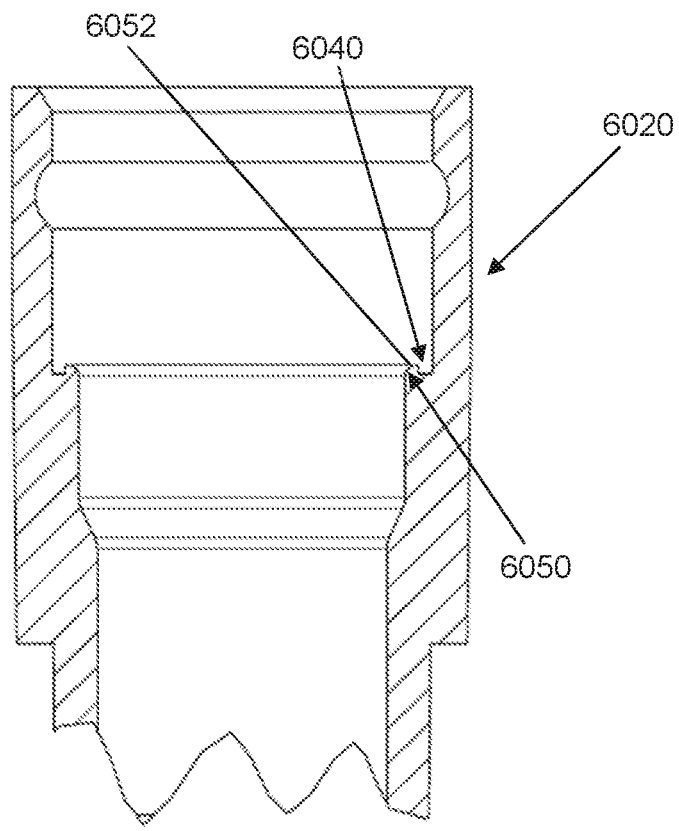
FIG. 87 is an upper fragmentary, longitudinal sectional, side elevational view detailing an upper interior of the example embodiment of the internal seal pipette tip comprising an interior axially upwardly facing shoulder seat surface having an axially upwardly facing annular groove coaxially disposed around a radially interior axially upwardly extending circumscribing rib having a continues solid circumscribing cross section.

Referring to FIGS. 86 and 87, the pipette tip 6020 is analogous in all portions to disposable pipette tip 220 (FIG. 15) with the exception of an alternative interior axially upwardly facing shoulder seat surface having an axially upwardly facing annular groove 6040 coaxially disposed around an axially upwardly extending circumscribing rib 6050 having an uppermost rib seat surface or rib apex 6052.

Figure 88:
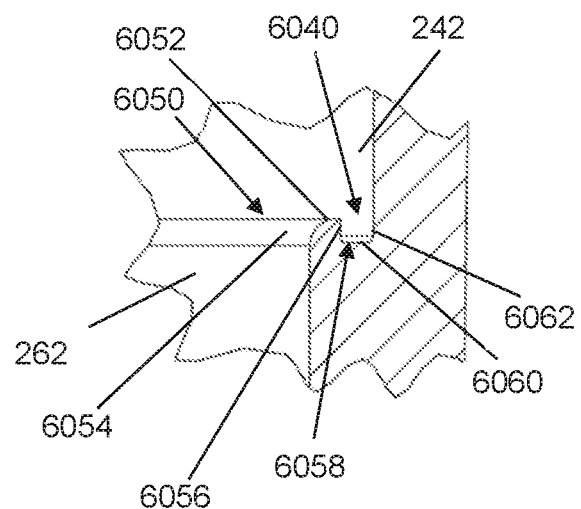
FIG. 88 is a fragmentary, longitudinal sectional, side elevational detailed view of the example embodiment of the internal seal pipette tip illustrating detail of the axially upwardly facing annular groove coaxially disposed around the radially interior axially upwardly extending circumscribing rib.

As illustrated in detail in FIG. 88, axially upwardly extending circumscribing rib 6050 comprises an uppermost rib seat surface or rib apex 6052 transitioning into an annular convex surface 6054 on the radially inner side of the rib apex 6052 and transitioning into a step side surface 6056 on the radially outer side of the rib apex 6052. Convex surface 6054 transitions into the second substantially cylindrical interior surface section 262 and step side surface 6056 forms a side wall surface of a groove surface 6058 defining the groove 6040. The groove surface 6058 further comprises a lower surface 6060 that transitions between the side surface 6056 and an axially upwardly extending side surface 6062 that transitions into the first substantially cylindrical interior surface section 242.

Figure 89:
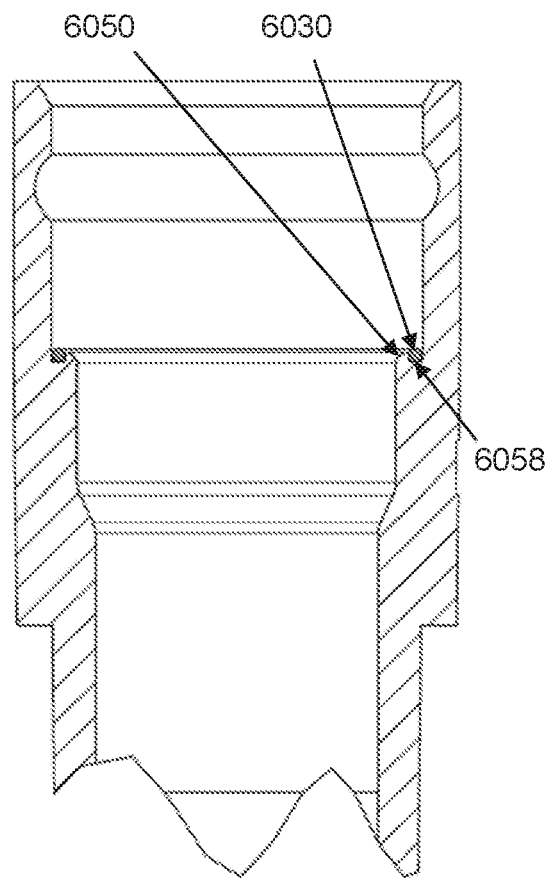
FIG. 89 is a fragmentary, longitudinal sectional, side elevational view of the example embodiment of the internal seal pipette tip assembly comprising the internal seal disposed in the axially upwardly facing annular groove.

As illustrated in FIG. 89, the internal seal 6030 is configured to be disposed for compression in the axially upwardly facing annular groove 6040 (FIG. 88) defined by groove surface 6058.

Figure 90:
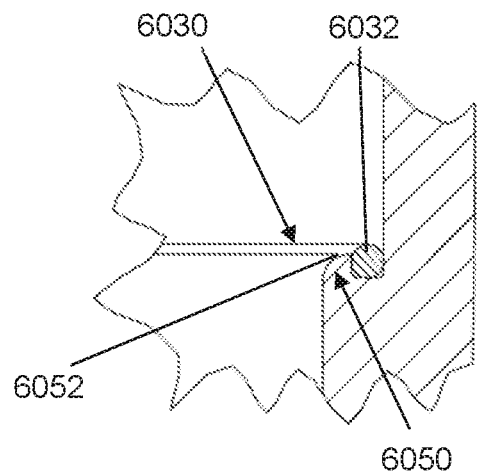
FIG. 90 is a fragmentary, longitudinal sectional, side elevational detailed view of the internal seal disposed in the axially upwardly facing annular groove.

Additionally, and as illustrated in FIG. 90, the internal seal 6030 is further configured to comprise in its uncompressed state an axially upwardly extending circumscribing sector portion 6032 having an axial elevation greater than the axial elevation of the circumscribing rib apex 6052 of the axially upwardly extending circumscribing rib 6050.

Figure 91:
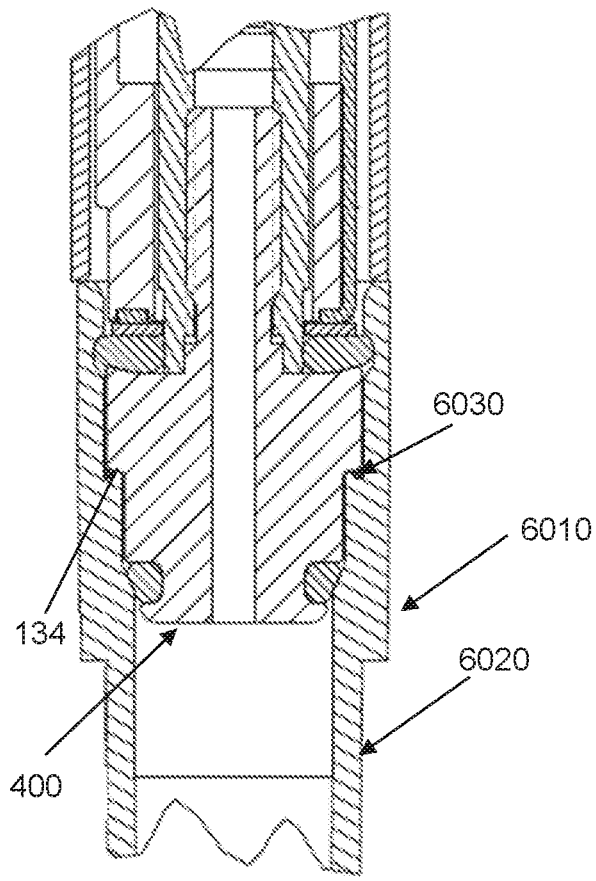
FIG. 91 is a fragmentary, longitudinal sectional, side elevational view of the second example embodiment of the pipette tip coupler device positioned in and operatively coupled to the example embodiment of the internal seal pipette tip assembly.
Figure 92:
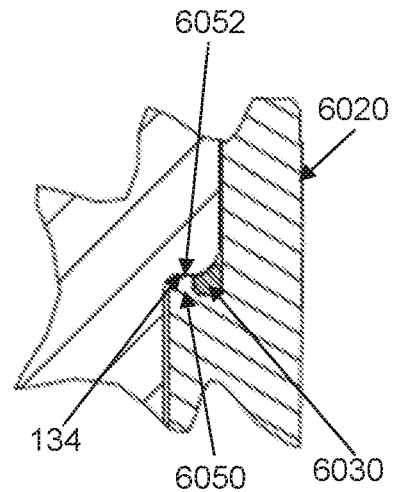
FIG. 92 is a fragmentary, longitudinal sectional, side elevational detailed view of a distally facing axial stop shoulder surface of the second example embodiment of the pipette tip compressing the internal seal disposed in the axially upwardly facing annular groove and contacting the radially interior axially upwardly extending circumscribing rib disposed coaxially within and radially adjacent to the axially upwardly facing annular groove.

The internal seal pipette tip assembly 6010 can be used with any of the pipette tip coupler devices described above such as pipette tip coupler device 400 as is illustrated in FIG. 91 wherein the pipette tip coupler device 400 is positioned in and operatively coupled to the internal seal pipette tip assembly 6010 comprising the internal seal pipette tip 6020 and the internal seal 6030. With the pipette tip coupler device 400 operatively coupled to the internal seal pipette tip assembly 6010 the distally facing axial stop shoulder surface 134 of the pipette tip coupler device 400 compresses the internal seal 6030 disposed in the axially upwardly facing annular groove 6040 (FIG. 88) to the extent of contact between the distally facing axial stop shoulder surface 134 and the rib apex 6052 of the axially upwardly extending circumscribing rib 6050 as illustrated in detail in FIG. 92. Once the tip assembly 6010 and the pipette tip coupler device 400 are operatively coupled together, the internal seal 6030 provides a seal between the tip 6020 and the pipette tip coupler device 400.

Accordingly, the internal seal pipette tip assembly 6010 provides a new internal seal 6030 for every use. Additionally, the internal seal 6030 provides a secondary sealing function and, in one embodiment, a replacement seal for distal seal 180. In one embodiment, the internal seal 6030 may be molded in place during the molding operation of the tip 6020. In other example embodiments, the internal seal 6030 may comprise another sealing mechanism, such as elastomeric element such as an O-ring, elastomeric washer, a thin layer of sealant, a sealant bead, an adhesive, or other sealant material or mechanism.

In light of the present disclosure as set forth above, structural modifications and adaptations may be resorted to without departing from the scope and fair meaning of the embodiments of the present disclosure as set forth above. For example, FIGS. 66 through 76 are views detailing different alternative example embodiments to the circumferential annular tip groove 246 illustrated in at least in FIG. 15. In particular, FIGS. 66 through 76 illustrate groove configurations 3001, 3002, 3003, 3004, 3005, 3006, 3007, 3008, 3009, 3010, and 3011 respectively.

Additionally, the primary O-ring 160 may comprise a radially outward face shaped complementary to any one of the embodiments of the respective groove configurations 3001 through 3011.

Furthermore, the tip distal O-ring sealing seat 270 may have different geometries in the form of, but not limited to, the sealing seat geometries 2270 (FIG. 54), 3270 (FIG. 57), 4270 (FIG. 59), or 5270 (FIG. 61).

Moreover, the distal O-ring 180 may have alternate shapes other than an O-ring and may be in the form of, but not limited to, configurations complementary to the geometry of one of the distal O-ring sealing seats 270 (FIG. 15), 2270 (FIG. 54), 3270 (FIG. 57), 4270 (FIG. 59), or 5270 (FIG. 61).

INDUSTRIAL APPLICABILITY

The above delineation of the systems, assemblies, devices, and methods including uses and operations, demonstrate the industrial applicability of embodiment(s) of the present disclosure.

In light of the present disclosure as set forth above, it should be apparent that further numerous structural modifications and adaptations may be resorted to without departing from the scope and fair meaning of the embodiments of the present disclosure as set forth hereinabove and as described hereinbelow by the claims. Hence, the spirit and scope of the appended claims should not be limited to the above delineated description of the embodiments of the present disclosure. And, in the appended claims reference to an element in the singular is not intended to mean "one and only one" unless explicitly so stated, but rather "one or more." Moreover, it is not necessary for a device or method to address each and every problem sought to be solved by the present disclosure, for it to be encompassed by the present claims.

What is claimed is:

1. A pipette tip coupling device and pipette tip assembly comprising:
    a pipette tip comprising a circumscribing sidewall with an open interior passage extending along a central longitudinal axis of the pipette tip between an open proximal end and an open distal end;
    a pipette tip coupling device comprising:
        a shank having a proximal end face;
        a coupler body having a proximal coupler end surface, wherein the coupler body is distal to the shank, and wherein a diameter of a widest portion of the coupler body is greater than a diameter of a widest portion of the shank;
        a distal stem portion comprising:
            a proximal neck; and
            a distal end plate;
        an open-ended interior circumscribing surface forming an open passageway extending longitudinally from the proximal end face through the distal end plate;
        a proximal elastomeric element, the proximal elastomeric element disposed around the shank and adjacent to the proximal coupler end surface; and
        a distal elastomeric element, the distal elastomeric element disposed around the proximal neck of the distal stem portion and adjacent to the distal end plate of the distal stem portion;
    wherein the proximal elastomeric element abuts against a first inner surface of the circumscribing sidewall of the pipette tip for securing the pipette tip to the pipette tip coupling device, and wherein the distal elastomeric element abuts against a second inner surface of the circumscribing sidewall of the pipette tip to form a seal between the pipette tip coupling device and the pipette tip.

2. The pipette tip coupling device and pipette tip assembly of claim 1 wherein the coupler body further comprises:
    a proximal cylindrical portion;
    a distal cylindrical portion; and
    wherein a diameter of the proximal cylindrical portion is greater than a diameter of the distal cylindrical portion, forming a distally facing stop shoulder surface.

3. The pipette tip coupling device and pipette tip assembly of claim 2 wherein the diameter of the distal cylindrical portion of the coupler body is greater than a diameter of the distal end plate of the distal stem portion.

4. The pipette tip coupling device and pipette tip assembly of claim 1 wherein the shank further comprises:
    an elongated tubular body distal to the proximal end face;
    a cylindrical neck distal to the elongated tubular body; and
    wherein a diameter of the cylindrical neck is less than a diameter of the elongated tubular body.

5. The pipette tip coupling device and pipette tip assembly of claim 4 wherein the shank further comprises a cylindrical collar distal to the cylindrical neck, wherein a diameter of the cylindrical collar is greater than the diameter of the cylindrical neck.

6. The pipette tip coupling device and pipette tip assembly of claim 4 wherein the shank further comprises a chamfered section between the proximal end face and the elongated tubular body.

7. The pipette tip coupling device and pipette tip assembly of claim 2 wherein the shank further comprises:
    an elongated tubular body distal to the proximal end face;
    a cylindrical neck distal to the elongated tubular body; and
    wherein a diameter of the cylindrical neck is less than a diameter of the elongated tubular body.

8. The pipette tip coupling device and pipette tip assembly of claim 1 further comprising an annular planar squeeze ring movably circumscribing the shank and proximal to the proximal elastomeric element.

9. The pipette tip coupling device and pipette tip assembly of claim 8 wherein the proximal elastomeric element, the pipette tip, and the annular planar squeeze ring each further comprises an electrically conductive material.

10. The pipette tip coupling device and pipette tip assembly of claim 1 further comprising an annular wedge movably circumscribing the shank and proximal to the proximal elastomeric element, the annular wedge comprising:
    a proximal wedge surface;
    a distal wedge surface, wherein a circumference of the proximal wedge surface is larger than a circumference of the distal wedge surface;
    an exterior surface, wherein the exterior surface connects the proximal wedge surface with the distal wedge surface; and
    wherein the exterior surface of the annular wedge abuts against the proximal elastomeric element.

11. The pipette tip coupling device and pipette tip assembly of claim 10 wherein the proximal wedge surface of the annular wedge further comprises a radially extending annular lip.

12. The pipette tip coupling device and pipette tip assembly of claim 10 wherein the proximal elastomeric element, the pipette tip, and the annular wedge each further comprises an electrically conductive material.

13. The pipette tip coupling device and pipette tip assembly of claim 1 wherein the pipette tip coupling device further comprises an annular spacer circumscribing the shank.

14. The pipette tip coupling device and pipette tip assembly of claim 1 wherein the proximal elastomeric element comprises an O-ring; and
    wherein the distal elastomeric element comprises an O-ring.

15. The pipette tip coupling device and pipette tip assembly of claim 1 wherein the proximal coupler end surface comprises a flat planar surface substantially perpendicular to the shank.

16. The pipette tip coupling device and pipette tip assembly of claim 1 wherein the proximal coupler end surface comprises:
    a substantially planar annular surface adjacent to the shank and substantially perpendicular to the shank; and
    at least one proximally inclined annular surface extending radially outward from the substantially planar annular surface.

17. The pipette tip coupling device and pipette tip assembly of claim 1 wherein the proximal coupler end surface comprises:

a substantially planar annular surface adjacent to the shank and substantially perpendicular to the shank;
an annular distally sloped surface extending radially outward from the substantially planar annular surface; and
an annular proximally sloped surface extending radially outward from the annular distally sloped surface.

18. A pipette tip coupling device and pipette tip assembly comprising:
a pipette tip comprising:
a circumscribing sidewall with an open interior passage including an interior surface extending along a central longitudinal axis of the pipette tip between an open proximal end and an open distal end;
a first section comprising a substantially cylindrical surface formed in the interior surface of the circumscribing sidewall distal to the open proximal end, the first section having a first diameter;
a second section comprising a substantially cylindrical surface formed in the interior surface of the circumscribing sidewall distal to the first section, the second section having a second diameter smaller than the first diameter;
a stop shoulder surface formed in the interior surface of the circumscribing sidewall at an interface of the first section and the second section;
a third section comprising a substantially cylindrical surface formed in the interior surface of the circumscribing sidewall distal to the second section, the third section having a third diameter smaller than the second diameter;
a sealing seat surface formed in the interior surface of the circumscribing sidewall at an interface of the second section and the third section; and
at least one frustoconical section formed in the interior surface of the circumscribing sidewall between the third section and the open distal end;
a pipette tip coupling device comprising:
a shank having a proximal end face;
a coupler body having a proximal coupler end surface, wherein the coupler body is distal to the shank, and wherein a diameter of a widest portion of the coupler body is greater than a diameter of a widest portion of the shank;
a distal stem portion comprising:
a proximal neck; and
a distal end plate;
an open-ended interior circumscribing surface forming an open passageway extending longitudinally from the proximal end face through the distal end plate;
a proximal elastomeric element, the proximal elastomeric element disposed around the shank and adjacent to the proximal coupler end surface; and
a distal elastomeric element, the distal elastomeric element disposed around the proximal neck of the distal stem portion and adjacent to the distal end plate of the distal stem portion;
wherein the proximal elastomeric element abuts against the first section of the pipette tip for securing the pipette tip to the pipette tip coupling device, and wherein the distal elastomeric element abuts against the sealing seat surface of the pipette tip to form a seal between the pipette tip coupling device and the pipette tip.

19. The pipette tip coupling device and pipette tip assembly of claim 18 wherein the stop shoulder surface is an annular, substantially planar surface substantially perpendicular to the central longitudinal axis of the pipette tip.

20. The pipette tip coupling device and pipette tip assembly of claim 18 wherein the stop shoulder surface further comprises:
an upwardly facing annular stop surface groove; and
an upwardly extending circumscribing rib.

21. The pipette tip coupling device and pipette tip assembly of claim 20 wherein the stop shoulder surface further comprises an internal seal in the upwardly facing annular stop surface groove.

22. The pipette tip coupling device and pipette tip assembly of claim 18 wherein the sealing seat surface is an annular, substantially planar surface substantially perpendicular to the central longitudinal axis of the pipette tip.

23. The pipette tip coupling device and pipette tip assembly of claim 18 wherein the sealing seat surface further comprises a circumferential upwardly facing tooth edge surface.

24. The pipette tip coupling device and pipette tip assembly of claim 18 wherein the sealing seat surface is a frustoconical annular surface further comprising:
an upper annular sealing seat surface edge at the intersection of the second section and the sealing seat surface; and
a lower annular sealing seat surface edge at the interface of the sealing seat surface and the third section, wherein the upper annular sealing seat surface edge is greater in diameter than the lower annular sealing seat surface edge.

25. The pipette tip coupling device and pipette tip assembly of claim 18 wherein the sealing seat surface is a circumferential radially convex surface.

26. The pipette tip coupling device and pipette tip assembly of claim 18 wherein the sealing seat surface is a circumferential radially concave surface.

27. The pipette tip coupling device and pipette tip assembly of claim 18 further comprising an annular chamfered interior surface formed in the interior surface of the circumscribing sidewall of the pipette tip extending radially inward from the open proximal end and terminating at the proximal end of the first section.

28. The pipette tip coupling device and pipette tip assembly of claim 18 wherein the at least one frustoconical section further comprises:
a fourth section formed in the interior surface of the circumscribing sidewall distal to the third section; and
a fifth section formed in the interior surface of the circumscribing sidewall distal to the fourth section and proximal to the distal open end, wherein the fifth section has a greater taper than the fourth section.

29. A pipette tip coupling device and pipette tip assembly comprising:
a pipette tip comprising:
a circumscribing sidewall with an open interior passage including an interior surface extending along a central longitudinal axis of the pipette tip between an open proximal end and an open distal end;
a first section formed in the interior surface of the circumscribing sidewall distal to the open proximal end comprising:
a substantially cylindrical upper first portion having a first diameter;
a substantially cylindrical lower first portion having the first diameter; and
an annular groove interposed between the substantially cylindrical upper first portion and the substantially cylindrical lower first portion;

a second section comprising a substantially cylindrical surface formed in the interior surface of the circumscribing sidewall distal to the first section, the second section having a second diameter smaller than the first diameter;

a stop shoulder surface formed in the interior surface of the circumscribing sidewall at an interface of the first section and the second section;

a third section comprising a substantially cylindrical surface formed in the interior surface of the circumscribing sidewall distal to the second section, the third section having a third diameter smaller than the second diameter;

a sealing seat surface formed in the interior surface of the circumscribing sidewall at an interface of the second section and the third section; and at least one frustoconical section formed in the interior surface of the circumscribing sidewall between the third section and the open distal end;

a pipette tip coupling device comprising:
 a shank having a proximal end face;
 a coupler body having a proximal coupler end surface, wherein the coupler body is distal to the shank, and wherein a diameter of a widest portion of the coupler body is greater than a diameter of a widest portion of the shank;
 a distal stem portion comprising:
  a proximal neck; and
  a distal end plate;
 an open-ended interior circumscribing surface forming an open passageway extending longitudinally from the proximal end face through the distal end plate;
 a proximal elastomeric element, the proximal elastomeric element disposed around the shank and adjacent to the proximal coupler end surface; and
 a distal elastomeric element, the distal elastomeric element disposed around the proximal neck of the distal stem portion and adjacent to the distal end plate of the distal stem portion;
wherein the proximal elastomeric element abuts against the annular groove in the first section, and wherein the distal elastomeric element abuts against the sealing seat surface of the pipette tip to form a seal between the pipette tip coupling device and the pipette tip.

30. The pipette tip coupling device and pipette tip assembly of claim 29 wherein the annular groove is concave.

* * * * *